US011285149B2

(12) United States Patent
Frank et al.

(10) Patent No.: US 11,285,149 B2
(45) Date of Patent: Mar. 29, 2022

(54) ENHANCED IMMUNOTHERAPY OF CANCER USING TARGETED TRANSCRIPTIONAL MODULATORS

(71) Applicant: DANA-FARBER CANCER INSTITUTE, INC., Boston, MA (US)

(72) Inventors: David Frank, Lexington, MA (US); Darwin Ye, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 150 days.

(21) Appl. No.: 16/633,780

(22) PCT Filed: Jul. 27, 2018

(86) PCT No.: PCT/US2018/043997
§ 371 (c)(1),
(2) Date: Jan. 24, 2020

(87) PCT Pub. No.: WO2019/023525
PCT Pub. Date: Jan. 31, 2019

(65) Prior Publication Data
US 2020/0230135 A1  Jul. 23, 2020

Related U.S. Application Data

(60) Provisional application No. 62/538,130, filed on Jul. 28, 2017.

(51) Int. Cl.
| *A61K 31/505* | (2006.01) |
| *A61K 31/12* | (2006.01) |
| *A61P 35/00* | (2006.01) |
| *A61P 35/02* | (2006.01) |
| *A61K 31/122* | (2006.01) |
| *C07K 16/28* | (2006.01) |
| *A61K 9/00* | (2006.01) |
| *A61K 45/06* | (2006.01) |

(52) U.S. Cl.
CPC .......... *A61K 31/505* (2013.01); *A61K 31/122* (2013.01); *A61P 35/02* (2018.01); *C07K 16/2818* (2013.01); *A61K 9/0019* (2013.01); *A61K 9/0053* (2013.01); *A61K 45/06* (2013.01)

(58) Field of Classification Search
CPC ........ A61K 31/505; A61K 31/12; A61P 35/00
USPC ................................................ 514/275, 682
See application file for complete search history.

(56) References Cited

U.S. PATENT DOCUMENTS

| 2010/0055102 A1 | 3/2010 | Langermann |
| 2015/0203848 A1 | 7/2015 | Yu et al. |

FOREIGN PATENT DOCUMENTS

| WO | 20100077634 A1 | 7/2010 |
| WO | 20160062722 A1 | 4/2016 |

OTHER PUBLICATIONS

Chunwan Lu et al: "JAK-STAT-mediated chronic inflammation impairs cytotoxic T lymphocyte activation to decrease anti-PD-1 immunotherapy efficacy in pancreatic cancer", Oncoimmunology, vol. 6, No. 3, Feb. 10, 2017 (Feb. 10, 2017), p. e1291106, XP055512383, DOI: 10.1080/2162402X.2017.1291106.
Taeko Hayakawa et al: "Enhanced anti-tumor effects of the PD-1/PD-L 1 blockade by combining a highly absorptive form of NF-kB/STAT3 inhibitor curcumin", Journal for Immunotherapy of Cancer, Biomed Central Ltd, London, UK, vol. 2, No. Suppl 3, Nov. 6, 2014 (Nov. 6, 2014), p. P210, XP021202477, ISSN: 2051-1426, DOI: 10.1186/2051-1426-2-S3-P210.
M. Chen et al: "Antifolate Activity of Pyrimethamine Enhances Temozolomide-Induced Cytotoxicity in Melanoma Cells", Molecular Cancer Research, vol. 7, No. 5, May 1, 2009 (May 1, 2009), pp. 703-712, XP55512579, US ISSN: 1541-7786, DOI: 10.1158/1541-7786.MCR-08-0263.
Xiang M. et al.: "Gene expression-based discovery of atovaquone as a STAT3 inhibitor and anticancer agent", Blood, Oct. 6, 2016 (Oct. 6, 2016), pp. 1845-1853, Retrieved from the Internet: URL:https://www.ncbi.nlm.nih.gov/pmc/articles/PMC5054697/? report=printable [retrieved on Oct. 4, 2018].
Database EMBase [Online] Elsevier Science Publishers, Amsterdam, NL; Jun. 1, 2017 (Jun. 1, 2017), Weller Met al: "Vaccine-based immunotherapeutic approaches to gliomas and beyond", XP002785357, Database accession No. EMB-20170394797 abstract & Weller Met al: "Vaccine-based immunotherapeutic approaches to gliomas and beyond", Nature Reviews Neurology Jun. 1, 2017 Nature Publishing Group GBR, vol. 13, No. 6, Jun. 1, 2017 (Jun. 1, 2017), pp. 363-374, ISSN: 1759-4758.
Weiss et al., "Recognizing and Exploiting Differences Between RNAi and Small-Molecule Inhibitors," 2007, Nat Chem Biol., 3(12): 739-744.

*Primary Examiner* — Raymond J Henley, III
(74) *Attorney, Agent, or Firm* — Burns & Levinson, LLP; Daniel W. Clarke

(57) ABSTRACT

The present invention relates to a combination of a signal transducer and activator of transcription 3 (STAT3) activity inhibitor; and an immune checkpoint inhibitor for use in treating or preventing the hyperproliferative disorder in a subject. Preferably, the STA3 activity inhibitor is pyrimethamine or atovaquone, and the immune checkpoint inhibitor is an anti-PD1 antibody. Preferably, the hyperproliferative disorder is a glioma or a glioblastoma.

24 Claims, 7 Drawing Sheets

Specification includes a Sequence Listing.

ENHANCED IMMUNOTHERAPY OF CANCER USING TARGETED TRANSCRIPTIONAL MODULATORS

RELATED APPLICATIONS

This application is a national stage application, filed under 35 U.S.C. § 371, of International Application No. PCT/US18/043997, filed Jul. 27, 2018, which claims the benefit of priority under 35 U.S.C. § 119(e) to U.S. Provisional Application No. 62/538,130, filed Jul. 28, 2017, each of which is incorporated herein by reference in its entirety.

GOVERNMENT LICENSE RIGHTS

This invention was made with government support under grant number R01-CA160979 awarded by the National Institutes of Health. The government has certain rights in the invention.

BACKGROUND OF THE INVENTION

The development of immune checkpoint inhibitors has allowed dramatic clinical responses to occur in patients with advanced cancers. However, not all patients benefit, and even those who do respond may have incomplete or transient eradication of their cancer. Thus, prior to the invention described herein, there was a critical unmet need for approaches to increase the degree of tumor regression and increase the durability of response to treatment.

SUMMARY OF THE INVENTION

The present invention is based upon the surprising discovery that the combination of a STAT3 inhibitor, e.g., pyrimethamine, and an immune checkpoint inhibitor, e.g., an anti-PD-1 antibody, unexpectedly leads to a highly active anti-tumor effect, dramatically superior to either treatment alone.

Accordingly, described herein is a method for treating or preventing a hyperproliferative disorder in a subject. First, a therapeutically effective amount of a signal transducer and activator of transcription 3 (STAT3) activity inhibitor is administered to the subject. Next, a therapeutically effective amount of an immune checkpoint inhibitor is administered to the subject, thereby treating or preventing the hyperproliferative disorder in the subject. In some cases, wherein the subject has been diagnosed with a hyperproliferative disorder.

In one aspect, the subject is identified as having elevated STAT3 activity or as in need of inhibiting STAT3 activity. The subject in need of inhibition of STAT3 will generally display enhanced STAT3 activity as described herein. It is readily apparent to one of ordinary skill in the art, based on the teachings herein, how to determine whether an individual has enhanced STAT3 activity.

Exemplary modes of administration of the STAT3 activity inhibitor and the immune checkpoint inhibitor include parental administration (e.g., subcutaneous and intravenous administration) and oral administration.

Exemplary STAT3 inhibitors include pyrimethamine, atovaquone, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 3-(1,3-benzodioxol-5-yl)-1,6-dimethyl-pyrimido[5,4-e]-1,2,4-triazine-5,7(-1H,6H)-dione, 2-(1,8-Naphthyridin-2-yl)phenol, 3-(2-hydroxyphenyl)-3-phenyl-N,N-dipropylpropanamide as well as any derivatives of these compounds or analogues thereof.

For example, pyrimethamine is administered at a dose of about 50 mg to about 100 mg (e.g., about 50 mg, about 60 mg, about 70 mg, about 80 mg, about 90 mg, or about 100 mg) by mouth at least once daily (e.g., once daily, twice daily, three times daily or four times daily). In another example, atovaquone is administered at a dose of about 1500 mg by mouth at least once daily (e.g., once daily, twice daily, three times daily or four times daily).

For example, the STAT3 activity is selected from the group consisting of STAT3 phosphorylation, STAT3 dimerization, STAT3 binding to a polynucleotide comprising a STAT3 binding site, STAT3 binding to genomic DNA (as could be assessed by cromatin immunoprecipitation (ChIP)), activation of a STAT3 responsive gene and STAT3 nuclear translocation.

In one example, the STAT3 responsive gene comprises an immune-stimulatory protein selected from the group consisting of inducible costimulator-ligand (Icos-L), CD70, tumor necrosis factor-like protein 1A (TL1A), OX40-L, 4-1BB ligand (4-1BBL), glucocorticoid-induced TNFR-related protein ligand (GITR-L), and CD40.

In another example, the STAT3 responsive gene comprises an immune-inhibitory protein selected from the group consisting of programmed death-ligand 1 (PD-L1), B7-H3, B- and T-lymphocyte attenuator (BTLA), CD47, Fas ligand (Fas-L), human herpes virus entry mediator (HVEM), indoleamine-pyrrole 2,3-dioxygenase (IDO1), transforming growth factor beta (TGF-β), and interleukin-10 (IL-10).

In some cases, STAT3 inhibitor is administered prior to administration of the immune checkpoint inhibitor. In other cases, the STAT3 inhibitor is administered simultaneously with the immune checkpoint inhibitor. In one aspect, the STAT3 inhibitor and the immune checkpoint inhibitor are administered soon after diagnosis with a hyperproliferative disorder, e.g., neoplasia, and before relapse of the disorder.

Exemplary immune checkpoint inhibitors include an inhibitor of programmed death 1 receptor (PD-1), an inhibitor of programmed death 1 ligand (PD-L1), an inhibitor of PD-L2, an inhibitor of cytotoxic T-lymphocyte antigen 4 (CTLA-4), an inhibitor of T-cell immunoglobulin and mucin-domain containing-3 (TIM-3), an inhibitor of lymphocyte-activation gene 3 (LAG-3) (LAG-3), an inhibitor of V-domain Ig suppressor of T cell activation (VISTA), an inhibitor of T cell immunoreceptor with Ig and immunoreceptor tyrosine-based inhibition motif domains (TIGIT), or an inhibitor of B and T Lymphocyte Attenuator (BTLA; CD272).

For example, nivolumab is administered at a dose of about 240 mg given intravenously every two weeks. In another example, pembrolizumab is administered at a dose of about 2 mg/kg given intravenously every three weeks. In yet another example, ipilimumab is administered at a dose of about 3 mg/kg given intravenously every three weeks.

Inhibition of an immune checkpoint molecule can be performed by inhibition at the DNA, RNA or protein level. In one aspect, an inhibitory nucleic acid (e.g., a dsRNA, siRNA or shRNA), can be used to inhibit expression of an immune checkpoint molecule. In another example, the inhibitor of an inhibitory signal is, a polypeptide, e.g., a soluble ligand, or an antibody or antigen-binding fragment thereof, that binds to the inhibitory molecule. For example, the inhibitor of PD-1 comprises pembrolizumab or nivolumab. In another example, the inhibitor of PD-L1 comprises atezolizumab, avelumab, or durvalumab. In yet another example, the inhibitor of CTLA-4 is ipilimumab.

A exemplary hyperproliferative disorder includes cancer. For example, the hyperproliferative disorder comprises a solid tumor or a hematological cancer. In some cases, the solid tumor is selected from the group consisting of breast cancer, melanoma, colon cancer, ovarian cancer, pancreatic cancer, lung cancer, hepatic cancer, head and neck cancer, prostate cancer and brain cancer. In other cases, the hematological cancer comprises leukemia or multiple myeloma. Suitable leukemias include acute lymphoblastic leukemia, acute myelogenous leukemia, chronic myelogenous leukemia, Hodgkin's disease, non-Hodgkin's lymphoma, T-cell lymphoma, B-cell lymphoma and chronic lymphocytic leukemia.

In one aspect, the hyperproliferative disorder comprises a glioma, e.g., a glioblastoma. Preferably, the subject is a human.

In some cases, the methods further comprise administering a chemotherapeutic agent.

Also provided are methods of increasing the immunogenicity of a tumor cell in a subject by (1) administering to the subject a therapeutically effective amount of a STAT3 activity inhibitor; and (2) administering to the subject a therapeutically effective amount of an immune checkpoint inhibitor, thereby increasing the immunogenicity of the tumor cell.

Methods of increasing the effectiveness of an effector T cell, e.g., the ability of the effector T cell to kill a tumor cell, are carried out by (1) administering to the subject a therapeutically effective amount of a STAT3 activity inhibitor; and (2) administering to the subject a therapeutically effective amount of an immune checkpoint inhibitor, thereby increasing the effectiveness of an effector T cell. For example, the effector T cell comprises a $CD4^+$ T cell or a $CD8^+$ T cell.

Also provided are kits comprising a therapeutically effective amount of a STAT3 activity inhibitor; and a therapeutically effective amount of an immune checkpoint inhibitor. For example, the STAT3 activity inhibitor comprises pyrimethamine or atovaquone and the immune checkpoint inhibitor comprises an anti-PD-1 antibody.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

The term "antineoplastic agent" is used herein to refer to agents that have the functional property of inhibiting a development or progression of a neoplasm in a human. Inhibition of metastasis is frequently a property of antineoplastic agents.

By "agent" is meant any small compound, antibody, nucleic acid molecule, or polypeptide, or fragments thereof.

By "alteration" is meant a change (increase or decrease) in the expression levels or activity of a gene or polypeptide as detected by standard art-known methods such as those described herein. As used herein, an alteration includes at least a 1% change in expression levels, e.g., at least a 2%, 3%, 4%, 5%, 6%, 7%, 8%, 9%, 10%, 20%, 30%, 40%, 50%, 60%, 70%, 80%, 90%, or 100% change in expression levels. For example, an alteration includes at least a 5%-10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Also provided are variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc.). Chimeric antibodies also include primatized and humanized antibodies. Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions. An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc$_\varepsilon$RI.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ M$^{-1}$, or greater than or equal to about $10^5$ M$^{-1}$, greater than or equal to about $10^6$ M$^{-1}$, greater than or equal to about $10^7$ M$^{-1}$, or greater than or equal to $10^8$ M$^{-1}$. Affinity of an antibody for its cognate antigen is also commonly expressed as a dissociation constant $K_D$, and in certain embodiments, HuM2e antibody specifically binds to M2e if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (*Ann. N.Y. Acad. Sci. USA* 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody. The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

By "binding to" a molecule is meant having a physicochemical affinity for that molecule.

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g., β-galactosidase or luciferase). Depending on the method used for detection, the amount and measurement of the change can vary. Determination of statistical significance is within the ability of those skilled in the art, e.g., the number of standard deviations from the mean that constitute a positive result.

"Detect" refers to identifying the presence, absence, or amount of the agent (e.g., a nucleic acid molecule, for example deoxyribonucleic acid (DNA) or ribonucleic acid (RNA)) to be detected.

By "detectable label" is meant a composition that when linked (e.g., joined—directly or indirectly) to a molecule of interest renders the latter detectable, via, for example, spectroscopic, photochemical, biochemical, immunochemical, or chemical means. Direct labeling can occur through bonds or interactions that link the label to the molecule, and indirect labeling can occur through the use of a linker or bridging moiety which is either directly or indirectly labeled. Bridging moieties may amplify a detectable signal. For example, useful labels may include radioactive isotopes, magnetic beads, metallic beads, colloidal particles, fluorescent labeling compounds, electron-dense reagents, enzymes (for example, as commonly used in an enzyme-linked immunosorbent assay (ELISA)), biotin, digoxigenin, or haptens. When the fluorescently labeled molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, p-phthaldehyde and fluorescamine. The molecule can also be detectably labeled using fluorescence emitting metals such as $^{152}$Eu, or others of the lanthanide series. These metals can be attached to the molecule using such metal chelating groups as diethylenetriaminepentacetic acid (DTPA) or ethylenediaminetetraacetic acid (EDTA). The molecule also can be detectably labeled by coupling it to a chemiluminescent compound. The presence of the chemiluminescent-tagged molecule is then determined by detecting the presence of luminescence that arises during the course of chemical reaction. Examples of particularly useful chemiluminescent labeling compounds are luminol, isoluminol, theromatic acridinium ester, imidazole, acridinium salt and oxalate ester.

A "detection step" may use any of a variety of known methods to detect the presence of nucleic acid (e.g., methylated DNA) or polypeptide. The types of detection methods in which probes can be used include Western blots, Southern blots, dot or slot blots, and Northern blots.

As used herein, the term "diagnosing" refers to classifying pathology or a symptom, determining a severity of the pathology (e.g., grade or stage), monitoring pathology progression, forecasting an outcome of pathology, and/or determining prospects of recovery.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease, e.g., cancer, relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion, e.g., a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "immunogenicity" is meant the ability of a particular substance, such as an antigen or epitope, to provoke an immune response in the body of a human or animal.

By "marker" is meant any protein or polynucleotide having an alteration in expression level or activity that is associated with a disease or disorder, e.g., neoplasia.

By "modulate" is meant alter (increase or decrease). Such alterations are detected by standard art-known methods such as those described herein.

The term, "normal amount" refers to a normal amount of a complex in an individual known not to be diagnosed with neoplasia. The amount of the molecule can be measured in a test sample and compared to the "normal control level," utilizing techniques such as reference limits, discrimination limits, or risk defining thresholds to define cutoff points and abnormal values (e.g., for neoplasia). The "normal control level" means the level of one or more proteins (or nucleic acids) or combined protein indices (or combined nucleic acid indices) typically found in a subject known not to be suffering from neoplasia. Such normal control levels and cutoff points may vary based on whether a molecule is used alone or in a formula combining other proteins into an index. Alternatively, the normal control level can be a database of protein patterns from previously tested subjects who did not convert to neoplasia over a clinically relevant time horizon. In another aspect, the normal control level can be a level relative to a housekeeping gene.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease in question or is not at risk for the disease.

Relative to a control level, the level that is determined may be an increased level. As used herein, the term "increased" with respect to level (e.g., expression level, biological activity level, etc.) refers to any % increase above a control level. The increased level may be at least or about a 1% increase, at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, or at least or about a 95% increase, relative to a control level.

Relative to a control level, the level that is determined may be a decreased level. As used herein, the term "decreased" with respect to level (e.g., expression level, biological activity level, etc.) refers to any % decrease below a control level. The decreased level may be at least or about a 1% decrease, at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, or at least or about a 95% decrease, relative to a control level.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity, e.g., at least 80%, at least 85%, at least 90%, at least 95%, or at least 99% identity. Polynucleotides having "substantial identity" to an endogenous sequence are typically capable of hybridizing with at least one strand of a double-stranded nucleic acid molecule.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "neoplasia" is meant a disease or disorder characterized by excess proliferation or reduced apoptosis. Illustrative neoplasms for which the invention can be used include, but are not limited to pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

As used herein, "obtaining" as in "obtaining an agent" includes synthesizing, purchasing, or otherwise acquiring the agent.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

The terms "preventing" and "prevention" refer to the administration of an agent or composition to a clinically asymptomatic individual who is at risk of developing, susceptible, or predisposed to a particular adverse condition, disorder, or disease, and thus relates to the prevention of the occurrence of symptoms and/or their underlying cause.

The term "prognosis," "staging," and "determination of aggressiveness" are defined herein as the prediction of the degree of severity of the neoplasia and of its evolution as well as the prospect of recovery as anticipated from usual course of the disease. Once the aggressiveness has been determined, appropriate methods of treatments are chosen.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

A "reference sequence" is a defined sequence used as a basis for sequence comparison or a gene expression comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 40 nucleotides, preferably at least about 60 nucleotides, more preferably at least about 75 nucleotides, and even more preferably about 100 nucleotides or about 300 or about 500 nucleotides or any integer thereabout or there between.

The term "sample" as used herein refers to a biological sample obtained for the purpose of evaluation in vitro. Exemplary tissue samples for the methods described herein include tissue samples from tumors or the surrounding microenvironment (i.e., the stroma and/or infiltrating immune cells). With regard to the methods disclosed herein, the sample or patient sample preferably may comprise any body fluid or tissue. In some embodiments, the bodily fluid includes, but is not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of a blood sample, a plasma sample, a serum sample, and a urine sample. In exemplary aspects, the sample comprises blood or a fraction thereof (e.g., plasma, serum, fraction obtained via leukapheresis). Preferred samples are whole blood, serum, plasma, or urine. A sample can also be a partially purified fraction of a tissue or bodily fluid.

A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, at least 70%, at least 80%, at least 85%, at least 90%, at least 95%, or at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "subject" as used herein includes all members of the animal kingdom prone to suffering from the indicated disorder. In some aspects, the subject is a mammal, e.g., a human mammal or a non-human mammal. The methods are also applicable to companion animals such as dogs and cats as well as livestock such as cows, horses, sheep, goats, pigs, and other domesticated and wild animals.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with cancer is within the ability of those in the art. Subjects suffering from, and suspected of suffering from, a specific disease, condition, or syndrome are not necessarily two distinct groups.

As used herein, "susceptible to" or "prone to" or "predisposed to" or "at risk of developing" a specific disease or condition refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

As used herein, in one aspect, the "tumor microenvironment" (TME) is the cellular environment in which a tumor exists, e.g., surrounding blood vessels, immune cells, fibroblasts, bone marrow-derived inflammatory cells, lymphocytes, signaling molecules and the extracellular matrix (ECM). The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of cancerous cells, such as in immuno-editing.

In some cases, a composition of the invention is administered orally or systemically. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy may be most appropriate for pulmonary vascular diseases (e.g., pulmonary hypertension).

Pharmaceutical compositions may be assembled into kits or pharmaceutical systems for use in arresting cell cycle in rapidly dividing cells, e.g., cancer cells. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using the kit.

Any compositions or methods provided herein can be combined with one or more of any of the other compositions and methods provided herein.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

DETAILED DESCRIPTION OF THE INVENTION

Figure 1:
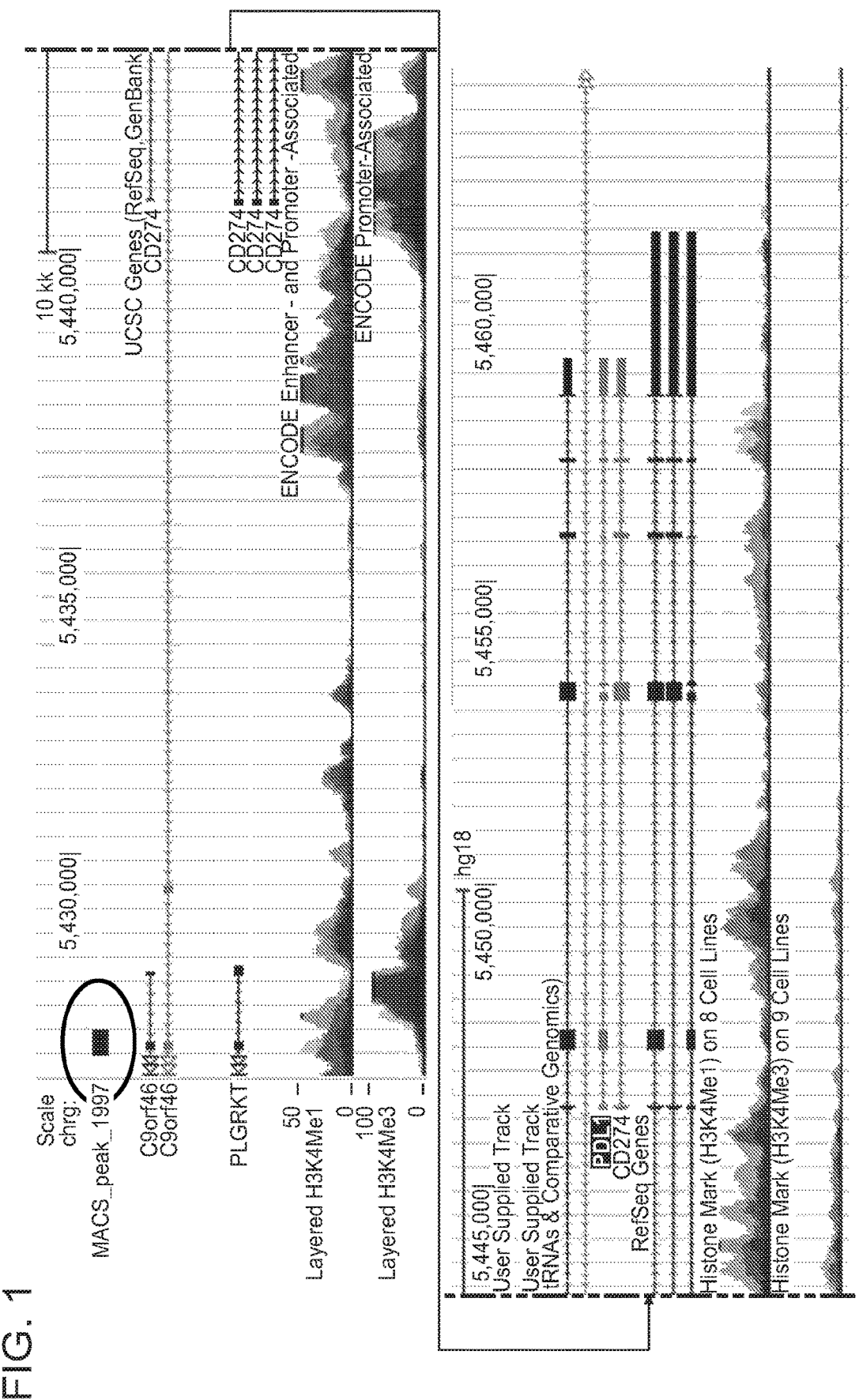
FIG. 1 is a graph showing that ChIP-seq identifies STAT3 binding in immunomodulatory genes. ChIP-seq reveals STAT3 binding (red oval) in proximity to the PD-L1 gene (CD274). Similar binding was found for the other 15 immunomodulatory genes.

The invention is based, at least in part, upon the identification that transcription factors, e.g., STAT3, which are constitutively active in cancer cells, regulate the expression of genes that control the immunogenicity of tumor cells and the responsiveness of immune cells in the surrounding microenvironment. This includes immunosuppressive genes (such as PD-L1, B7-H3, CD155, IL-10, and TGF-b), that are upregulated by STAT3, and immunostimulatory genes (such as CD80, ICosL, 4-1BBL, and CD40) that are down regulated by STAT3. Consequently, as described in detail below, when cells are treated with an inhibitor of STAT3, the tumor itself becomes more immunogenic, and the suppression of T cell effector function and antigen presentation mediated by the cancer is reversed.

As described below in an animal model, the combination of a STAT3 inhibitor, e.g., pyrimethamine, with an immune checkpoint inhibitor, e.g., an anti-PD-1 antibody, unexpectedly leads to a highly active anti-tumor effect, superior to either treatment alone. Because drugs like pyrimethamine and atovaquone are already FDA-approved, the treatment modalities described herein are readily applicable to human patients. The clinical strategy described herein of targeting oncogenic transcription factors in conjunction with immune checkpoint blockade holds the potential to greatly enhance the number of patients who would benefit from this therapy, as well as the degree of benefit conferred by this approach.

Glioma

A glioma is a type of tumor that starts in the brain or spine and is so named because it arises from glial cells. Gliomas comprise about 30% of all brain and central nervous system tumors, about 80% of all malignant brain tumors, and are among the most aggressive human tumors (Goodenberger M L and Jenkins R B, 2012 Cancer Genet., 205: 613-621; Holland E C, Nat Rev Genet, 2:120-129; Konopka G and Bonni A, 2003 Curr Mol Med, 3:73-84; Louis D N, 2006 Annu Rev Pathol, 1:97-117; Furnari et al., 2007 Genes Dev, 21:2683-2710).

Gliomas represent among the most lethal tumors in both children and adults. They are often impossible to surgically eradicate, they are only marginally more sensitive to radiation than the surrounding brain, and they are minimally responsive to cytotoxic chemotherapy.

Gliomas are classified by cell type, by grade, and by location. First, gliomas are named according to the specific type of cell with which they share histological features, but not necessarily from which they originate. The main types of gliomas are: ependymomas (ependymal cells); astrocytomas (astrocytes (glioblastoma multiforme is a malignant astrocytoma and the most common primary brain tumor among adults); oligodendrogliomas (oligodendrocytes); brainstem glioma (develop in the brain stem); optic nerve glioma (develop in or around the optic nerve); and mixed gliomas, such as oligoastrocytomas, contain cells from different types of glia.

Gliomas are further categorized according to their grade, which is determined by pathologic evaluation of the tumor. Low-grade gliomas [WHO grade II] are well-differentiated (not anaplastic); these tend to exhibit benign tendencies and portend a better prognosis for the patient. However, they have a uniform rate of recurrence and increase in grade over time so should be classified as malignant. High-grade [WHO grade III-IV] gliomas are undifferentiated or anaplastic; these are malignant and carry a worse prognosis. Of numerous grading systems in use, the most common is the World Health Organization (WHO) grading system for astrocytoma, under which tumors are graded from I (least advanced disease—best prognosis) to IV (most advanced disease—worst prognosis).

Gliomas can also be classified according to whether they are above or below a membrane in the brain called the tentorium. The tentorium separates the cerebrum (above) from the cerebellum (below). Supratentorial tumors are above the tentorium, in the cerebrum, and mostly found in adults (70%). Infratentorial tumors are below the tentorium, in the cerebellum, and mostly found in children (70%). Pontine tumors are located in the pons of the brainstem. The brainstem has three parts (pons, midbrain, and medulla); the pons controls critical functions such as breathing, making surgery on these extremely dangerous.

Targeted therapy, which has been successful in many forms of cancer, has had much less of an impact on gliomas, as these tumors are not characterized by highly recurrent driver mutations. To develop more effective, rationally guided therapy for these tumors, an alternate approach was pursued. First, key convergence points of multiple oncogenic pathways in gliomas were focused on. This led to the identification of the transcription factor, STAT3, which was activated inappropriately in a large fraction of gliomas. As described herein, constitutive STAT3 activation leads to increased expression of genes that regulate cell cycle entry, survival, invasion, angiogenesis, and pluripotency, thereby directly promoting the malignant behavior of glioma cells. Furthermore, as described in detail below, it was identified that genes that minimize the immunogenicity of glioma cells are also under the regulation of STAT3.

Glioblastoma

Clinical outcomes for patients with glioblastoma (also known as glioblastoma multiforme; GBM) remain extremely poor, and prior to the invention described herein, there was a huge unmet need for rational therapies. Although mutations in a small number of genes, such as the epidermal growth factor (EGF) receptor, have been found recurrently in a subset of glioblastomas, a dominant mutated therapeutic target has not emerged for this disease.

When viewed with magnetic resonance imaging (MRI), glioblastomas often appear as ring-enhancing lesions. The appearance is not specific, however, as other lesions such as abscess, metastasis, tumefactive multiple sclerosis, and other entities may have a similar appearance. Definitive diagnosis of a suspected GBM on computerized tomography (CT) or MRI requires a stereotactic biopsy or a craniotomy with tumor resection and pathologic confirmation. Because the tumor grade is based upon the most malignant portion of the tumor, biopsy or subtotal tumor resection can result in undergrading of the lesion. Imaging of tumor blood flow using perfusion Mill and measuring tumor metabolite concentration with magnetic resonance spectroscopy may add value to standard MRI in select cases by showing increased relative cerebral blood volume and increased choline peak respectively, but pathology remains the gold standard for diagnosis and molecular characterization.

As described herein, a second strategy to identify targets with high therapeutic index is to identify common non-mutated dependencies through which multiple signaling pathways converge. As described in detail below, one such signaling node is the transcription factor STAT3. While this protein is not mutated in glioblastoma, it is activated constitutively in a large proportion of patients' tumors, and activated STAT3 is associated with poor survival in glioblastoma (Alvarez et al., 2007 Translational Oncogenomics, 2:97-103). In addition to direct effects on cell autonomous behavior, the activation of STAT3 in a tumor cell also promotes immune evasion. This effect is mediated by increased expression of cell surface molecules including programmed death-ligand 1 (PD-L1) and Fas ligand (FasL), which directly inhibit immune cell function, as well as through the production of cytokines such as interleukin-10 (IL-10) and transforming growth factor-beta (TGF-β), which decrease the function of antigen presenting cells and T lymphocytes (Marotta et al., 2011 J Clin Invest., 121(7): 2723-35; Yu et al., 2009 Nature Reviews Cancer, 9(11):798-809). Given these findings, and the fact that STAT3 inhibition can be tolerated in normal cells with little deleterious effect, inhibition of STAT3 is explored herein as a therapeutic strategy for gliomas.

STAT Molecules

Members of the signal transducer and activator of transcription (STAT) protein family are intracellular transcription factors that mediate many aspects of cellular immunity, proliferation, apoptosis and differentiation. There are seven mammalian STAT family members that have been identified: STAT1, STAT2, STAT3, STAT4, STAT5 (STAT5A and STAT5B), and STATE. STAT proteins are primarily activated by membrane receptor-associated Janus kinases (JAK). Dysregulation of the JAK/STAT pathway is frequently observed in primary tumors and leads to increased angiogenesis, enhanced survival of tumors, and immunosuppression. STAT proteins are involved in the development and function of the immune system and play a role in maintaining immune tolerance and tumor surveillance.

STAT proteins are present in the cytoplasm of cells under basal conditions. When activated by tyrosine phosphorylation, STAT proteins form dimers and translocate to the nucleus where they can bind specific nine base pair sequences in the regulatory regions of target genes, thereby activating transcription. A variety of tyrosine kinases, including polypeptide growth factor receptors, Src family members, and other kinases can catalyze this phosphorylation. While tyrosine phosphorylation is essential for their activation, STAT proteins can also be phosphorylated on unique serine residues. Although this is not sufficient to induce dimerization and DNA binding, STAT serine phosphorylation modulates the transcriptional response mediated by a tyrosine-phosphorylated STAT dimer, and may mediate distinct biological effects (Zhang X, et al. Science 1995; 267:1990-1994; Wen Z, et al. Cell 1995; 82:241-250; Kumar A, et al. Science 1997; 278:1630-1632.). STAT proteins have been found to function inappropriately in many human malignancies (Alvarez J V, et al., Cancer Res 2005; 65(12): 5054-62; Frank D A, et al. Cancer Treat. Res. 2003; 115: 267-291; Bowman T, et al. Oncogene 2000; 19(21):2474-88).

STAT3 and STAT Modulators

STAT3 is activated in several human tumors, including common epithelial cancers such as cancer of the breast, prostate, lung, pancreas, and ovary; hematologic cancers such as multiple myeloma, and acute leukemias; and diverse tumors such as melanoma and gliomas (Frank D A, et al. Cancer Treat. Res. 2003; 115:267-291). Many of the target genes of STAT3 code for proteins involved in cell survival, cell cycle progression, differentiation inhibition, invasion, and angiogenesis, all of the essential processes necessary for tumor formation and maintenance (Alvarez J V, et al., Cancer Res 2005; 65(12):5054-62). Inhibition of STAT3 function in cancer cells associated with enhanced STAT3 activity leads to a loss of proliferation and survival of the cancer cells (Frank D A. Curr. Cancer Therapy Reviews 2006; 2:57-65). Despite the central role that STAT3 plays in these diverse processes in tumor cell biology, loss of STAT3 function in normal adult cells has few if any serious consequences, and may in fact decrease the ability of a cell to become transformed.

```
An exemplary human STAT3 amino acid sequence is set forth below (SEQ ID NO: 33;
GenBank Accession No: AAH14482, Version 1, incorporated herein by reference):
    1   maqwnqlqql dtryleqlhq lysdsfpmel rqflapwies qdwayaaske shatlvfhnl 61   lgeidqqysr flqesnvlyq hnlrrikqfl qsrylekpme iarivarclw eesrllqtaa 121   taaqqggqan hptaavvtek qqmleghlqd vrkrvqdleq kmkvvenlqd dfdfnyktlk 181   sqgdmqdlng nnqsvtrqkm qqlegmltal dqmrrsivse lagllsamey vqktltdeel 241   adwkrrqqia ciggppnicl drlenwitsl aesqlqtrqq ikkleelqqk vsykgdpivq 301   hrpmleeriv elfrnlmksa fvverqpcmp mhpdrplvik tgvqfttkvr llvkfpelny
```

-continued

```
361  qlkikvcidk dsgdvaalrg srkfnilgtn tkvmnmeesn ngslsaefkh ltlreqrcgn 421  ggrancdasl ivteelhlit fetevyhqgl kidlethslp vvvisnicqm pnawasilwy 481  nmltnnpknv nfftkppigt wdqvaevlsw qfssttkrgl sieqlttlae kllgpgvnys 541  gcgitwakfc kenmagkgfs fwvwldniid lvkkyilalw negyimgfis kererailst 601  kppgtfllrf sesskeggvt ftwvekdisg ktqiqsvepy tkqqlnnmsf aeiimgykim 661  datnilvspl vylypdipke eafgkycrpe sqehpeadpg saapylktkf icvtpttcsn 721  tidlpmsprt ldslmqfgnn gegaepsagg qfesltfdme ltsecatspm
```

An exemplary human STAT3 nucleic acid sequence is set forth below (SEQ ID NO: 34; GenBank Accession No: NM_139276, Version 2, incorporated herein by reference):

```
   1  ggtttccgga gctgcggcgg cgcagactgg gagggggagc cggggggttcc gacgtcgcag 61  ccgagggaac aagccccaac cggatcctgg acaggcaccc cggcttggcg ctgtctctcc 121  ccctcggctc ggagaggccc ttcggcctga gggagcctcg ccgcccgtcc ccggcacacg 181  cgcagcccg gcctctcggc tctgccgga gaacagttg ggaccctga ttttagcagg 241  atgcccaat ggaatcagct acagcagctt gacacacggt acctggagca gctccatcag 301  ctctacagtg acagcttccc aatggagctg cggcagtttc tggcccttg gattgagagt 361  caagattggg catatgcggc cagcaaagaa tcacatgcca ctttggtgtt tcataatctc 421  ctgggagaga ttgaccagca gtatagccgc ttcctgcaag agtcgaatgt tctctatcag 481  cacaatctac gaagaatcaa gcagtttctt cagagcaggt atcttgagaa gccaatggag 541  attgcccga ttgtggcccg gtgcctgtgg gaagaatcac gccttctaca gactgcagcc 601  actgcggccc agcaaggggg ccaggccaac caccccacag cagccgtggt gacggagaag 661  cagcagatgc tggagcagca ccttcaggat gtccggaaga gagtgcagga tctagaacag 721  aaaatgaaag tggtagagaa tctccaggat gactttgatt tcaactataa accctcaag 781  agtcaaggag acatgcaaga tctgaatgga aacaaccagt cagtgaccag gcagaagatg 841  cagcagctgg aacagatgct cactgcgctg gaccagatgc ggagaagcat cgtgagtgag 901  ctggcggggc ttttgtcagc gatggagtac gtgcagaaaa ctctcacgga cgaggagctg 961  gctgactgga agaggcggca acagattgcc tgcattggag gcccgcccaa catctgccta 1021  gatcggctag aaaactggat aacgtcatta gcagaatctc aacttcagac ccgtcaacaa 1081  attaagaaac tggaggagtt gcagcaaaaa gtttcctaca aggggacccc cattgtacag 1141  caccggccga tgctggagga gagaatcgtg gagctgttta gaaacttaat gaaaagtgcc 1201  tttgtggtgg agcggcagcc ctgcatgccc atgcatcctg accggcccct cgtcatcaag 1261  accggcgtcc agttcactac taaagtcagg ttgctggtca attccctga gttgaattat 1321  cagcttaaaa ttaaagtgtg cattgacaaa gactctgggg acgttgcagc tctcagagga 1381  tcccggaaat ttaacattct gggcacaaac acaaaagtga tgaacatgga agaatccaac 1441  aacggcagcc tctctgcaga attcaaacac ttgaccctga gggagcagag atgtgggaat 1501  ggggggccgag ccaattgtga tgcttccctg attgtgactg aggagctgca cctgatcacc 1561  tttgagaccg aggtgtatca ccaaggcctc aagattgacc tagaccccca ctccttgcca 1621  gttgtggtga tctccaacat ctgtcagatg ccaaatgcct gggcgtccat cctgtggtac 1681  aacatgctga ccaacaatcc caagaatgta aacttttta ccaagccccc aattggaacc 1741  tgggatcaag tggccgaggt cctgagctgg cagttctcct ccaccaccaa gcgaggactg 1801  agcatcgagc agctgactac actggcagag aaactcttgg gacctggtgt gaattattca 1861  gggtgtcaga tcacatgggc taaattttgc aaagaaaaca tggctggcaa gggcttctcc
```

```
1921  ttctgggtct ggctggacaa tatcattgac cttgtgaaaa agtacatcct ggcccttggg
1981  aacgaagggt acatcatggg ctttatcagt aaggagcggg agcgggccat cttgagcact
2041  aagcctccag gcaccttcct gctaagattc agtgaaagca gcaagaagg aggcgtcact
2101  ttcacttggg tggagaagga catcagcggt aagacccaga tccagtccgt ggaaccatac
2161  acaaagcagc agctgaacaa catgtcattt gctgaaatca tcatgggcta aagatcatg
2221  gatgctacca atatcctggt gtctccactg gtctatctct atcctgacat tcccaaggag
2281  gaggcattcg gaaagtattg tcggccagag agccaggagc atcctgaagc tgacccaggt
2341  agcgctgccc cataccgaa gaccaagttt atctgtgtga caccaacgac ctgcagcaat
2401  accattgacc tgccgatgtc cccccgcact ttagattcat tgatgcagtt tggaaataat
2461  ggtgaaggtg ctgaaccctc agcaggaggg cagtttgagt ccctcacctt tgcatggag
2521  ttgacctcgg agtgcgctac ctcccccatg tgaggagctg agaacggaag ctgcagaaag
2581  atacgactga ggcgcctacc tgcattctgc caccctcac acagccaaac cccagatcat
2641  ctgaaactac taactttgtg gttccagatt ttttttaatc tcctacttct gctatctttg
2701  agcaatctgg gcacttttaa aaatagagaa atgagtgaat gtgggtgatc tgcttttatc
2761  taaatgcaaa taaggatgtg ttctctgaga cccatgatca ggggatgtgg cggggggtgg
2821  ctagagggag aaaaaggaaa tgtcttgtgt tgttttgttc cctgccctc ctttctcagc
2881  agcttttgt tattgttgtt gttgttctta dacaagtgcc tcctggtgcc tgcggcatcc
2941  ttctgcctgt ttctgtaagc aaatgccaca ggccacctat agctacatac tcctggcatt
3001  gcacttttta accttgctga catccaaata aagatagga ctatctaagc cctaggtttc
3061  tttttaaatt aagaaataat aacaattaaa gggcaaaaaa cactgtatca gcatagcctt
3121  tctgtattta agaaacttaa gcagccgggc atggtggctc acgcctgtaa tcccagcact
3181  ttgggaggcc gaggcggatc ataaggtcag gagatcaaga ccatcctggc taacacggtg
3241  aaacccgtc tctactaaaa gtacaaaaaa ttagctgggt gtggtggtgg gcgcctgtag
3301  tcccagctac tcgggaggct gaggcaggag aatcgcttga acctgagagg cggaggttgc
3361  agtgagccaa aattgcacca ctgcacactg cactccatcc tgggcgacag tctgagactc
3421  tgtctcaaaa aaaaaaaaa aaaaagaaaa cttcagttaa cagcctcctt ggtgctttaa
3481  gcattcagct tccttcaggc tggtaattta taatccct gaaacgggct tcaggtcaaa
3541  cccttaagac atctgaagct gcaacctggc ctttggtgtt gaaataggaa ggtttaagga
3601  gaatctaagc attttagact tttttttata aatagactta ttttcctttg taatgtattg
3661  gccttttagt gagtaaggct gggcagaggg tgcttacaac cttgactccc tttctccctg
3721  gacttgatct gctgtttcag aggctaggtt gtttctgtgg gtgccttatc agggctggga
3781  tacttctgat tctggcttcc ttcctgcccc accctcccga ccccagtccc cctgatcctg
3841  ctagaggcat gtctccttgc gtgtctaaag gtccctcatc ctgtttgttt taggaatcct
3901  ggtctcagga cctcatggaa gaagagggg agagagttac aggttggaca tgatgcacac
3961  tatgggccc cagcgacgtg tctggttgag ctcagggaat atggttctta gccagtttct
4021  tggtgatatc cagtggcact tgtaatggcg tcttcattca gttcatgcag ggcaaaggct
4081  tactgataaa cttgagtctg ccctcgtatg agggtgtata cctggcctcc ctctgaggct
4141  ggtgactcct ccctgctggg gccccacagg tgaggcagaa cagctagagg gcctccccgc
4201  ctgcccgcct tggctggcta gctcgcctct cctgtgcgta tgggaacacc tagcacgtgc
4261  tggatgggct gcctctgact cagaggcatg gccggatttg gcaactcaaa accaccttgc
4321  ctcagctgat cagagtttct gtggaattct gtttgttaaa tcaaattagc tggtctctga
```

```
-continued
4381  attaagggg  agacgacctt  ctctaagatg  aacagggttc  gccccagtcc  tcctgcctgg 4441  agacagttga  tgtgtcatgc  agagctctta  cttctccagc  aacactcttc  agtacataat 4501  aagcttaact  gataaacaga  atatttagaa  aggtgagact  tgggcttacc  attgggttta 4561  aatcataggg  acctagggcg  agggttcagg  gcttctctgg  agcagatatt  gtcaagttca 4621  tggccttagg  tagcatgtat  ctggtcttaa  ctctgattgt  agcaaaagtt  ctgagaggag 4681  ctgagccctg  ttgtggccca  ttaaagaaca  gggtcctcag  gccctgcccg  cttcctgtcc 4741  actgccccct  ccccatcccc  agcccagccg  agggaatccc  gtgggttgct  tacctaccta 4801  taaggtggtt  tataagctgc  tgtcctggcc  actgcattca  aattccaatg  tgtacttcat 4861  agtgtaaaaa  tttatattat  tgtgaggttt  tttgtctttt  tttttttttt  ttttttttgg 4921  tatattgctg  tatctacttt  aacttccaga  aataaacgtt  atataggaac  cgtaaaaa
```

The following compounds are STAT3 inhibitors: pyrimethamine, atovaquone, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 3-(1,3-benzodioxol-5-yl)-1,6-dimethyl-pyrimido[5,4-e]-1,2,4-triazine-5,7(-1H,6H)-dione, 2-(1,8-Naphthyridin-2-yl)phenol, 3-(2-hydroxyphenyl)-3-phenyl-N,N-dipropylpropanamide as well as any derivatives of these compounds or analogues thereof. These compounds are commercially available through various sources.

Many of the compounds of the invention are currently prescribed for various disorders. For example, pyrimethamine is sold under the brand name Daraprim® for the treatment of protozoal infections including malaria and *Toxoplasma gondii* infections. Pimozide is sold as Orap to control tics caused by Tourette's disorder. Guanabenz Acetate is an alpha agonist used to treat high blood pressure. Alprenolol hydrochloride is a beta-receptor blocking agent used for the treatment of cardiac arrhythmias. Nifuroxazide is an orally administered anti-diarrheal that is sold under numerous brand names including, Akabar®, Antinal®, and Bacifurane. Fluoxetine hydrochloride is sold under the brand name Prozac® and is a psychotropic drug that is administered orally. Ifosfamide is an intravenous drug sold under the brand name Mitoxana® for the treatment of testicular cancer, cervical cancer, Ewing's sarcoma, and non-Hodgkin's lymphoma. Pyrvinium pamoate is sold under the brand name Vanquin for the treatment of pinworms. Moricizine hydrochloride is sold under the brand name Ethmozine as an orally active antiarrhythmic drug.

The compounds of the invention may be demonstrated to inhibit tumor cell proliferation, inhibit tumor cell number, cell transformation and tumorigenesis in vitro or in vivo using a variety of assays known in the art, or described herein. Such assays can use cells of a cancer cell line or cells from a patient in the presence and absence of the compound of interest. In one example, the cell has dysregulated STAT (e.g., enhanced STAT3 activation). The ability of a compound or a regimen of the invention to reduce the number of cancer cells or inhibit their proliferation can be assessed by: detecting the expression of antigens on cancer cells or detecting the proliferation of cancer. Techniques known to those of skilled in the art can be used for measuring these activities. For example, cellular proliferation can be assayed by $^3$H-thymidine incorporation assays and trypan blue cell counts. Antigen expression can be assayed, for example, by immunoassays including, but not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, flow cytometry and FACS analysis.

As described herein, since STAT3 can be inhibited in normal cells with relatively little toxicity, inhibitors of STAT3 were identified for rapid introduction into clinical trials. Using both chemical biology approaches and computational strategies, two anti-microbial drugs, pyrimethamine and atovaquone, were identified as blocking STAT3 transcriptional function at concentrations known to be achieved safely in humans continuously for months. As described in detail blow, both pyrimethamine and atovaquone slowed the growth of human and murine glioma cell lines and human glioma neurospheres. Furthermore, these STAT3 inhibitors altered expression of immune modulatory genes to make glioma cells more immunogenic. Unexpectedly, in an orthotopic murine glioma model, the combination of a STAT3 inhibitor and an inhibitor of the immune checkpoint PD-1 led to synergistic therapeutic effects.

To build on these findings, with the goal of initiating a clinical trial in patients, also described herein is the elucidation of the mechanism by which these STAT3 inhibitors alter expression of immune modulatory genes, determination of the key immune targets of STAT3, and identification of the optimal use of STAT3 inhibition with PD-1 blockade.

Immune Checkpoint Pathway

Immune checkpoint molecules are crucial for maintaining self-tolerance and modulating the duration and amplitude of physiological immune responses in peripheral tissues in order to minimize collateral tissue damage. Accordingly, immune checkpoint molecules made by some types of immune cells, e.g., CD4 T cells and CD8 T cells, and some cancer cells help keep immune responses in check and can keep T cells from killing cancer cells. Immune checkpoint molecules include, but are not limited to, programmed death 1 receptor (PD-1), cytotoxic T-lymphocyte antigen 4 (CTLA-4), B7H1, B7H4, OX-40, CD137, CD40, lymphocyte-activation gene 3 (LAG-3) and T-cell immunoglobulin and mucin-domain containing-3 (TIM-3), which directly inhibit immune cells.

Immune checkpoint inhibitors are molecules that block these immune checkpoint proteins. When immune checkpoint proteins are blocked by immune checkpoint inhibitors, the "brakes" on the immune system are released and T cells are able to identify and kill cancer cells. Immune checkpoint inhibitors include, but are not limited to, inhibitors of programmed death-ligand 1 (PD-L1), PD-L2, PD-1, CTLA-4, TIM-3, LAG-3, V-domain Ig suppressor of T cell activation (VISTA), T cell immunoreceptor with Ig and immunoreceptor tyrosine-based inhibition motif domains (TIGIT), and B and T Lymphocyte Attenuator (BTLA; CD272). Immune checkpoint inhibitors produce substantial clinical responses in some patients with metastatic melanomas (Hodi et al., 2010 N. Engl. J. Med., 363: 711-723; Brahmer et al., 2010 J. Clin. Oncol. Off. J. Am. Soc. Clin. Oncol., 28: 3167-3175; Brahmer et al., 2012 N. Engl. J. Med., 366: 2455-2465; Topalian et al., 2012 N. Engl. J. Med., 366: 2443-2454; and Hamid et al., 2013 N. Engl. J. Med., 369: 134-144).

Inhibition of an inhibitory molecule can be performed by inhibition at the DNA, RNA or protein level. In one aspect, an inhibitory nucleic acid (e.g., a dsRNA, siRNA or shRNA), can be used to inhibit expression of an immune checkpoint molecule. In another example, the inhibitor of an inhibitory signal is, a polypeptide, e.g., a soluble ligand, or an antibody or antigen-binding fragment thereof, that binds to the inhibitory molecule.

An exemplary human PD-L1 amino acid is set forth in SEQ ID NO: 15. An exemplary human PD-L1 nucleic acid is set forth in SEQ ID NO: 16. An exemplary human BTLA amino acid is set forth in SEQ ID NO: 19. An exemplary human PD-L1 nucleic acid is set forth in SEQ ID NO: 20.

```
An exemplary human PD-L2 amino acid sequence is set forth below (SEQ ID NO: 35;
GenBank Accession No: AAP13471, Version 1, incorporated herein by reference):
    1 miflllmlsl elqlhqiaal ftvtvpkely iiehgsnvtl ecnfdtgshv nlgaitaslq 61 kvendtsphr eratlleeql plgkasfhip qvqvrdegqy qciiiygvaw dykyltlkvk 121 asyrkinthi lkvpetdeve ltcqatgypl aevswpnvsv pantshsrtp eglyqvtsvl 181 rlkpppgrnf scvfwnthvr eltlasidlq sqmeprthpt wllhifipsc iiafifiatv 241 ialrkqlcqk lysskdttkr pvtttkrevn sai An exemplary human PD-L2 nucleic acid sequence is set forth below (SEQ ID NO: 36;
GenBank Accession No: NM_025239, Version 3, incorporated herein by reference):
    1 gcaaaccttc agctgaatga acaactttc ttctcttgaa tatatcttaa cgccaaattt 61 tgagtgcttt tttgttaccc atcctcatat gtcccagcta gaaagaatcc tgggttggag 121 ctactgcatg ttgattgttt tgttttcct tttggctgtt cattttggtg gctactataa 181 ggaaatctaa cacaaacagc aactgttttt tgttgtttac ttttgcatct ttacttgtgg 241 agctgtggca agtcctcata tcaaatacag aacatgatct tcctcctgct aatgttgagc 301 ctggaattgc agcttcacca gatagcagct ttattcacag tgacagtccc taaggaactg 361 tacataatag agcatggcag caatgtgacc ctggaatgca actttgacac tggaagtcat 421 gtgaaccttg gagcaataac agccagtttg caaaaggtgg aaaatgatac atccccacac 481 cgtgaaagag ccactttgct ggaggagcag ctgcccctag ggaaggcctc gttccacata 541 cctcaagtcc aagtgaggga cgaaggacag taccaatgca taatcatcta tggggtcgcc 601 tgggactaca gtacctgac tctgaaagtc aaagcttcct acaggaaaat aaacactcac 661 atcctaaagg ttccagaaac agatgaggta gagctcacct gccaggctac aggttatcct 721 ctggcagaag tatcctggcc aaacgtcagc gttcctgcca acaccagcca ctccaggacc 781 cctgaaggcc tctaccaggt caccagtgtt ctgcgcctaa agccacccc tggcagaaac 841 ttcagctgtg tgttctggaa tactcacgtg agggaactta ctttggccag cattgacctt 901 caaagtcaga tggaacccag gacccatcca acttggctgc ttcacatttt catcccttc 961 tgcatcattg ctttcatttt catagccaca gtgatagccc taagaaaaca actctgtcaa 1021 aagctgtatt cttcaaaaga cacaacaaaa agacctgtca ccacaacaaa gagggaagtg 1081 aacagtgcta tctgaacctg tggtcttggg agccagggtg acctgatatg acatctaaag 1141 aagcttctgg actctgaaca agaattcggt ggcctgcaga gcttgccatt tgcactttc 1201 aaatgccttt ggatgaccca gcactttaat ctgaaacctg caacaagact agccaacacc 1261 tggccatgaa acttgcccct tcactgatct ggactcacct ctggagccta tggctttaag 1321 caagcactac tgcactttac agaattaccc cactggatcc tggacccaca gaattccttc 1381 aggatccttc ttgctgccag actgaaagca aaaggaatta tttccctca agttttctaa
```

```
1441  gtgatttcca aaagcagagg tgtgtggaaa tttccagtaa cagaaacaga tgggttgcca 1501  atagagttat tttttatcta tagcttcctc tgggtactag aagaggctat tgagactatg 1561  agctcacaga cagggcttcg cacaaactca aatcataatt gacatgtttt atggattact 1621  ggaatcttga tagcataatg aagttgttct aattaacaga gagcatttaa atatacacta 1681  agtgcacaaa ttgtggagta aagtcatcaa gctctgtttt tgaggtctaa gtcacaaagc 1741  atttgtttta acctgtaatg gcaccatgtt taatggtggt ttttttttg aactacatct 1801  ttcctttaaa aattattggt ttcttttat ttgtttttac cttagaaatc aattatatac 1861  agtcaaaaat atttgatatg ctcatacgtt gtatctgcag caatttcaga taagtagcta 1921  aaatggccaa agccccaaac taagcctcct tttctggccc tcaatatgac tttaaatttg 1981  acttttcagt gcctcagttt gcacatctgt aatacagcaa tgctaagtag tcaaggcctt 2041  tgataattgg cactatggaa atcctgcaag atcccactac atatgtgtgg agcagaaggg 2101  taactcggct acagtaacag cttaattttg ttaaatttgt tctttatact ggagccatga 2161  agctcagagc attagctgac ccttgaacta ttcaaatggg cacattagct agtataacag 2221  acttacatag gtgggcctaa agcaagctcc ttaactgagc aaaatttggg gcttatgaga 2281  atgaaagggt gtgaaattga ctaacagaca aatcatacat ctcagtttct caattctcat 2341  gtaaatcaga gaatgccttt aagaataaaa actcaattgt tattcttcaa cgttctttat 2401  atattctact tttgggta
```

An exemplary human CTLA4 amino acid sequence is set forth below (SEQ ID NO: 37; GenBank Accession No: AAL07473.1, Version 1, incorporated herein by reference):

```
  1  maclgfqrhk aqlnlatrtw pctllffllf ipvfckamhv agpavvlass rgiasfvcey 61  aspgkatevr vtvlrqadsq vtevcaatym mgneltfldd sictgtssgn qvnitigglr 121  amdtglyick velmyppyy lgigngtqiy vidpepcpds dfllwilaav ssglffysfl 181  ltavslskml kkrsplttgv yvkmpptepe cekqfqpyfi pin
```

An exemplary human CTLA4 nucleic acid sequence is set forth below (SEQ ID NO: 38; GenBank Accession No: AF414120.1, Version 1, incorporated herein by reference):

```
  1  cttctgtgtg tgcacatgtg taatacatat ctgggatcaa agctatctat ataaagtcct 61  tgattctgtg tgggttcaaa cacatttcaa agcttcagga tcctgaaagg ttttgctcta 121  cttcctgaag acctgaacac cgctcccata aagccatggc ttgccttgga tttcagcggc 181  acaaggctca gctgaacctg gctaccagga cctggccctg cactctcctg ttttttcttc 241  tcttcatccc tgtcttctgc aaagcaatgc acgtggccca gcctgctgtg gtactggcca 301  gcagccgagg catcgccagc tttgtgtgtg agtatgcatc tccaggcaaa gccactgagg 361  tccgggtgac agtgcttcgg caggctgaca gccaggtgac tgaagtctgt gcggcaacct 421  acatgatggg gaatgagttg accttcctag atgattccat ctgcacgggc acctccagtg 481  gaaatcaagt gaacctcact atccaaggac tgagggccat ggacacggga ctctacatct 541  gcaaggtgga gctcatgtac ccaccgccat actacctggg cataggcaac ggaacccaga 601  tttatgtaat tgatccagaa ccgtgcccag attctgactt cctcctctgg atccttgcag 661  cagttagttc ggggttgttt ttttatagct ttctcctcac agctgttct tgagcaaaa 721  tgctaaagaa aagaagccct cttacaacag gggtctatgt gaaaatgccc caacagagc 781  cagaatgtga aaagcaattt cagccttatt ttattcccat caattgagaa accattatga 841  agaagagagt ccatatttca atttccaaga gctgaggcaa ttctaacttt tttgctatcc 901  agctattttt atttgtttgt gcatttgggg ggaattcatc tctctttaat ataaagttgg 961  atgcggaacc caaattacgt gtactacaat ttaaagcaaa ggagtagaaa gacagagctg
```

```
-continued
1021  ggatgtttct gtcacatcag ctccactttc agtgaaagca tcacttggga ttaatatggg 1081  gatgcagcat tatgatgtgg gtcaaggaat taagttaggg aatggcacag cccaaagaag 1141  gaaaaggcag ggagcgaggg agaagactat attgtacaca ccttatattt acgtatgaga 1201  cgtttatagc cgaaatgatc ttttcaagtt aaattttatg ccttttattt cttaaacaaa 1261  tgtatgatta catcaaggct tcaaaaatac tcacatggct atgttttagc cagtgatgct 1321  aaaggttgta ttgcatatat acatatatat atatatatat atatatatat atatatatat 1381  atatatatat tttaatttga tagtattgtg catagagcca cgtatgtttt tgtgtatttg 1441  ttaatggttt gaatataaac actatatggc agtgtctttc caccttgggg cccagggaag 1501  ttttgtggag gagctcagga cactaataca ccaggtagaa cacaaggtca tttgctaact 1561  agcttggaaa ctggatgagg tcatagcagt gcttgattgc gtggaattgt gctgagttgg 1621  tgttgacatg tgctttgggg cttttacacc agttcctttc aatggtttgc aaggaagcca 1681  cagctggtgg tatctgagtt gacttgacag aacactgtct tgaagacaat ggcttactcc 1741  aggagaccca caggtatgac cttctaggaa gctccagttc gatgggccca attcttacaa 1801  acatgtggtt aatgccatgg acagaagaag gcagcaggtg gcagaatggg gtgcatgaag 1861  gtttctgaaa attaacactg cttgtgtttt taactcaata ttttccatga aaatgcaaca 1921  acatgtataa tattttttaat taaataaaaa tctgtggtgg tcgttttaaa aaaaaaaaa 1981  aaaaaaaaaa aaaaaaaaaa aaaaaaaaaa aaaaaaaaaa aaaaa
```

An exemplary human TIM-3 amino acid sequence is set forth below (SEQ ID NO: 39; GenBank Accession No: AF066593, Version 1, incorporated herein by reference):

```
  1  mfshlpfdcv llllllllltr sseveyraev gqnaylpcfy tpaapgnlvp vcwgkgacpv 61  fecgnvvlrt derdvnywts rywlngdfrk gdvsltienv tladsgiycc riqipgimnd 121  ekfnlklvik pakvtpaptl qrdftaafpr mlttrghgpa etqtlgslpd inltqistla 181  nelrdsrlan dlrdsgatir igiyigagic aglalalifg alifkwyshs kekiqnlsli 241  slanlppsgl anavaegirs eeniytieen vyeveepney ycyvssrqqp sqplgcrfam 301  p
```

An exemplary human TIM-3 nucleic acid sequence is set forth below (SEQ ID NO: 40; GenBank Accession No: JX049979, Version 1, incorporated herein by reference):

```
  1  atgttttcac atcttccctt tgactgtgtc ctgctgctgc tgctgctact acttacaagg 61  tcctcagaag tggaatacag agcggaggtc ggtcagaatg cctatctgcc ctgcttctac 121  accccagccg ccccagggaa cctcgtgccc gtctgctggg gcaaaggagc ctgtcctgtg 181  tttgaatgtg gcaacgtggt gctcaggact gatgaaaggg atgtgaatta ttggacatcc 241  agatactggc taaatgggga tttccgcaaa ggagatgtgt ccctgaccat agagaatgtg 301  actctagcag acagtgggat ctactgctgc cggatccaaa tcccaggcat aatgaatgat 361  gaaaaattta acctgaagtt ggtcatcaaa ccagccaagg tcacccctgc accgactctg 421  cagagagact tcactgcagc cttttccaagg atgcttacca ccaggggaca tggcccagca 481  gagacacaga cactggggag cctccctgat ataaatctaa cacaaatatc cacattggcc 541  aatgagttac gggactctag attggccaat gacttacggg actctggagc aaccatcaga 601  ataggcatct acatcggagc agggatctgt gctgggctgg ctctggctct tatcttcggc 661  gctttaattt tcaaatggta ttctcatagc aaagagaaga tacagaattt aagcctcatc 721  tctttggcca acctccctcc ctcaggattg gcaaatgcag tagcagaggg aattcgctca 781  gaagaaaaca tctataccat tgaagagaac gtatatgaag tggaggagcc caatgagtat 841  tattgctatg tcagcagcag gcagcaaccc tcacaacctt ggggttgtcg cttttgcaatg 901  ccatag
```

An exemplary human LAG-3 amino acid sequence is set forth below (SEQ ID NO: 41; GenBank Accession No: CAA36243, Version 3, incorporated herein by reference):

```
  1 mweaqflgll flqplwvapv kplqpgaevp vvwaqegapa qlpcsptipl qdlsllrrag
 61 vtwqhqpdsg ppaaapghpl apgphpaaps swgprprryt vlsvgpgglr sgrlplqprv
121 qldergrqrg dfslwlrpar radageyraa vhlrdralsc rlrlrlgqas mtasppgslr
181 asdwvilncs fsrpdrpasv hwfrnrgqgr vpvresphhh laesflflpq vspmdsgpwg
241 ciltyrdgfn vsimynltvl glepptpltv yagagsrvgl pcrlpagvgt rsfltakwtp
301 pgggpdllvt gdngdftlrl edvsqaqagt ytchihlqeq qlnatvtlai itvtpksfgs
361 pgslgkllce vtpvsgqerf vwssldtpsq rsfsgpwlea qeaqllsqpw qcqlyqgerl
421 lgaavyftel sspgaqrsgr apgalpaghl llfltlgvls llllvtgafg fhlwrrqwrp
481 rrfsaleqgi hppqaqskie eleqepepep epepepepep epeql
```

An exemplary human LAG-3 nucleic acid sequence is set forth below (SEQ ID NO: 42; GenBank Accession No: NM_002286, Version 5, incorporated herein by reference):

```
   1 acagggtga aggcccagag accagcagaa cggcatccca gccacgacgg ccactttgct
  61 ctgtctgctc tccgccacgg ccctgctctg ttccctggga cacccccgcc cccacctcct
 121 caggctgcct gatctgccca gctttccagc tttcctctgg attccggcct ctggtcatcc
 181 ctccccaccc tctctccaag gccctctcct ggtctccctt cttctagaac cccttcctcc
 241 acctccctct ctgcagaact tctcctttac cccccacccc ccaccactgc cccctttcct
 301 tttctgacct ccttttggag ggctcagcgc tgcccagacc ataggagaga tgtgggaggc
 361 tcagttcctg ggcttgctgt ttctgcagcc gctttgggtg gctccagtga agcctctcca
 421 gccaggggct gaggtcccgg tggtgtgggc caggaggggg gctcctgccc agctcccctg
 481 cagccccaca atcccctcc aggatctcag ccttctgcga agagcagggg tcacttggca
 541 gcatcagcca gacagtggcc cgcccgctgc cgcccccggc catcccctgg ccccggccc
 601 tcacccggcg gcgccctcct cctgggggcc caggccccgc cgctacacgg tgctgagcgt
 661 gggtcccgga ggcctgcgca gcgggaggct gcccctgcag cccgcgtcc agctggatga
 721 gcgcggccgg cagcgcgggg acttctcgct atggctgcgc ccagcccggc gcgcggacgc
 781 cggcgagtac cgcgccgcgg tgcacctcag ggaccgcgcc ctctcctgcc gcctccgtct
 841 gcgcctgggc caggcctcga tgactgccag ccccccagga tctctcagag cctccgactg
 901 ggtcattttg aactgctcct tcagccgccc tgaccgccca gcctctgtgc attggttccg
 961 gaaccggggc cagggccgag tccctgtccg ggagtccccc catcaccact agcggaaag
1021 cttcctcttc ctgccccaag tcagccccat ggactctggg ccctggggct gcatcctcac
1081 ctacagagat ggcttcaacg tctccatcat gtataacctc actgttctgg gtctggagcc
1141 cccaactccc ttgacagtgt acgctgagc aggttccagg gtggggctgc cctgccgcct
1201 gcctgctggt gtggggaccc ggtctttcct cactgccaag tggactcctc ctggggagg
1261 ccctgacctc ctggtgactg agacaatgg cgactttacc cttcgactag aggatgtgag
1321 ccaggcccag gctgggacct acacctgcca tatccatctg caggaacagc agctcaatgc
1381 cactgtcaca ttggcaatca tcacagtgac tcccaaatcc tttgggtcac ctggatccct
1441 ggggaagctg ctttgtgagg tgactccagt atctggacaa gaacgctttg tgtggagctc
1501 tctggacacc ccatcccaga ggagtttctc aggaccttgg ctggaggcac aggaggccca
1561 gctcctttcc cagccttggc aatgccagct gtaccagggg gagaggcttc ttggagcagc
1621 agtgtactc acagagctgt ctagcccagg tgcccaacgc tctgggagag ccccaggtgc
1681 cctcccagca ggccacctcc tgctgtttct catccttggt gtcctttctc tgctcctttt
```

-continued

```
1741  ggtgactgga gcctttggct ttcacctttg gagaagacag tggcgaccaa gacgattttc 1801  tgccttagag caagggattc accctccgca ggctcagagc aagatagagg agctggagca 1861  agaaccggag ccggagccgg agccggaacc ggagcccgag cccgagcccg agccggagca 1921  gctctgacct ggagctgagg cagccagcag atctcagcag cccagtccaa ataaactccc 1981  tgtcagcagc aaaaa
```

An exemplary human VISTA amino acid sequence is set forth below (SEQ ID NO: 43; GenBank Accession No: NP_071436, Version 1, incorporated herein by reference):

```
  1  mgvptaleag swrwgsllfa lflaaslgpv aafkvatpys lyvcpegqnv tltcrllgpv 61  dkghdvtfyk twyrssrgev qtcserrpir nltfqdlhlh hgghqaants hdlaqrhgle 121  sasdhhgnfs itmrnltlld sglycclvve irhhhsehrv hgamelqvqt gkdapsncvv 181  ypsssqdsen itaaalatga civgilclpl illlvykqrq aasnrraqel vrmdsniqgi 241  enpgfeaspp aqgipeakvr hplsyvaqrq psesgrhlls epstplsppg pgdvffpsld 301  pvpdspnfev i
```

An exemplary human VISTA nucleic acid sequence is set forth below (SEQ ID NO: 44; GenBank Accession No: NM_022153, Version 1, incorporated herein by reference):

```
   1  ggggcgggt gcctggagca cggcgctggg gccgccgca cgctcactc gctcgcactc 61  agtcgcggga ggcttccccg cgccggccgc gtcccgcccg ctccccggca ccagaagttc 121  ctctgcgcgt ccgacggcga catgggcgtc cccacggccc tggaggccgg cagctggcgc 181  tggggatccc tgctcttcgc tctcttcctg gctgcgtccc taggtccggt ggcagccttc 241  aaggtcgcca cgccgtattc cctgtatgtc tgtccgagg ggcagaacgt caccctcacc 301  tgcaggctct gggccctgt ggacaaaggg cacgatgtga ccttctacaa gacgtggtac 361  cgcagctcga ggggcgaggt gcagacctgc tcagagcgcc ggcccatccg caacctcacg 421  ttccaggacc ttcacctgca ccatggaggc caccaggctg ccaacaccag ccacgacctg 481  gctcagcgcc acgggctgga gtcggcctcc gaccaccatg gcaacttctc catcaccatg 541  cgcaacctga ccctgctgga tagcggcctc tactgctgcc tggtggtgga gatcaggcac 601  caccactcgg agcacagggt ccatggtgcc atggagctgc aggtgcagac aggcaaagat 661  gcaccatcca actgtgtggt gtacccatcc tcctcccagg atagtgaaaa catcacggct 721  gcagccctgg ctacgggtgc ctgcatcgta ggaatcctct gcctccccct catcctgctc 781  ctggtctaca gcaaaggca ggcagcctcc aaccgccgtg cccaggagct ggtgcggatg 841  gacagcaaca ttcaagggat tgaaaacccc ggctttgaag cctcaccacc tgcccagggg 901  atacccgagg ccaaagtcag gcacccctg tcctatgtgg cccagcggca gccttctgag 961  tctgggcggc atctgctttc ggagcccagc acccccctgt ctcctccagg ccccggagac 1021  gtcttcttcc catccctgga ccctgtccct gactctccaa actttgaggt catctagccc 1081  agctggggga cagtgggctg ttgtggctgg gtctggggca ggtgcatttg agccagggct 1141  ggctctgtga gtggcctcct tggcctcggc cctggttccc tccctcctgc tctgggctca 1201  gatactgtga catcccagaa gcccagcccc tcaacccctc tggatgctac atggggatgc 1261  tggacggctc agccctgtt ccaaggattt tggggtgctg agattctccc ctagagacct 1321  gaaattcacc agctacagat gccaaatgac ttacatctta agaagtctca gaacgtccag 1381  cccttcagca gctctcgttc tgagacatga gccttgggat gtggcagcat cagtgggaca 1441  agatggacac tgggccaccc tcccaggcac cagacacagg gcacggtgga gagacttctc 1501  ccccgtgcc gccttggctc cccgttttg cccgaggctg ctcttctgtc agacttcctc 1561  tttgtaccac agtggctctg gggccaggcc tgcctgccca ctggccatcg ccaccttccc 1621  cagctgcctc ctaccagcag tttctctgaa gatctgtcaa caggttaagt caatctgggg
```

-continued

```
1681  cttccactgc ctgcattcca gtccccagag cttggtggtc ccgaaacggg aagtacatat
1741  tggggcatgg tggcctccgt gagcaaatgg tgtcttgggc aatctgaggc caggacagat
1801  gttgccccac ccactggaga tggtgctgag ggaggtgggt ggggccttct gggaaggtga
1861  gtggagaggg gcacctgccc cccgccctcc ccatcccta ctcccactgc tcagcgcggg
1921  ccattgcaag ggtgccacac aatgtcttgt ccaccctggg acacttctga gtatgaagcg
1981  ggatgctatt aaaaactaca tggggaaaca ggtgcaaacc ctggagatgg attgtaagag
2041  ccagtttaaa tctgcactct gctgctcctc ccccaccccc accttccact ccatacaatc
2101  tgggcctggt ggagtcttcg cttcagagcc attcggccag gtgcgggtga tgttcccatc
2161  tcctgcttgt gggcatgccc tggctttgtt tttatacaca taggcaaggt gagtcctctg
2221  tggaattgtg attgaaggat tttaaagcag gggaggagag taggggggcat ctctgtacac
2281  tctgggggta aacagggaa ggcagtgcct gagcatgggg acaggtgagg tggggctggg
2341  cagacccct gtagcgttta gcaggatggg ggccccaggt actgtggaga catagtcca
2401  gcctgggcat ttgtctccta gcagcctaca ctggctctgc tgagctgggc ctgggtgctg
2461  aaagccagga tttgggcta ggcgggaaga tgttcgccca attgcttggg gggttggggg
2521  gatggaaaag gggagcacct ctaggctgcc tggcagcagt gagccctggg cctgtggcta
2581  cagccaggga accccacctg gacacatggc cctgcttcta agcccccag ttaggcccaa
2641  aggaatggtc cactgagggc ctcctgctct gcctgggctg gccaggggc tttgaggaga
2701  gggtaaacat aggcccggag atggggctga cacctcgagt ggccagaata tgcccaaacc
2761  ccggcttctc ccttgtccct aggcagaggg gggtcccttc ttttgttccc tctggtcacc
2821  acaatgcttg atgccagctg ccataggaag agggtgctgg ctggccatgt tggcacacac
2881  ctgtcctccc agcactttgc agggctgagg tggaaggacc gcttaagccc aggtgttcaa
2941  ggctgctgtg agctgtgttc gagccactac actccagcct ggggacggag caaaactttg
3001  cctcaaaaca aattttaaaa agaaagaaag aaggaaagag ggtatgtttt tcacaattca
3061  tggggggcctg catggcagga gtggggacag gacacctgct gttcctggag tcgaaggaca
3121  agcccacagc ccagattccg gttctcccaa ctcaggaaga gcatgccctg ccctctgggg
3181  aggctggcct ggccccagcc ctcagctgct gaccttgagg cagagacaac ttctaagaat
3241  ttggctgcca gaccccaggc ctggctgctg ctgtgtggag agggaggcgg cccgcagcag
3301  aacagccacc gcacttcctc ctcagcttcc tctggtgcgg ccctgccctc tcttctctgg
3361  acccttttac aactgaacgc atctgggctt cgtggtttcc tgttttcagc gaaatttact
3421  ctgagctccc agttccatct tcatccatgg ccacaggccc tgcctacaac gcactaggga
3481  cgtccctccc tgctgctgct ggggagggc aggctgctgg agccgccctc tgagttgccc
3541  gggatggtag tgcctctgat gccagccctg gtggctgtgg gctggggtgc atgggagagc
3601  tgggtgcgag aacatggcgc ctccaggggg cggaggagc actaggggct ggggcaggag
3661  gctcctggag cgctggattc gtggcacagt ctgaggccct gagagggaaa tccatgcttt
3721  taagaactaa ttcattgtta ggagatcaat caggaattag gggccatctt acctatctcc
3781  tgacattcac agtttaatag agacttcctg cctttattcc ctcccaggga gaggctgaag
3841  gaatgaatt gaaagcacca tttgagggggt tttgctgaca cagcggggac tgctcagcac
3901  tccctaaaaa cacaccatgg aggccactgg tgactgctgg tgggcaggct ggccctgcct
3961  gggggagtcc gtggcgatgg gcgctgggt ggaggtgcag gagcccagg acctgctttt
4021  caaaagactt ctgcctgacc agagctccca ctacatgcag tggcccaggg cagaggggct
```

-continued

```
4081  gatacatggc cttttttcagg gggtgctcct cgcggggtgg acttgggagt gtgcagtggg 4141  acaggggggct gcaggggtcc tgccaccacc gagcaccaac ttggcccctg gggtcctgcc 4201  tcatgaatga ggccttcccc agggctggcc tgactgtgct gggggctggg ttaacgtttt 4261  ctcagggaac acaatgcac gaaagaggaa ctgggggttgc taaccaggat gctgggaaca 4321  aaggcctctt gaagcccagc cacagcccag ctgagcatga ggcccagccc atagacggca 4381  caggccacct ggcccattcc ctgggcattc cctgctttgc attgctgctt ctcttcaccc 4441  catggaggct atgtcaccct aactatcctg gaatgtgttg agagggattc tgaatgatca 4501  atatagcttg gtgagacagt gccgagatag atagccatgt ctgccttggg cacgggagag 4561  ggaagtggca gcatgcatgc tgtttcttgg cctttttctgt tagaatactt ggtgctttcc 4621  aacacacttt cacatgtgtt gtaacttgtt tgatccaccc ccttccctga aaatcctggg 4681  aggttttatt gctgccattt aacacagagg gcaatagagg ttctgaaagg tctgtgtctt 4741  gtcaaaacaa gtaaacggtg gaactacgac taaa
```

An exemplary human TIGIT amino acid sequence is set forth below (SEQ ID NO: 45;
GenBank Accession No: ACD74757, Version 1, incorporated herein by reference):

```
  1  mrwcilliwa qglrqaplas gmmtgtiett gnisaekggs iilqchlsst taqvtqvnwe 61  qqdqllaicn adlgwhisps fkdrvapgpg lgltlqsltv ndtgeyfciy htypdgtytg 121  riflevless vaehgarfqi pllgamaatl vvictavivv valtrkkkal rihsvegdlr 181  rksagqeews psapsppgsc vgaeaapagl cgeqrgedca elhdyfnvls yrslgncsff 241  tetg
```

An exemplary human TIGIT nucleic acid sequence is set forth below (SEQ ID NO: 46;
GenBank Accession No: NM_173799, Version 3, incorporated herein by reference):

```
   1  cgtcctatct gcagtcggct actttcagtg gcagaagagg ccacatctgc ttcctgtagg 61  ccctctgggc agaagcatgc gctggtgtct cctcctgatc tgggcccagg ggctgaggca 121  ggctcccctc gcctcaggaa tgatgacagg cacaatagaa acaacgggga acatttctgc 181  agagaaaggt ggctctatca tcttacaatg tcacctctcc tccaccacg cacaagtgac 241  ccaggtcaac tgggagcagc aggaccagct tctggccatt gtaatgctg acttggggtg 301  gcacatctcc ccatccttca aggatcgagt ggccccaggt cccggcctgg gcctcaccct 361  ccagtcgctg accgtgaacg atacagggga gtacttctgc atctatcaca cctaccctga 421  tgggacgtac actggggaaa tcttcctgga ggtcctagaa agctcagtgg ctgagcacgg 481  tgccaggttc cagattccat gcttggagc catggccgcg acgctggtgg tcatctgcac 541  agcagtcatc gtggtggtcg cgttgactag aaagaagaaa gccctcagaa tccattctgt 601  ggaaggtgac ctcaggagaa aatcagctgg acaggaggaa tggagcccca gtgctccctc 661  accccagga agctgtgtcc aggcagaagc tgcacctgct gggctctgtg gagagcagcg 721  gggagaggac tgtgccgagc tgcatgacta cttcaatgtc ctgagttaca agagcctggg 781  taactgcagc ttcttcacag agactggtta gcaaccagag gcatcttctg gaagatacac 841  ttttgtcttt gctattatag atgaatatat aagcagctgt actctccatc agtgctgcgt 901  gtgtgtgtgt gtgtgtatgt gtgtgtgtgt tcagttgagt gaataaatgt catcctcttc 961  tccatcttca tttccttggc cttttcgttc tattccattt tgcattatgg caggcctagg 1021  gtgagtaacg tggatcttga tcataaatgc aaaattaaaa aatatcttga cctggttttta 1081  aatctggcag tttgagcaga tcctatgtct ctgagagaca cattcctcat aatggccagc 1141  attttgggct acaaggtttt gtggttgatg atgaggatgg catgactgca gagccatcct 1201  catctcattt tttcacgtca ttttcagtaa ctttcactca ttcaaaggca ggttataagt 1261  aagtcctggt agcagcctct atggggagat ttgagagtga ctaaatcttg gtatctgccc
```

-continued

```
1321  tcaagaactt acagttaaat ggggagacaa tgttgtcatg aaaaggtatt atagtaagga 1381  gagaaggaga catacacagg ccttcaggaa gagacgacag tttggggtga ggtagttggc 1441  ataggcttat ctgtgatgaa gtggcctggg agcaccaagg ggatgttgag gctagtctgg 1501  gaggagcagg agttttgtct agggaacttg taggaaattc ttggagctga aagtcccaca 1561  aagaaggccc tggcaccaag ggagtcagca aacttcagat tttattctct gggcaggcat 1621  ttcaagtttc cttttgctgt gacatactca tccattagac agcctgatac aggcctgtag 1681  cctcttccgg ccgtgtgtgc tggggaagcc ccaggaaacg cacatgccca cacagggagc 1741  caagtcgtag catttgggcc ttgatctacc ttttctgcat caatacactc ttgagccttt 1801  gaaaaaagaa cgtttcccac taaaaagaaa atgtggattt ttaaaatagg gactcttcct 1861  aggggaaaaa gggggctgg gagtgataga gggtttaaaa aataaacacc ttcaaactaa 1921  cttcttcgaa cccttttatt cactccctga cgactttgtg ctggggttgg ggtaactgaa 1981  ccgcttattt ctgtttaatt gcattcaggc tggatcttag aagactttta tccttccacc 2041  atctctctca gaggaatgag cggggaggtt ggatttactg gtgactgatt ttctttcatg 2101  ggccaaggaa ctgaaagaga atgtgaagca aggttgtgtc ttgcgcatgg ttaaaaataa 2161  agcattgtcc tgcttcctaa gacttagact ggggttgaca attgtttttag caacaagaca 2221  attcaactat ttctcctagg atttttatta ttattatttt ttcactttc taccaaatgg 2281  gttacatagg aagaatgaac tgaaatctgt ccagagctcc aagtcctttg gaagaaagat 2341  tagatgaacg taaaaatgtt gttgtttgct gtggcagttt acagcatttt tcttgcaaaa 2401  ttagtgcaaa tctgttggaa atagaacaca attcacaaat tggaagtgaa ctaaaatgta 2461  atgacgaaaa gggagtagtg ttttgatttg gaggaggtgt atattcggca gaggttggac 2521  tgagagttgg gtgttattta acataattat ggtaattggg aaacatttat aaacactatt 2581  gggatggtga taaaatacaa aagggcctat agatgttaga aatgggtcag gttactgaaa 2641  tgggattcaa tttgaaaaaa attttttaa atagaactca ctgaactaga ttctcctctg 2701  agaaccagag aagaccattt catagttgga ttcctggaga catgcgctat ccaccacgta 2761  gccactttcc acatgtggcc atcaaccact taagatgggg ttagtttaaa tcaagatgtg 2821  ctgttataat tggtataagc ataaaatcac actagattct ggagatttaa tatgaataat 2881  aagaatacta tttcagtagt tttggtatat tgtgtgtcaa aaatgataat attttggatg 2941  tattgggtga aataaaatat taacattaaa aaaaaaaa
```

Hyperproliferative Disorders/Neoplasias

Although STAT-3 inhibitors may be useful to treat any hyperproliferative disorder, it is contemplated that the methods described herein are particularly useful when the individual has a hyperproliferative disorder characterized by an elevated STAT3 activity, e.g., a neoplasia.

Hyperproliferative disorders include cancerous disease states. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

The compounds described herein, e.g., a combination of a STAT3 inhibitor and an immune checkpoint inhibitor, can be used to treat or prevent a variety of hyperproliferative disorders. In some cases, the compounds of the invention are used to treat a cancer with elevated STAT3 activity (e.g., breast cancer, colon cancer and prostate cancer). For example, the invention is used to treat a solid tumor. In another aspect, the solid tumor is breast cancer, melanoma, colon cancer, ovarian cancer, pancreatic cancer, lung cancer, hepatic cancer, head and neck cancer, prostate cancer and brain cancer. In another example, the hyperproliferative disorder is a hematological cancer such as leukemia or multiple myeloma. Leukemia includes acute lymphoblastic leukemia, acute myelogenous leukemia, chronic myelogenous leukemia, Hodgkin's disease, non-Hodgkin's lymphoma, T-cell lymphoma, B-cell lymphoma and chronic lymphocytic leukemia. The described herein are also used to treat additional hyperproliferative disorders including but not limited to, cancer of the head, neck, eye, skin, mouth, throat, esophagus, chest, bone, lung, colon, sigmoid, rectum, stomach, prostate, ovary, testicle, kidney, liver, pancreas, brain, intestine, heart or adrenals (for a review of such disorders, see Fishman et al., 1985, Medicine, 2d Ed., J.B. Lippincott Co., Philadelphia, incorporated herein by reference).

The medical practitioner can diagnose the patient using any of the conventional cancer screening methods including, but not limited to physical examination (e.g., prostate examination, breast examination, lymph nodes examination, abdominal examination, skin surveillance), visual methods (e.g., colonoscopy, bronchoscopy, endoscopy), PAP smear analyses (cervical cancer), stool guaiac analyses, blood tests (e.g., complete blood count (CBC) test), blood chemistries including liver function tests, prostate specific antigen (PSA) test, carcinoembryonic antigen (CEA) test, cancer antigen (CA)-125 test, alpha-fetoprotein (AFP)), karyotyping analyses, bone marrow analyses (e.g., in cases of hematological malignancies), histology, cytology, a sputum analysis and imaging methods (e.g., computed tomography (CT), magnetic resonance imaging (MRI), ultrasound, X-ray imaging, mammography imaging, bone scans).

Administration of STAT Inhibitors and Immune Checkpoint Inhibitors

Hyperproliferative disorders, including, but not limited to cancer, neoplasms, tumors, metastases, or any disease or disorder characterized by uncontrolled cell growth as known in the art and described herein, can be treated, suppressed, delayed, managed, inhibited or prevented by administering to a subject in need thereof a prophylactically effective regimen or a therapeutically effective regimen, the regimen comprising administering to the patient a compound of the invention, e.g., a combination of a STAT3 inhibitor and an immune checkpoint inhibitor. The invention as it applies to cancer encompasses the treatment, suppression, delaying, management, inhibiting of growth and/or progression, and prevention of cancer or neoplastic disease as described herein.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient a compound of the invention or a composition of the invention, e.g., a combination of a STAT3 inhibitor and an immune checkpoint inhibitor, wherein the patient has been diagnosed with cancer. The amount of a compound of the invention used in the prophylactic and/or therapeutic regimens which will be effective in the prevention, treatment, and/or management of cancer can be based on the currently prescribed dosage of the compound as well as assessed by methods disclosed herein.

In one example, the cancer is a hematologic cancer. For instance, the cancer is leukemia, lymphoma or myeloma. In another example, the cancer is a solid tumor. In some cases, the patient has undergone a primary therapy to reduce the bulk of a solid tumor prior to therapy with the compositions and methods described herein. For example, the primary therapy to reduce the tumor bulk size is a therapy other than a compound or composition of the invention. For example, the solid tumor is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, embryonal brain tumor, PNET, or choroid plexus tumor.

In one aspect, the patient has received or is receiving another therapy. In another aspect, the patient has not previously received a therapy for the prevention, treatment, and/or management of the cancer.

Another aspect of the invention relates to a method of preventing, treating, and/or managing cancer, wherein the patient received another therapy. In some embodiments, the prior therapy is, for example, chemotherapy, radioimmunotherapy, toxin therapy, prodrug-activating enzyme therapy, antibody therapy, surgical therapy, immunotherapy, radiation therapy, targeted therapy or any combination thereof. In some embodiments, the prior therapy has failed in the patient. In some cases, the therapeutically effective regimen comprising administration of a composition of the invention is administered to the patient immediately after patient has undergone the prior therapy. For instance, in certain cases, the outcome of the prior therapy may be unknown before the patient is administered a compound of the invention.

In some cases, the therapeutic regimen results in a reduction in the cancer cell population in the patient. In one example, the patient undergoing the therapeutic regimen is monitored to determine whether the regimen has resulted in a reduction in the cancer cell population in the patient. Typically, the monitoring of the cancer cell population is conducted by detecting the number or amount of cancer cells in a specimen extracted from the patient. Methods of detecting the number or amount of cancer cells in a specimen are known in the art. This monitoring step is typically performed at least 1, 2, 4, 6, 8, 10, 12, 14, 15, 16, 18, 20, or 30 days after the patient begins receiving the regimen.

In one aspect, the specimen may be a blood specimen, wherein the number or amount of cancer cells per unit of volume (e.g., 1 mL) or other measured unit (e.g., per unit field in the case of a histological analysis) is quantitated. The cancer cell population, in certain embodiments, can be determined as a percentage of the total blood cells. In other cases, the specimen extracted from the patient is a tissue specimen (e.g., a biopsy extracted from suspected cancerous tissue), where the number or amount of cancer cells can be measured, for example, on the basis of the number or amount of cancer cells per unit weight of the tissue. The number or amount of cancer cells in the extracted specimen can be compared with the numbers or amounts of cancer cells measured in reference samples to assess the efficacy of the regimen and amelioration of the cancer under therapy. For example, the reference sample is a specimen extracted from the patient undergoing therapy, wherein the specimen from the patient is extracted at an earlier time point (e.g., prior to receiving the regimen, as a baseline reference sample, or at an earlier time point while receiving the therapy). In another example, the reference sample is extracted from a healthy, noncancer-afflicted patient.

In other cases, the cancer cell population in the extracted specimen can be compared with a predetermined reference range. In a specific embodiment, the predetermined reference range is based on the number or amount of cancer cells obtained from a population(s) of patients suffering from the same type of cancer as the patient undergoing the therapy.

STAT3 and the Immune Response: Immune Cell Function, Tumor Immunogenicity, and Therapeutic Implications In physiological conditions, STAT3 phosphorylation and functional activation peak within 15-30 minutes following stimulation and return to basal state within 60-90 minutes. By contrast, in malignant conditions, continuous activation and phosphorylation of STAT3 is observed. For example, STAT3 is activated in hematologic malignancies, e.g., acute lymphoblastic leukemia, acute myelogenous leukemia, chronic myelogenous leukemia, chronic lymphocytic leukemia, non-Hodgkin lymphomas, Hodgkin lymphoma, and multiple myeloma, as well as in non-hematologic malignancies, e.g., breast cancer, melanoma, pancreatic cancer, lung cancer, colon cancer, ovary cancer, head and neck cancer, prostate cancer, and brain cancer.

STAT3 is frequently activated in tumor cells through autocrine and paracrine mechanisms. These mechanisms can also lead to STAT3 activation in infiltrating and surrounding immune cells. Sustained STAT3 activation in immune cells is generally immunosuppressive and results in 1) decreased antigen presentation by dendritic cells; and 2) decreased effector T cell function.

As described herein, STAT3 activation in the cancer cell is associated with decreased immunogenicity of the tumor. Accordingly, a STAT3 inhibitor, e.g., a small molecule inhibitor of STAT3, enhances both 1) the immunogenicity of tumor cells and 2) the responsiveness of the patient's immune system. The results presented herein demonstrate that this effect is particularly enhanced in combination with immune checkpoint inhibitors.

STAT3-Regulated Immunomodulatory Genes

Described herein is a gene signature of direct STAT3 targets comprised of 16 immunomodulatory genes. Exemplary genes are provided below.

```
An exemplary human inducible costimulator-ligand (Icos-L) amino acid sequence is set
forth below (SEQ ID NO: 1; GenBank Accession No: NP_001269981, Version 1,
incorporated herein by reference):
    1   mspagmlrgd fslrlfnvtp qdeqkfhclv lsqslgfqev lsvevtlhva anfsvpvvsa 61   phspsqdelt ftctsingyp rpnvywinkt dnslldqalq ndtvflnmrg lydvvsvlri 121   artpsvnigc cienvllqqn ltvgsqtgnd igerdkiten pvstgeknaa twsilavlcl 181   lvvvavaigw vcrdrclqhs yagawayspe teltghv An exemplary human Icos-L nucleic acid sequence is set forth below (SEQ ID NO: 2;
GenBank Accession No: NM_001283052, Version 1, incorporated herein by reference):
    1   gacacggctg cctccagcac accgcgcgct gggcgctcag agcctcgggc gcggcgggag 61   cgcagttaga gccgatctcc cgcgccccga ggttgctcct ctccgaggtc tcccgcggcc 121   caagttctcc gcgccccgag gtctccgcgc cccgaggtct ccgcggcccg aggtctccgc 181   ccgcaccatg cggctgggca gtcctggact gctcttcctg ctcttcagca gccttcgagc 241   tgaacagctc cttggaaaac gtggacagcc gctaccggaa ccgagccctg atgtcaccgg 301   ccggcatgct gcggggcgac ttctcccctgc gcttgttcaa cgtcaccccc caggacgagc 361   agaagtttca ctgcctggtg ttgagccaat ccctgggatt ccaggaggtt ttgagcgttg 421   aggttacact gcatgtggca gcaaacttca gcgtgcccgt cgtcagcgcc cccacagcc 481   cctcccagga tgagctcacc ttcacgtgta catccataaa cggctacccc aggcccaacg 541   tgtactggat caataagacg gacaacagcc tgctggacca ggctctgcag aatgacaccg 601   tcttcttgaa catgcggggc ttgtatgacg tggtcagcgt gctgaggatc gcacggaccc 661   ccagcgtgaa cattggctgc tgcatagaga acgtgcttct gcagcagaac ctgactgtcg 721   gcagccagac aggaaatgac atcggagaga gagacaagat cacagagaat ccagtcagta 781   ccggcgagaa aaacgcggcc acgtggagca tcctggctgt cctgtgcctg cttgtggtcg 841   tggcggtggc cataggctgg gtgtgcaggg accgatgcct ccaacacagc tatgcaggtg
```

-continued

```
 901   cctgggctgt gagtccggag acagagctca ctggccacgt ttgaccggag ctcaccgccc
 961   agagcgtgga cagggcttcc gtgagacgcc accgtgagag gccaggtggc agcttgagca
1021   tggactccca gactgcaggg gagcacttgg ggcagccccc agaaggacca ctgctggatc
1081   ccagggagaa cctgctggcg ttggctgtga tcctggaatg aggccctttc aaaagcgtca
1141   tccacaccaa aggcaaatgt ccccaagtga gtgggctccc cgctgtcact gccagtcacc
1201   cacaggaagg gactggtgat gggctgtctc tacccggagc gtgcgggatt cagcaccagg
1261   ctcttcccag taccccagac ccactgtggg tcttcccgtg ggatgcggga tcctgagacc
1321   gaagggtgtt tggtttaaaa agaagactgg gcgtccgctc ttccaggacg gcctctgtgc
1381   tgctggggtc acgcgaggct gtttgcaggg gacacggtca caggagctct tctgccctga
1441   acgctcccaa cctgcctccc gcccggaagc cacaggaccc actcatgtgt gtgcccacaa
1501   gtgtagttag ccgtccacac cgaggagccc ccggaagtcc ccactgggct tcagtgtcct
1561   ctgccacatt ccctgggagg aacaatgtcc ctcggctgtt ccggtgaaaa gttgagccac
1621   ctttggaaga cgcacgggtg gagtttgcca aagaaaggc tgtgccaggg ccgtgtttgg
1681   ctacaggggc tgccggggct cttggctctg cagcgagaaa gacacagccc agcagggctg
1741   gagacgccca tgtccagcag gcgcaggcct ggcaacacgg tccccagagt cctgagcagc
1801   agttaggtgc atggagaggg tatcacctgg tggccacagt ccccccttct acctcagcaa
1861   tgatccccaa agtgagaggt ggctcccccg gcccccacca ccctcagcag ccccacccca
1921   ctcaaccctg agggtcccca gggtcctgat gaagacctcc gaccccagcg ccaggctcct
1981   cggagcccaa cagtcccaag ggggcaggag acggggtggt ccagtgctga ggggtacagc
2041   cctgggccct gaccagcccc ggcacctgcc atgctggttc ccggaatgaa tcagctgctg
2101   actgtctcca gaagggctgg aaaggatgct gccaggtgac ccgaggtgca ctcgccccag
2161   ggagatggag tagacagcct ggcctggccc tcgggacaca ttgtctgccc cggggctatg
2221   ggcaaatgcc cctccttctt acttcccaga atccctgac attcccaggg tcagccagga
2281   cctgttacag ccctggtcac ttggaactga cagctgtgtg aggcctgcac ttctcagacc
2341   cagacttaga acaaaggag gagtgaggac tcaaggctac aatgaggttc cagtacttgt
2401   tacaagaaat tggttttctg caaaaaaagt ccctacctga gcctttaggt gaatgtggga
2461   tccactcccg cttttaacat gaaagcatta gaagatgtgt ggtgtttata aagaacagt
2521   tgtcatcacc gggcattgat tggcagggac aaggagctgc ttgggtgtgg aaagttgggg
2581   cgttggaaag tgggctgtgg tgcccatttg cagtgactgt gaagtgactc caggacggac
2641   ctgcggggggc acccagaggt cctaagcccc aggactgagg gtcgtgcatc accactcggg
2701   tgtcccggga ggtgccctgg gcccggggac ctcacaggca ggacggcgac actaatgcag
2761   ggagagggag tctggcccca gcttttccta tcagaggcga ttttccttca ccaggggatg
2821   ggcaggaaag aggcagggc cccagaagct tctgtccctc atgcctgagg cacggggga
2881   cacttggagg ctgctgtcac cactgtgcgt ccaaggccat gctctctgcg ggtcagtgcc
2941   tgagtctcgc ctccctgctg gtccctgaag cccccctcaga agccctgcct gtcacgtcgg
3001   catttgtgag acctaccctg taacgcctgc ccctctcagc ccaacatcag cttcctcttt
3061   ctcccttgct gtagacaggc tggattccag tgttgggaca gccatctcca gaaacctgac
3121   ttaagagagt aagatgcaaa tcgtgcctgt aaaaaaaaaa aaaaaaa
```

An exemplary human cluster of differentiation 70 (CD70) amino acid sequence is set forth below (SEQ ID NO: 3; GenBank Accession No: NP_001243, Version 1, incorporated herein by reference):

```
  1  mpeegsgcsv rrrpygcvlr aalvplvagl viclvvciqr faqaqqqlpl eslgwdvael 61  qlnhtgpqqd prlywqggpa lgrsflhgpe ldkgqlrihr dgiymvhiqv tlaicsstta 121  srhhpttlav gicspasrsi sllrlsfhqg ctiasqrltp largdtlctn ltgtllpsrn 181  tdetffgvqw vrp
```

An exemplary human CD70 nucleic acid sequence is set forth below (SEQ ID NO: 4; GenBank Accession No: NM_001252, Version 4, incorporated herein by reference):

```
  1  ccagagaggg gcaggctggt ccectgacag gttgaagcaa gtagacgccc aggagccccg 61  ggaggggget gcagtttcct tccttccttc tcggcagcgc tccgcgcccc catcgccect 121  cctgcgctag cggaggtgat cgccgcggcg atgccggagg agggttcggg ctgctcggtg 181  cggcgcaggc cctatgggtg cgtcctgcgg gctgctttgg tcccattggt cgcgggcttg 241  gtgatctgcc tcgtggtgtg catccagcgc ttcgcacagg ctcagcagca gctgccgctc 301  gagtcacttg gtgggacgt agctgagctg cagctgaatc acacaggacc tcagcaggac 361  cccaggctat actggcaggg gggcccagca ctggccgct ccttcctgca tggaccagag 421  ctggacaagg ggcagctacg tatccatcgt gatggcatct acatggtaca catccaggtg 481  acgctggcca tctgctcctc cacgacggcc tccaggcacc accccaccac cctggccgtg 541  ggaatctgct ctcccgcctc ccgtagcatc agcctgctgc gtctcagctt ccaccaaggt 601  tgtaccattg cctcccagcg cctgacgccc tggcccgag ggacacact ctgcaccaac 661  ctcactggga cacttttgcc ttcccgaaac actgatgaga ccttctttgg agtgcagtgg 721  gtgcgccct gaccactgct gctgattagg gttttttaaa ttttattta ttttatttaa 781  gttcaagaga aaaagtgtac acacaggggc caccegggt tggggtggga gtgtggtggg 841  gggtagtggt ggcaggacaa gagaaggcat tgagctttt ctttcatttt cctattaaaa 901  aatacaaaaa tca
```

An exemplary human tumor necrosis factor-like protein 1A (TL1A) amino acid sequence is set forth below (SEQ ID NO: 5; GenBank Accession No: AAI04464, Version 1, incorporated herein by reference):

```
  1  maedlglsfg etasvemlpe hgscrpkars ssarwaltcc lvllpflagl ttyllvsqlr 61  aqgeacvqfq alkgqefaps hqqvyaplra dgdkprahlt vvrqtptqhf knqfpalhwe 121  helglaftkn rmnytnkfll ipesgdyfiy sqvtfrgmts ecseirqagr pnkpdsitvv 181  itkvtdsype ptqllmgtks vcevgsnwfq piylgamfsl qegdklmvnv sdislvdytk 241  edktffgafl l
```

An exemplary human TL1A nucleic acid sequence is set forth below (SEQ ID NO: 6; GenBank Accession No: AF520785, Version 1, incorporated herein by reference):

```
  1  gagagggaaa agggaaggag gagactgagt gattaagtca cccactgtga agagctggtc 61  ttctatttaa tgggggctct ctctgcccag gagtcagagg tgcctccagg agcagcagga 121  gcatggccga ggatctggga ctgagctttg ggaaacagc cagtgtggaa atgctgccag 181  agcacggcag ctgcaggccc aaggccagga gcagcagcgc acgctgggct ctcacctgct 241  gcctggtgtt gctccccttc cttgcaggac tcaccacata cctgcttgtc agccagctcc 301  gggcccaggg agaggcctgt gtgcagttcc aggctctaaa aggacaggag tttgcacctt 361  cacatcagca gtttatgca cctcttagag cagacggaga taagccaagg gcacacctga 421  cagttgtgag acaaactccc acacagcact ttaaaaatca gttcccagct ctgcactggg 481  aacatgaact aggcctggcc ttcaccaaga accgaatgaa ctataccaac aaattcctgc 541  tgatcccaga gtcgggagac tacttcattt actcccaggt cacattccgt gggatgacct
```

-continued

```
  601  ctgagtgcag tgaaatcaga caagcaggcc gaccaaacaa gccagactcc atcactgtgg
  661  tcatcaccaa ggtaacagac agctaccctg agccaaccca gctcctcatg gggaccaagt
  721  ctgtatgcga agtaggtagc aactggttcc agcccatcta cctcggagcc atgttctcct
  781  tgcaagaagg ggacaagcta atggtgaacg tcagtgacat ctctttggtg gattacacaa
  841  aagaagataa aaccttcttt ggagccttct tactatagga ggagagcaaa tatcattata
  901  tgaaagtcct ctgccaccga gttcctaatt ttctttgttc aaatgtaatt ataaccaggg
  961  gttttcttgg ggccgggagt aggggggcatt ccacagggac aacggtttag ctatgaaatt
 1021  tggggcccaa aatttcacac ttcatgtgcc ttactgatga gagtactaac tggaaaaggc
 1081  tgaagagagc aaatatatta ttaagatggg ttggaggatt ggcgagtttc taaatattaa
 1141  gacactgatc actaaatgaa tggatgatct actcgggtca ggattgaaag agaaatattt
 1201  caacacctcc ctgctataca atggtcacca gtggtccagt tattgttcaa tttgatcata
 1261  aatttgcttc aattcaggag ctttgaagga agtccaagga aagctctaga aaacagtata
 1321  aactttcaga ggcaaaatcc ttcaccaatt tttccacata ctttcatgcc ttgcctaaaa
 1381  aaaatgaaaa gagagttggt atgtctcatg aatgttcaca cagaaggagt tggttttcat
 1441  gtcatctaca gcatatgaga aaagctacct ttcttttgat tatgtacaca gatatctaaa
 1501  taaggaagta tgagtttcac atgtatatca aaaatacaac agttgcttgt attcagtaga
 1561  gttttcttgc ccacctattt tgtgctgggt tctaccttaa cccagaagac actatgaaaa
 1621  acaagacaga ctccactcaa aatttatatg aacaccacta gatacttcct gatcaaacat
 1681  cagtcaacat actctaaaga ataactccaa gtcttggcca ggcgcagtgg ctcacacctg
 1741  taatcccaac actttgggag gccaaggtgg gtggatcatc taaggccggg agttcaagac
 1801  cagcctgacc aacgtggaga accccatct ctactaaaaa tacaaaatta gccgggcgtg
 1861  gtagcgcatg gctgtaatcc tggctactca ggaggccgag gcagaagaat tgcttgaact
 1921  ggggaggcag aggttgcggt gagcccagat cgcgccattg cactccagcc tgggtaacaa
 1981  gagcaaaact ctgtccaaaa aaaaaaaaaa aaaaaa
```

An exemplary human OX40-L amino acid sequence is set forth below (SEQ ID NO: 7; GenBank Accession No: BAB18304, Version 1, incorporated herein by reference):

```
  1  mervqpleen vgnaarprfe rnklllvasv iqglglllcf tyiclhfsal qvshrypriq
 61  sikvqft
```

An exemplary human OX40-L nucleic acid sequence is set forth below (SEQ ID NO: 8; GenBank Accession No: AB042988, Version 2, incorporated herein by reference):

```
  1  atcgcacgtt cccctttcc atatcttcat cttccctcta cccagattgt gaagatggaa
 61  agggtccaac ccctggaaga gaatgtggga aatgcagcca ggccaagatt cgagaggaac
121  aagctattgc tggtggcctc tgtaattcag ggactggggc tgctcctgtg cttcacctac
181  atctgcctgc acttctctgc tcttcaggta agatgcacca ctgggcgctg ttttcccacc
241  agctcatgct gatggcagct nnnnnnnnnn nnnnnnnnnn nnnnnnnnnn nnnnnnnnnn
301  nnnnnnnnnn nnnnnnnnnn nnnnnnnnnn nnnnnnnnnn nnnnnnnnnn nnnnnnnnnn
361  caggctactg catttctgct tcactgttcc attaaatatg acttgcgaat tcatttgtt
421  catgtttttt tcctaagaat atgtctttct tcctccctca ggtatcacat cggtatcctc
481  gaattcaaag tatcaaagta caatttaccg gtaagtattg tcaaaagttt aattgattca
541  tattttgaa agaatcttct cttcagtctc ttaatttcct ctagaacaca agatctcttc
601  ttttcctaag ggaaggaatt aaattccaat taaatcccag aattgttgta gcctgc
```

An exemplary human 4-1BB ligand (4-1BBL) amino acid sequence is set forth below (SEQ ID NO: 9; GenBank Accession No: NP_003802, Version 1, incorporated herein by reference):

```
  1 meyasdasld peapwppapr aracrvlpwa lvaglllll laaacavfla cpwavsgara
 61 spgsaasprl regpelspdd paglldlrqg mfaqlvaqnv llidgplswy sdpglagvsl
121 tgglsykedt kelvvakagv yyvffqlelr rvvagegsgs vslalhlqpl rsaagaaala
181 ltvdlppass earnsafgfq grllhlsagq rlgvhlhtea rarhawqltq gatvlglfrv
241 tpeipaglps prse
```

An exemplary human 4-1BBL nucleic acid sequence is set forth below (SEQ ID NO: 10; GenBank Accession No: NM_003811, Version 3, incorporated herein by reference):

```
   1 aaaaagcggc gcgctgtgtc ttcccgcagt ctctcgtcat ggaatacgcc tctgacgctt
  61 cactggaccc cgaagccccg tggcctcccg cgcccgcgc tcgcgcctgc cgcgtactgc
 121 cttgggccct ggtcgcgggg ctgctgctgc tgctgctgct cgctgccgcc tgcgccgtct
 181 tcctcgcctg cccctgggcc gtgtccgggg ctcgcgcctc gcccggctcc gcggccagcc
 241 cgagactccg cgagggtccc gagctttcgc ccgacgatcc cgccggcctc ttggacctgc
 301 ggcagggcat gtttgcgcag ctggtggccc aaaatgttct gctgatcgat gggcccctga
 361 gctggtacag tgacccaggc ctggcaggcg tgtccctgac ggggggcctg agctacaaag
 421 aggacacgaa ggagctggtg gtggccaagg ctggagtcta ctatgtcttc tttcaactag
 481 agctgcggcg cgtggtggcc ggcgagggct caggctccgt ttcacttgcg ctgcacctgc
 541 agccactgcg ctctgctgct ggggccgccg ccctggcttt gaccgtggac ctgccacccg
 601 cctcctccga ggctcggaac tcggccttcg gtttccaggg ccgcttgctg cacctgagtg
 661 ccggccagcg cctgggcgtc catcttcaca ctgaggccag gcacgccat gcctggcagc
 721 ttacccaggg cgccacagtc ttgggactct ccgggtgac cccgaaaatc ccagccggac
 781 tccttcacc gaggtcggaa taacgtccag cctgggtgca gcccacctgg acagagtccg
 841 aatcctactc catccttcat ggagaccct ggtgctgggt ccctgctgct ttctctacct
 901 caaggggctt ggcaggggtc cctgctgctg acctccctt gaggaccctc ctcacccact
 961 ccttccccaa gttggacctt gatatttatt ctgagcctga gctcagataa tatattatat
1021 atattatata tatatatata tttctattta agaggatcc tgagtttgtg aatggacttt
1081 tttagaggag ttgtttggg ggggggggg tcttcgacat tgccgaggct ggtcttgaac
1141 tcctggactt agacgatcct cctgcctcag cctcccaagc aactgggatt catccttct
1201 attaattcat tgtacttatt tgcttatttg tgtgtattga gcatctgtaa tgtgccagca
1261 ttgtgcccag gctaggggc tatagaaaca tctagaaata gactgaaaga aaatctgagt
1321 tatggtaata cgtgaggaat ttaaagactc atccccagcc tccacctcct gtgtgatact
1381 tggggctag cttttttctt tctttctttt ttttgagatg gtcttgttct gtcaaccagg
1441 ctagaatgca gcggtgcaat catgagtcaa tgcagcctcc agcctcgacc tcccgaggct
1501 caggtgatcc tcccatctca gcctctcgag tagctgggac cacagttgtg tgccaccaca
1561 cttggctaac tttttaattt ttttgcggag acggtattgc tatgttgcca aggttgttta
1621 catgccagta caatttataa taaacactca tttttcctcc ctctgaaaaa aaaaaaaaa
```

An exemplary human glucocorticoid-induced TNFR-related protein ligand (GITR-L) amino acid sequence is set forth below (SEQ ID NO: 11; GenBank Accession No: NP_899247, Version 3, incorporated herein by reference):

```
  1 meemplress pqraerckks wllcivalll mllcslgtli ytslkptaie scmvkfelss
 61 skwhmtspkp hcvnttsdgk lkilqsgtyl iygqvipvdk kyikdnapfv vqiykkndvl
121 qtlmndfqil piggvyelha gdniylkfns kdhiqktnty wgiilmpdlp fis
```

-continued

An exemplary human GITR-L nucleic acid sequence is set forth below (SEQ ID NO: 12; GenBank Accession No: NM_183391, Version 3, incorporated herein by reference):

```
   1 ttgtgggtat ctgctttccc cagttctcat tccatcagag aacgagttct agcctcatgg
  61 aggaaatgcc tttgagagaa tcaagtcctc aaagggcaga gaggtgcaag aagtcatggc
 121 tcttgtgcat agtggctctg ttactgatgt tgctctgttc tttgggtaca ctgatctata
 181 cttcactcaa gccaactgcc atcgagtcct gcatggttaa gtttgaacta tcatcctcaa
 241 aatggcacat gacatctccc aaacctcact gtgtgaatac gacatctgat gggaagctga
 301 agatactgca gagtggcaca tatttaatct acggccaagt gattcctgtg ataagaaat
 361 acataaaaga caatgccccc ttcgtagtac agatatataa aaagaatgat gtcctacaaa
 421 ctctaatgaa tgattttcaa atcttgccta taggaggggt ttatgaactg catgctggag
 481 ataacatata tctgaagttc aactctaaag accatattca gaaaactaac acatactggg
 541 ggatcatctt aatgcctgat ctaccattca tctcttagag attgggtttg gtctcctcat
 601 cttcttcttt gtatcccgag atgctggtgg gtgggttgga ggggatgat tgatggcaat
 661 gcacacagtt tgtgagggct tacaaattga cacaatcaga gcctcttggc atataaaatt
 721 ttagccctca tatctgtctg aagaggactc agcaaatggg ccaatcccta tgttgggtc
 781 tgcaaatgga cttgtacaat ccatgataaa aaggagtatg ggccacagaa gacagaaact
 841 cttccaaaga atgtctttct aaccttgatc cctgggtaga atgagatcct gtttccatgg
 901 gagtcttact tggcttgcaa aaagggtgt agggcagtag cttggccttt tttccatcat
 961 aatttccttg agctgtttta ccttaatccc tccaaactct caccttctga gagcctccta
1021 atgaaacatt gttagactgg tggggtggcc aagacatgcc aacaacaccc ttctttagag
1081 gtggtgtttt tagaggacag agaacattat gaagcctaga gcagcagagg tcaagatgcc
1141 acgaaatgga attgatctgg gaatttttt ttttttttcat tctcaggatg caggttcatt
1201 ctgaactttc ccctaggcct tcattgcttt tgtgtgtatg tgtgcataaa ttctgcaaat
1261 agaaaaatga gagtttgcac cagtactcac tagatttaac accagaaagt ggtactttc
1321 tggctgtatt atgccatgat agcacatttt ctgttggtgt tccctaactg acaagtataa
1381 cagttttcct aaaccacaca acaatgctat gatgttaatg gggtagatat ttttggaaaa
1441 aaattgcaca gtgagaacat gggtagatga accctaagac tcttacctca attcagaact
1501 cgcaaggagt taagtgagtg gggtcttcat tagaccattc acatggtctc tgctttgaaa
1561 ctggcgttgc tactgtctca ttatacatca ctaaaatgga attaactcaa ctttgaaatg
1621 gatgcatcga ctttaccccca aggtgtccag aatgaagcta caagacttt accagcagtc
1681 attttccttt tgcctggagc aagaagatcc aggatactgt tggaagagtt catctcactc
1741 aaccatgctg actttccaaa gtaataatga acatttgtgt tcaaattttg gattctgtta
1801 aatttagcca gcttgtgagt tcttgtcgaa aagtatttta aaccaattta cactatttat
1861 gggtatttgt gaaaagctat atagtgatat tttatatata actaatttaa aatatttta
1921 ttttatgtaa caaaaatact ataggctaag ctatttcttc ttattttttt atgaatactt
1981 gctgaattgc catagggcac aaagactctt ctgtttgcat atcttctcag gaaattaaaa
2041 ttgtatcaca tgtatttata agaa
```

An exemplary human cluster of differentiation 40 (CD40) amino acid sequence is set forth below (SEQ ID NO: 13; GenBank Accession No: AAH64518, Version 1, incorporated herein by reference):

```
   1 mvrlplqcvl wgclltavhp epptacrekq ylinsqccsl cqpgqklvsd cteftetecl
  61 pcgesefldt wnrethfhqh kycdpnlglr vqqkgtsetd tictceegwh ctseacescv
 121 lhrscspgfg vkqidicqph fpkdrglnll m
```

An exemplary human CD40 nucleic acid sequence is set forth below (SEQ ID NO: 14; GenBank Accession No: NM_001250, Version 5, incorporated herein by reference):

```
   1 tttcctgggc ggggccaagg ctggggcagg ggagtcagca gaggcctcgc tcgggcgccc
  61 agtggtcctg ccgcctggtc tcacctcgct atggttcgtc tgcctctgca gtgcgtcctc
 121 tggggctgct tgctgaccgc tgtccatcca gaaccaccca ctgcatgcag agaaaaacag
 181 tacctaataa acagtcagtg ctgttctttg tgccagccag acagaaaact ggtgagtgac
 241 tgcacagagt tcactgaaac ggaatgcctt ccttgcggtg aaagcgaatt cctagacacc
 301 tggaacagag agacacactg ccaccagcac aaatactgcg accccaacct agggcttcgg
 361 gtccagcaga agggcaccct agaaacagac accatctgca cctgtgaaga aggctggcac
 421 tgtacgagtg aggcctgtga gagctgtgtc ctgcaccgct catgctcgcc cggctttggg
 481 gtcaagcaga ttgctacagg ggtttctgat accatctgcg agccctgccc agtcggcttc
 541 ttctccaatg tgtcatctgc tttcgaaaaa tgtcacccct tggacaagct gagaccaaa
 601 gacctggttg tgcaacaggc aggcacaaac aagactgatg ttgtctgtgg tcccaggat
 661 cggctgagag ccctggtggt gatccccatc atcttcggga tcctgtttgc catcctcttg
 721 gtgctggtct ttatcaaaaa ggtggccaag aagccaacca ataaggcccc ccaccccaag
 781 caggaacccc aggagatcaa ttttcccgac gatcttcctg gctccaacac tgctgctcca
 841 gtgcaggaga ctttacatgg atgccaaccg gtcacccagg aggatggcaa agagagtcgc
 901 atctcagtgc aggagagaca gtgaggctgc acccacccag gagtgtggcc acgtgggcaa
 961 acaggcagtt ggccagagag cctggtgctg ctgctgctgt ggcgtgaggg tgagggctg
1021 gcactgactg gcatagctc cccgcttctg cctgcacccc tgcagtttga gacaggagac
1081 ctggcactgg atgcagaaac agttcacctt gaagaacctc tcacttcacc ctggagccca
1141 tccagtctcc caacttgtat taaagacaga ggcagaagtt tggtggtggt ggtgttgggg
1201 tatggtttag taatatccac cagaccttcc gatccagcag tttggtgccc agagaggcat
1261 catggtggct tccctgcgcc caggaagcca tatacacaga tgcccattgc agcattgttt
1321 gtgatagtga caactggaa gctgcttaac tgtccatcag caggagactg ctaaataaa
1381 attagaatat atttatacaa cagaatctca aaaacactgt tgagtaagga aaaaaaggca
1441 tgctgctgaa tgatgggtat ggaacttttt aaaaaagtac atgctttat gtatgtatat
1501 tgcctatgga tatatgtata aatacaatat gcatcatata ttgatataac aagggttctg
1561 gaagggtaca cagaaaaccc acagctcgaa gagtggtgac gtctggggtg gggaagaagg
1621 gtctggggg
```

An exemplary human programmed death-ligand 1 (PD-L1) amino acid sequence is set forth below (SEQ ID NO: 15; GenBank Accession No: AAP13470, Version 1, incorporated herein by reference):

```
   1 mrifavfifm tywhllnaft vtvpkdlyvv eygsnmtiec kfpvekqldl aalivyweme
  61 dkniiqfvhg eedlkvqhss yrqrarllkd qlslgnaalq itdvklqdag vyrcmisygg
 121 adykritvkv napynkinqr ilvvdpvtse heltcqaegy pkaeviwtss dhqvlsgktt
 181 ttnskreekl fnvtstlrin tttneifyct frrldpeenh taelvipelp lahppnerth
 241 lvilgaillc lgvaltfifr lrkgrmmdvk kcgiqdtnsk kqsdthleet
```

An exemplary human PD-L1 nucleic acid sequence is set forth below (SEQ ID NO: 16; GenBank Accession No: AY254342, Version 1, incorporated herein by reference):

```
   1 atgaggatat ttgctgtctt tatattcatg acctactggc atttgctgaa cgcatttact
  61 gtcacggttc ccaaggacct atatgtggta gagtatggta gcaatatgac aattgaatgc
 121 aaattcccag tagaaaaaca attagacctg gctgcactaa ttgtctattg ggaaatggag
 181 gataagaaca ttattcaatt tgtgcatgga gaggaagacc tgaaggttca gcatagtagc
```

```
241   tacagacaga gggcccggct gttgaaggac cagctctccc tgggaaatgc tgcacttcag
301   atcacagatg tgaaattgca ggatgcaggg gtgtaccgct gcatgatcag ctatggtggt
361   gccgactaca agcgaattac tgtgaaagtc aatgccccat acaacaaaat caaccaaaga
421   attttggttg tggatccagt cacctctgaa catgaactga catgtcaggc tgagggctac
481   cccaaggccg aagtcatctg dacaagcagt gaccatcaag tcctgagtgg taagaccacc
541   accaccaatt ccaagagaga ggagaagctt tcaatgtgac cagcacact gagaatcaac
601   acaacaacta atgagatttt ctactgcact tttaggagat tagatcctga ggaaaaccat
661   acagctgaat tggtcatccc agaactacct ctggcacatc ctccaaatga aaggactcac
721   ttggtaattc tgggagccat cttattatgc cttggtgtag cactgacatt catcttccgt
781   ttaagaaaag ggagaatgat ggatgtgaaa aaatgtggca tccaagatac aaactcaaag
841   aagcaaagtg atacacattt ggaggagacg taa
```

An exemplary human B7-H3 amino acid sequence is set forth below (SEQ ID NO: 17; GenBank Accession No: CAE47548, Version 1, incorporated herein by reference):

```
  1   mlrrrgspgm gvhvgaalga lwfcltgale vqvpedpvva lvgtdatlcc sfspepgfsl
 61   aqlnliwqlt dtkqlvhsfa egqdqgsaya nrtalfpdll aqgnaslrlq rvrvadegsf
121   tcfvsirdfg saayslqvaa pyskpsmtle pnkdlrpgdt vtitcssyqg ypeaevfwqd
181   gqgvpltgnv ttsqmaneqg lfdvhsilrv vlgangtysc lvrnpvlqqd ahssvtitpq
241   rsptgavevq vpedpvvalv gtdatlrcsf spepgfslaq lnliwqltdt kqlvhsfteg
301   rdqgsayanr talfpdllaq gnaslrlqrv rvadegsftc fvsirdfgsa avslqvaapy
361   skpsmtlepn kdlrpgdtvt itcssyrgyp eaevfwqdgq gvpltgnvtt sqmaneqglf
421   dvhsvlrvvl gangtysclv rnpvlqqdah gsvtitgqpm tfppealwvt vglsvclial
481   lvalafvcwr kikqsceeen agaedqdgeg egsktalqpl khsdskeddg qeia
```

An exemplary human B7-H3 nucleic acid sequence is set forth below (SEQ ID NO: 18; GenBank Accession No: AJ583695, Version 1, incorporated herein by reference):

```
   1   cttccaccac ggggagccca gctgtcagcc gcctcacagg aagatgctgc gtcggcgggg
  61   cagccctggc atgggtgtgc atgtgggtgc agccctggga gcactgtggt tctgcctcac
 121   aggagccctg gaggtccagg tccctgaaga cccagtggtg gcactggtgg gcaccgatgc
 181   caccctgtgc tgctccttct cccccgagcc tggcttcagc ctggcacagc tcaacctcat
 241   ctggcagctg acagatacca aacagctggt gcacagcttt gctgagggcc aggaccaggg
 301   cagcgcctat gccaaccgca cggccctctt cccggacctg ctggcacagg gcaacgcatc
 361   cctgaggctg cagcgcgtgc gtgtggcgga cgagggcagc ttcacctgct tcgtgagcat
 421   ccgggatttc ggcagcgctg ccgtcagcct gcaggtggcc gctccctact cgaagcccag
 481   catgaccctg gagcccaaca aggacctgcg gccaggggac acggtgacca tcacgtgctc
 541   cagctaccag ggctaccctg aggctgaggt gttctggcag gatgggcagg gtgtgcccct
 601   gactggcaac gtgaccacgt cgcagatggc caacgagcag ggcttgtttg atgtgcacag
 661   catcctgcgg gtggtgctgg gtgcaaatgg cacctacagc tgcctggtgc gcaaccccgt
 721   gctgcagcag gatgcgcaca gctctgtcac catcacaccc cagagaagcc cacaggagc
 781   cgtggaggtc caggtccctg aggacccggt ggtggcccta gtgggcaccg atgccaccct
 841   gcgctgctcc ttctcccccg agcctggctt cagcctggca cagctcaacc tcatctggca
 901   gctgacagac accaaacagc tggtgcacag tttcaccgaa ggccgggacc agggcagcgc
 961   ctatgccaac cgcacggccc tcttcccgga cctgctggca caaggcaatg catccctgag
1021   gctgcagcgc gtgcgtgtgg cggacgaggg cagcttcacc tgcttcgtga gcatccggga
1081   tttcggcagc gctgccgtca gcctgcaggt ggccgctccc tactcgaagc ccagcatgac
```

-continued

```
1141  cctggagccc aacaaggacc tgcggccagg ggacacggtg accatcacgt gctccagcta
1201  ccggggctac cctgaggctg aggtgttctg gcaggatggg cagggtgtgc ccctgactgg
1261  caacgtgacc acgtcgcaga tggccaacga gcagggcttg tttgatgtgc acagcgtcct
1321  gcgggtggtg ctgggtgcga atggcaccta cagctgcctg gtgcgcaacc ccgtgctgca
1381  gcaggatgcg cacggctctg tcaccatcac agggcagcct atgacattcc ccccagaggc
1441  cctgtgggtg accgtggggc tgtctgtctg tctcattgca ctgctggtgg ccctggcttt
1501  cgtgtgctgg agaaagatca aacagagctg tgaggaggag aatgcaggag ctgaggacca
1561  ggatggggag ggagaaggct ccaagacagc cctgcagcct ctgaaacact ctgacagcaa
1621  agaagatgat ggacaagaaa tagcctgacc atgaggacca gggagctgct accccctccct
1681  acagctccta ccctctggct gcaatggggc tgcactgtga gccctgcccc aacagatgc
1741  atcctgctct gacaggtggg ctccttctcc aaaggatgcg gtacacagac cactgtgcag
1801  ccttatttct ccaatggaca tgattcccaa gtcatcctgc tgccttttttt cttatagaca
1861  caatgaacag accacccaca accttagttc tctaagtcat cctgcctgct gccttatttc
1921  acagtacata catttcttag ggacacagta cactgaccac atcaccaccc tcttcttcca
1981  gtgctgcgtg accatctggg ctgccttttt tctccaaaag atgcaatatt cagactgact
2041  gaccccctgc cttatttcac caaagacacg atgcatagtc accccggcct tgtttctcca
2101  atggccgtga tacactagtg atcatgttca gccctgcttc cacctgcata gaatcttttc
2161  ttctcagaca gggacagtgc ggcctcaaca tctcctggag tctagaagct gtttccttc
2221  ccctccttcc tcctcttgct ctagccttaa tactggcctt ttccctccct gccccaagtg
2281  aagacagggc actctgcgcc caccacatgc acagctgtgc atggagacct gcaggtgcac
2341  gtgctggaac acgtgtggtt ccccccctggc ccagcctcct ctgcagtgcc cctctcccct
2401  gcccatcctc cccacggaag catgtgctgg tcacactggt tctccagggg tctgtgatgg
2461  ggcccctggg ggtcagcttc tgtccctctg ccttctcacc tctttgttcc tttcttttca
2521  tgtatccatt cagttgatgt ttattgagca actacagatg tcagcactgt gttaggtgct
2581  gggggccctg cgtgggaaga taaagttcct ccctcaagga ctccccatcc agctgggaga
2641  cagacaacta actacactgc accctgcggt ttgcaggggg ctcctgcctg gctccctgct
2701  ccacacctcc tctgtggctc aaggcttcct ggatacctca cccccatccc acccataatt
2761  cttacccaga gcatggggtt ggggcggaaa cctggagaga gggacatagc ccctcgccac
2821  ggctagagaa tctggtggtg tccaaaatgt ctgtccaggt gtgggcaggt gggcaggcac
2881  caaggccctc tggacctttc atagcagcag aaaaggcaga gcctggggca gggcagggcc
2941  aggaatgctt tggggacacc gaggggactg ccccccccacc cccaccatgg tgctattytg
3001  gggctgggggc agtcttttcc tggcttgcct ctggccagct cctggcctct ggtagagtga
3061  gacttcagac gttytgatgc cttccggatg tcatctctcc ctgccccagg aatggaagat
3121  gtgaggactt ytaatttaaa tgtgggactc ggagggattt tgtaaactgg gggtatattt
3181  tggggaaaat aaatgtcttt gtaaaaaaaa aaaaaaaaa aa
```

An exemplary human B- and T-lymphocyte attenuator (BTLA) amino acid sequence is set forth below (SEQ ID NO: 19; GenBank Accession No: AAI07092, Version 1, incorporated herein by reference):

```
  1 mktlpamlgt gklfwvffli pyldiwnihg kescdvqlyi krqsehsila gdpfelecpv
 61 kycanrphvt wcklngttcv kledrqtswk eeknisffil hfepvlpndn gsyrcsanfq
```

```
121  snlieshstt lyvtgkqnel sdtagreinl vdahlkseqt eastrqnsqv llsetgiydn 181  dpdlcfrmqe gsevysnpcl eenkpgivya slnhsvigln srlarnvkea pteyasicvr 241  s
```

An exemplary human BTLA nucleic acid sequence is set forth below (SEQ ID NO: 20; GenBank Accession No: AJ717664, Version 1, incorporated herein by reference):
```
  1  atgaagacat tgcctgccat gcttggaact gggaaattat tttgggtctt cttcttaatc 61  ccatatctgg acatctggaa catccatggg aaagaatcat gtgatgtaca gctttatata 121  aagagacaat ctgaacactc catcttagca ggagatccct tgaactaga atgccctgtg 181  aaatactgtg ctaacaggcc tcatgtgact tggtgcaagc tcaatggaac aacatgtgta 241  aaacttgaag atagacaaac aagttggaag gaagagaaga acatttcatt tttcattcta 301  cattttgaac cagtgcttcc taatgacaat gggtcatacc gctgttctgc aaattttcag 361  tctaatctca ttgaaagcca ctcaacaact ctttatgtga cagatgtaaa aagtgcctca 421  gaacgaccct ccaaggacga aatggcaagc agaccctggc tcctgtatag tttacttcct 481  ttgggggat tgcctctact catcactacc tgtttctgcc tgttctgctg cctgagaagg 541  caccaaggaa agcaaaatga actctctgac acagcaggaa gggaaattaa cctggttgat 601  gctcacctta agagtgagca acagaagca agcaccaggc aaaattccca agtactgcta 661  tcagaaactg gaatttatga taatgaccct gacctttgtt tcaggatgca ggaagggtct 721  gaagtttatt ctaatccatg cctggaagaa acaaaccag gcattgttta tgcttccctg 781  aaccattctg tcattggact gaactcaaga ctggcaagaa atgtaaaaga agcaccaaca 841  gaatatgcat ccatatgtgt gaggagttaa
```

An exemplary human CD47 amino acid sequence is set forth below (SEQ ID NO: 21; GenBank Accession No: CEJ95640, Version 1, incorporated herein by reference):
```
  1  mwplvaalll gsaccgsaql lfnktksvef tfcndtvvip cfvtnmeaqn ttevyvkwkf 61  kgrdiytfdg alnkstvptd fssakievsq llkgdaslkm dksdavshtg nytcevtelt 121  regetiielk yrvvswfspn enilivifpi faillfwgqf giktlkyrsg gmdektiall 181  vaglvitviv ivgailfvpg eyslknatgl glivtstgil illhyyvfst aigltsfvia 241  ilviqviayi lavvglslci aacipmhgpl lisglsilal aqllglvymk fve
```

An exemplary human CD47 nucleic acid sequence is set forth below (SEQ ID NO: 22; GenBank Accession No: LN680437, Version 1, incorporated herein by reference):
```
  1  atgtggcccc tggtagcggc gctgttgctg ggctcggcgt gctgcggatc agctcagcta 61  ctatttaata aacaaaatc tgtagaattc acgttttgta atgacactgt cgtcattcca 121  tgctttgtta ctaatatgga ggcacaaaac actactgaag tatacgtaaa gtggaaattt 181  aaaggaagag atatttacac ctttgatgga gctctaaaca gtccactgt ccccactgac 241  tttagtagtg caaaaattga agtctcacaa ttactaaaag gagatgcctc tttgaagatg 301  gataagagtg atgctgtctc acacacagga aactacactt gtgaagtaac agaattaacc 361  agagaaggtg aaacgatcat cgagctaaaa tatcgtgttg tttcatggtt ttctccaaat 421  gaaaatattc ttattgttat tttcccaatt tttgctatac tcctgttctg gggacagttt 481  ggtattaaaa cacttaaata tagatccggt ggtatggatg agaaaacaat tgctttactt 541  gttgctggac tagtgatcac tgtcattgtc attgttggag ccattctttt cgtcccaggt 601  gaatattcat aaagaatgc tactggcctt ggtttaattg tgacttctac agggatatta 661  atattacttc actactatgt gtttagtaca gcgattggat taacctcctt cgtcattgcc 721  atattggtta ttcaggtgat agcctatatc ctcgctgtgg ttggactgag tctctgtatt 781  gcggcgtgta taccaatgca tggccctctt ctgatttcag gtttgagtat cttagctcta
```

```
 841 gcacaattac ttggactagt ttatatgaaa tttgtggaat aactgaagtg aagtgatgga 901 ctccgatttg gagagtagta agacgtgaaa ggaatacact tgtgtttaag caccatggcc 961 ttgatgattc actgttgggg agaagaaaca agaaaa
```

An exemplary human Fas Ligand (Fas-L) amino acid sequence is set forth below (SEQ ID NO: 23; GenBank Accession No: AAC50071, Version 1, incorporated herein by reference):

```
   1 mqqpfnypyp qiywvdssas spwappgtvl pcptsvprrp gqrrpppppp pplpppppp 61 pplpplplpp lkkrgnhstg lcllvmffmv lvalvglglg mfqlfhlqke laelrestsq 121 mhtasslekq ighpsppek kelrkvahlt gksnsrsmpl ewedtygivl lsgvkykkgg 181 lvinetglyf vyskvyfrgq scnnlplshk vymrnskypq dlvmmegkmm sycttgqmwa 241 rssylgavfn ltsadhlyvn vselslvnfe esqtffglyk l
```

An exemplary human Fas-L nucleic acid sequence is set forth below (SEQ ID NO: 24; GenBank Accession No: U11821, Version 1, incorporated herein by reference):

```
   1 tctagactca ggactgagaa gaagtaaaac cgtttgctgg ggctggcctg actccagc 61 tgccatgcag cagcccttca attacccata tccccagatc tactgggtgg acagcagtgc 121 cagctctccc tgggcccctc caggcacagt tcttccctgt ccaacctctg tgcccagaag 181 gcctggtcaa aggaggccac caccaccacc gccaccgcca ccactaccac ctccgccgcc 241 gccgccacca ctgcctccac taccgctgcc accctgaag aagagaggga accacagcac 301 aggcctgtgt ctccttgtga tgttttcat ggttctggtt gccttggtag gattgggcct 361 ggggatgttt cagctcttcc acctacagaa ggagctggca gaactccgag agtctaccag 421 ccagatgcac acagcatcat ctttggagaa gcaaataggc caccccagtc cacccctga 481 aaaaaggag ctgaggaaag tggcccattt aacaggcaag tccaactcaa ggtccatgcc 541 tctggaatgg gaagacacct atggaattgt cctgctttct ggagtgaagt ataagaaggg 601 tggccttgtg atcaatgaaa ctgggctgta ctttgtatat tccaaagtat acttccgggg 661 tcaatcttgc aacaacctgc ccctgagcca caaggtctac atgaggaact ctaagtatcc 721 ccaggatctg gtgatgatgg agggaagat gatgagctac tgcactactg gcagatgtg 781 ggcccgcagc agctacctgg gggcagtgtt caatcttacc agtgctgatc atttatatgt 841 caacgtatct gagctctctc tggtcaattt tgaggaatct cagacgtttt tcggcttata 901 taagctctaa gagaagcact ttgggattct ttccattatg attctttgtt acaggcaccg 961 agatgttcta ga
```

An exemplary human herpes virus entry mediator (HVEM) amino acid sequence is set forth below (SEQ ID NO: 25; GenBank Accession No: AAQ89238, Version 1, incorporated herein by reference):

```
   1 meppgdwgpp pwrstprtdv lrlvlyltfl gapcyapalp sckedeypvg seccpkcspg 61 yrvkeacgel tgtvcepcpp gtyiahlngl skclqcqmcd pamglrasrn csrtenavcg 121 cspghfcivq dgdhcaacra yatsspgqrv qkggtesqdt lcqncppgtf spngtleecq 181 hqtkcswlvt kagagtsssh wvwwflsgsl vivivcstvg liicvkrrkp rgdvvkvivs 241 vqrkrqeaeg eatviealqa ppdvttvave etipsftgrs pnh
```

An exemplary human HVEM nucleic acid sequence is set forth below (SEQ ID NO: 26; GenBank Accession No: U70321, Version 1, incorporated herein by reference):

```
   1 ccttcatacc ggcccttccc ctcggctttg cctggacagc tcctgcctcc cgcagggccc 61 acctgtgtcc cccagcgccg ctccacccag caggcctgag cccctctctg ctgccagaca 121 cccctgctg cccactctcc tgctgctcgg gttctgaggc acagcttgtc acaccgaggc 181 ggattctctt tctctttctc ttctggccca cagccgcagc aatggcgctg agttcctctg 241 ctggagttca tcctgctagc tgggttcccg agctgccggt ctgagcctga ggcatggagc 301 ctcctggaga ctgggggcct cctccctgga gatccacccc cagaaccgac gtcttgaggc
```

-continued

```
 361 tggtgctgta tctcaccttc ctgggagccc cctgctacgc cccagctctg ccgtcctgca
 421 aggaggacga gtacccagtg ggctccgagt gctgcccaa gtgcagtcca ggttatcgtg
 481 tgaaggaggc ctgcggggag ctgacgggca cagtgtgtga accctgccct ccaggcacct
 541 acattgccca cctcaatggc ctaagcaagt gtctgcagtg ccaaatgtgt gacccagcca
 601 tgggcctgcg cgcgagccgg aactgctcca ggacagagaa cgccgtgtgt ggctgcagcc
 661 caggccactt ctgcatcgtc caggacgggg accactgcgc cgcgtgccgc gcttacgcca
 721 cctccagccc gggccagagg gtgcagaagg gaggcaccga gagtcaggac accctgtgtc
 781 agaactgccc cccgggggacc ttctctccca atgggaccct ggaggaatgt cagcaccaga
 841 ccaagtgcag ctggctggtg acgaaggcc gagctgggac cagcagctcc cactgggtat
 901 ggtggttcct ctcagggagc ctcgtcatcg tcattgtttg ctccacagtt ggcctaatca
 961 tatgtgtgaa agaagaaag ccaagggtg atgtagtcaa ggtgatcgtc tccgtccagc
1021 ggaaaagaca ggaggcagaa ggtgaggcca cagtcattga ggccctgcag gcccctccgg
1081 acgtcaccac ggtggccgtg gaggagacaa taccctcatt cacggggagg agcccaaacc
1141 actgacccac agactctgca ccccgacgcc agagatacct ggagcgacgg ctgctgaaag
1201 aggctgtcca cctggcgaaa ccaccggagc ccggaggctt gggggctccg ccctgggctg
1261 gcttccgtct cctccagtgg agggagaggt ggggccctg ctggggtaga gctggggacg
1321 ccacgtgcca ttcccatggg ccagtgaggg cctggggcct ctgttctgct gtggcctgag
1381 ctccccagag tcctgaggag gagcgccagt tgccctcgc tcacagacca cacacccagc
1441 cctcctgggc cagcccagag ggcccttcag accccagctg tctgcgcgtc tgactcttgt
1501 ggcctcagca ggacaggccc cgggcactgc ctcacagcca aggctggact gggttggctg
1561 cagtgtggtg tttagtggat accacatcgg aagtgattt ctaaattgga tttgaattcc
1621 ggtcctgtct tctatttgtc atgaaacagt gtatttgggg agatgctgtg ggaggatgta
1681 aatatcttgt ttctcctcaa aaaaaaaaaa aaaaaaaaaa aaaa
```

An exemplary human indoleamine-pyrrole 2,3-dioxygenase (IDO1) amino acid sequence is set forth below (SEQ ID NO: 27; GenBank Accession No: NP_002155, Version 1, incorporated herein by reference):

```
  1 mahamenswt iskeyhidee vgfalpnpqe nlpdfyndwm fiakhlpdli esgqlrerve
 61 klnmlsidhl tdhksqrlar lvlgcitmay vwgkghgdvr kvlprniavp ycqlskklel
121 ppilvyadcv lanwkkkdpn kpltyenmdv lfsfrdgdcs kgfflvsllv eiaaasaikv
181 iptvfkamqm qerdtllkal leiascleka lqvfhqihdh vnpkaffsvl riylsgwkgn
241 pqlsdglvye gfwedpkefa ggsagqssvf qcfdvllgiq qtagghaaq flqdmrrymp
301 pahrnflcsl esnpsvrefv lskgdaglre aydacvkalv slrsyhlqiv tkyilipasq
361 qpkenktsed pskleakgtg gtdlmnflkt vrstteksll keg
```

An exemplary human IDO1 nucleic acid sequence is set forth below (SEQ ID NO: 28; GenBank Accession No: NM_002164, Version 5, incorporated herein by reference):

```
  1 aatttctcac tgcccctgtg ataaactgtg gtcactggct gtggcagcaa ctattataag
 61 atgctctgaa aactcttcag acactgaggg caccagagg agcagactac aagaatggca
121 cacgctatgg aaaactcctg acaatcagt aaagagtacc atattgatga agaagtgggc
181 tttgctctgc caaatccaca ggaaaatcta cctgattttt ataatgactg gatgttcatt
241 gctaaacatc tgcctgatct catagagtct ggccagcttc gagaaagagt tgagaagtta
301 aacatgctca gcattgatca tctcacagac cacaagtcac agcgccttgc acgtctagtt
361 ctgggatgca tcaccatggc atatgtgtgg ggcaaggtc atggagatgt ccgtaaggtc
421 ttgccaagaa atattgctgt tccttactgc caactctcca agaaactgga actgcctcct
```

```
 481 attttggttt atgcagactg tgtcttggca aactggaaga aaaaggatcc taataagccc 541 ctgacttatg agaacatgga cgttttgttc tcatttcgtg atggagactg cagtaaagga 601 ttcttcctgg tctctctatt ggtggaaata gcagctgctt ctgcaatcaa agtaattcct 661 actgtattca aggcaatgca atgcaagaa cgggacactt tgctaaaggc gctgttggaa 721 atagcttctt gcttggagaa agcccttcaa gtgtttcacc aaatccacga tcatgtgaac 781 ccaaaagcat ttttcagtgt tcttcgcata tatttgtctg gctggaaagg caacccccag 841 ctatcagacg tctggtgta tgaagggttc tgggaagacc caaaggagtt tgcaggggc 901 agtgcaggcc aaagcagcgt ctttcagtgc tttgacgtcc tgctgggcat ccagcagact 961 gctggtggag acatgctgc tcagttcctc caggacatga aagatatat gccaccagct 1021 cacaggaact tcctgtgctc attagagtca aatccctcag tccgtgagtt tgtcctttca 1081 aaaggtgatg ctggcctgcg ggaagcttat gacgcctgtg tgaaagctct ggtctccctg 1141 aggagctacc atctgcaaat cgtgactaag tacatcctga ttcctgcaag ccagcagcca 1201 aaggagaata gaccctctga agacccttca aaactggaag ccaaaggaac tggaggcact 1261 gatttaatga atttcctgaa gactgtaaga agtacaactg agaaatccct tttgaaggaa 1321 ggttaatgta acccaacaag agcacatttt atcatagcag agacatctgt atgcattcct 1381 gtcattaccc attgtaacag agccacaaac taatactatg caatgtttta ccaataatgc 1441 aatacaaaag acctcaaaat acctgtgcat ttcttgtagg aaaacaacaa aaggtaatta 1501 tgtgtaatta tactagaagt tttgtaatct gtatcttatc attggaataa aatgacattc 1561 aataaataaa aatgcataag atatattctg tcggctgggc gcggtggctc acgcctgtaa 1621 tcccagcact ttgggaggcc gaggcgggcg gatcacaagg tcaggagatc gagaccatct 1681 tggctaacac ggtgaaaccc cgtctctact aaaaatacaa aaaattagcc gggcgcggtg 1741 gcgggcacct gtagtcccag ctactcggga ggctgaggca ggagaatggc gtgaacctgg 1801 gaggcggagc ttgcagtgag ccaagattgt gccactgcaa tccggcctgg gctaaagagc 1861 gggactccgt ctcaaaaaaa aaaaaaaaaa gatatattct gtcataataa ataaaaatgc 1921 ataagatata aaaaaaaaaa aaaa
```

An exemplary human transforming growth factor beta (TGF-β) amino acid sequence is set forth below (SEQ ID NO: 29; GenBank Accession No: AAA36738, Version 1, incorporated herein by reference):

```
  1 mhvrslraaa phsfvalwap lfllrsalad fsldnevhss fihrrlrsqe rremqreils 61 ilglphrprp hlqgkhnsap mfmldlynam aveegggpgg qgfsypykav fstqgpplas 121 lqdshfltda dmvmsfvnlv ehdkeffhpr yhhrefrfdl skipegeavt aaefriykdy 181 irerfdnetf risvyqvlqe hlgresdlfl ldsrtlwase egwlvfdita tsnhwvvnpr 241 hnlglqlsve tldgqsinpk lagligrhgp qnkqpfmvaf fkatevhfrs irstgskqrs 301 qnrsktpknq ealrmanvae nsssdqrqac kkhelyvsfr dlgwqdwiia pegyaayyce 361 gecafplnsy mnatnhaivq tlvhfinpet vpkpccaptq lnaisvlyfd dssnvilkky 421 rnmvvracgc h
```

An exemplary human TGF-β nucleic acid sequence is set forth below (SEQ ID NO: 30; GenBank Accession No: M60316, Version 1, incorporated herein by reference):

```
  1 gtgaccgagc ggcgcggacg gccgcctgcc ccctctgcca cctggggcgg tgcgggcccg 61 gagcccggag cccgggtagc gcgtagagcc ggcgcgatgc acgtgcgctc actgcgagct 121 gcggcgccgc acagcttcgt ggcgtctctgg gcaccctgt tcctgctgcg ctccgccctg 181 gccgacttca gcctggacaa cgaggtgcac tcgagcttca tccaccggcg cctccgcagc 241 caggagcggc gggagatgca gcgcgagatc ctctccattt tgggcttgcc ccaccgcccg
```

-continued

```
 301 cgcccgcacc tccagggcaa gcacaactcg gcacccatgt tcatgctgga cctgtacaac
 361 gccatggcgg tggaggaggg cggcgggccc ggcggccagg gcttctccta cccctacaag
 421 gccgtcttca gtacccaggg ccccctctg gccagcctgc aagatagcca tttcctcacc
 481 gacgccgaca tggtcatgag cttcgtcaac ctcgtggaac atgcaaagga attcttccac
 541 ccacgctacc accatcgaga gttccggttt gatctttcca agatcccaga aggggaagct
 601 gtcacggcag ccgaattccg gatctacaag gactacatcc gggaacgctt cgacaatgag
 661 acgttccgga tcagcgttta tcaggtgctc caggagcact gggcaggga atcggatctc
 721 ttcctgctcg acagccgtac cctctgggcc tcggaggagg gctggctggt gtttgacatc
 781 acagccacca gcaaccactg ggtggtcaat ccgcggcaca acctgggcct gcagctctcg
 841 gtggagacgc tggatggca gagcatcaac cccaagttgg cgggcctgat tgggcggcac
 901 gggccccaga acaagcagcc cttcatggtg gctttcttca aggccacgga ggtccacttc
 961 cgcagcatcc ggtccacggg gagcaaacag cgcagccaga accgctccaa gacgcccaag
1021 aaccaggaag ccctgcggat ggccaacgtg gcagagaaca gcagcagcga ccagaggcag
1081 gcctgtaaga agcacgagct gtatgtcagc ttccgagacc tgggctggca ggactggatc
1141 atcgcgcctg aaggctacg cgcctactac tgtgagggg agtgtgcctt ccctctgaac
1201 tcctacatga acgccaccaa ccacgccatc gtgcagacgc tggtccactt catcaacccg
1261 gaaacggtgc ccaagccctg ctgtgcgccc acgcagctca atgccatctc cgtcctctac
1321 ttcgatgaca gctccaacgt catcctgaag aaatacagaa acatggtggt ccgggcctgt
1381 ggctgccact agctcctccg agaattcaga ccctttgggg ccaagttttt ctggatcctc
1441 cattgctc
```

An exemplary human interleukin-10 (IL-10) amino acid sequence is set forth below (SEQ ID NO: 31; GenBank Accession No: AAI04254, Version 1, incorporated herein by reference):

```
  1 mhssallccl vlltgvrasp gqgtqsensc thfpgnlpnm lrdlrdafsr vktffqmkdq
 61 ldnlllkesl ledfkgylgc qalsemiqfy leevmpqaen qdpdikahvn slgenlktlr
121 lrlrrchrfl pcenkskave qvknafnklq ekgiykamse fdifinyiea ymtmkirn
```

An exemplary human IL-10 nucleic acid sequence is set forth below (SEQ ID NO: 32; GenBank Accession No: NM_000572, Version 2, incorporated herein by reference):

```
  1 acacatcagg ggcttgctct tgcaaaacca aaccacaaga cagacttgca aaagaaggca
 61 tgcacagctc agcactgctc tgttgcctgg tcctcctgac tggggtgagg gccagcccag
121 gccagggcac ccagtctgag aacagctgca cccacttccc aggcaacctg cctaacatgc
181 ttcgagatct ccgagatgcc ttcagcagag tgaagacttt ctttcaaatg aaggatcagc
241 tggacaactt gttgttaaag gagtccttgc tggaggactt taagggttac ctgggttgcc
301 aagccttgtc tgagatgatc cagttttacc tggaggaggt gatgcccaa gctgagaacc
361 aagacccaga catcaaggcg catgtgaact ccctggggga gaacctgaag accctcaggc
421 tgaggctacg cgctgtcat cgatttcttc cctgtgaaaa caagagcaag gccgtggagc
481 aggtgaagaa tgcctttaat aagctccaag agaaggcat ctacaaagcc atgagtgagt
541 ttgacatctt catcaactac atagaagcct acatgacaat gaagatacga aactgagaca
601 tcagggtggc gactctatag actctaggac ataaattaga ggtctccaaa atcggatctg
661 gggctctggg atagctgacc cagcccttg agaaacctta ttgtacctct cttatagaat
721 atttattacc tctgatacct caacccccat ttctatttat ttactgagct tctctgtgaa
781 cgatttagaa agaagcccaa tattataatt tttttcaata tttattattt tcacctgttt
841 ttaagctgtt tccataggt gacacactat ggtatttgag tgttttaaga taaattataa
901 gttacataag ggaggaaaaa aaatgttctt tggggagcca acagaagctt ccattccaag
```

```
-continued 961  cctgaccacg ctttctagct gttgagctgt tttccctgac ctccctctaa tttatcttgt 1021  ctctgggctt ggggcttcct aactgctaca aatactctta ggaagagaaa ccagggagcc 1081  cctttgatga ttaattcacc ttccagtgtc tcggagggat tcccctaacc tcattcccca 1141  accacttcat tcttgaaagc tgtggccagc ttgttattta taacaaccta aatttggttc 1201  taggccgggc gcggtggctc acgcctgtaa tcccagcact tgggaggct  gaggcgggtg 1261  gatcacttga ggtcaggagt tcctaaccag cctggtcaac atggtgaaac cccgtctcta 1321  ctaaaaatac aaaaattagc cgggcatggt ggcgcgcacc tgtaatccca gctacttggg 1381  aggctgaggc aagagaattg cttgaaccca ggagatggaa gttgcagtga gctgatatca 1441  tgccctgta  ctccagcctg ggtgacagag caagactctg tctcaaaaaa taaaaataaa 1501  aataaatttg gttctaatag aactcagttt taactagaat ttattcaatt cctctgggaa 1561  tgttacattg tttgtctgtc ttcatagcag attttaattt tgaataaata aatgtatctt 1621  attcacatc
```

Pharmaceutical Therapeutics

For therapeutic uses, the compositions or agents described herein may be administered systemically, for example, formulated in a pharmaceutically-acceptable buffer such as physiological saline. Preferable routes of administration include, for example, subcutaneous, intravenous, interperitoneal, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, although in certain instances lower amounts will be needed because of the increased specificity of the compound. For example, a therapeutic compound is administered at a dosage that is cytotoxic to a neoplastic cell.

Formulation of Pharmaceutical Compositions

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 μg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other cases, this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other aspects, it is envisaged that doses may be in the range of about 5 mg compound/Kg body to about 20 mg compound/Kg body. In other embodiments, the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

In some cases, the compound or composition of the invention is administered at a dose that is lower than the human equivalent dosage (HED) of the no observed adverse effect level (NOAEL) over a period of three months, four months, six months, nine months, 1 year, 2 years, 3 years, 4 years or more. The NOAEL, as determined in animal studies, is useful in determining the maximum recommended starting dose for human clinical trials. For instance, the NOAELs can be extrapolated to determine human equivalent dosages. Typically, such extrapolations between species are conducted based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, see Guidance for Industry Estimating the Maximum Safe Starting Dose in Initial Clinical Trials for Therapeutics in Adult Healthy Volunteers, U.S. Department of Health and Human Services Food and Drug Administration Center for Drug Evaluation and Research (CDER), Pharmacology and Toxicology, July 2005, incorporated herein by reference.

The amount of a compound of the invention used in the prophylactic and/or therapeutic regimens which will be effective in the prevention, treatment, and/or management of cancer can be based on the currently prescribed dosage of the compound as well as assessed by methods disclosed herein and known in the art. The frequency and dosage will vary also according to factors specific for each patient depending on the specific compounds administered, the severity of the cancerous condition, the route of administration, as well as age, body, weight, response, and the past medical history of the patient. For example, the dosage of a compound of the invention which will be effective in the treatment, prevention, and/or management of cancer can be determined by administering the compound to an animal model such as, e.g., the animal models disclosed herein or known to those skilled in the art. In addition, in vitro assays may optionally be employed to help identify optimal dosage ranges.

In some aspects, the prophylactic and/or therapeutic regimens comprise titrating the dosages administered to the patient so as to achieve a specified measure of therapeutic efficacy. Such measures include a reduction in the cancer cell population in the patient.

In certain cases, the dosage of the compound of the invention in the prophylactic and/or therapeutic regimen is adjusted so as to achieve a reduction in the number or amount of cancer cells found in a test specimen extracted from a patient after undergoing the prophylactic and/or therapeutic regimen, as compared with a reference sample. Here, the reference sample is a specimen extracted from the patient undergoing therapy, wherein the specimen is extracted from the patient at an earlier time point. In one aspect, the reference sample is a specimen extracted from the same patient, prior to receiving the prophylactic and/or therapeutic regimen. For example, the number or amount of cancer cells in the test specimen is at least 2%, 5%, 10%, 15%, 20%, 30%, 40%, 50%, 60%, 70%, 80%, 90%, 95% or 99% lower than in the reference sample.

In some cases, the dosage of the compound of the invention in the prophylactic and/or therapeutic regimen is adjusted so as to achieve a number or amount of cancer cells that falls within a predetermined reference range. In these embodiments, the number or amount of cancer cells in a test specimen is compared with a predetermined reference range.

In other embodiments, the dosage of the compound of the invention in prophylactic and/or therapeutic regimen is adjusted so as to achieve a reduction in the number or amount of cancer cells found in a test specimen extracted from a patient after undergoing the prophylactic and/or therapeutic regimen, as compared with a reference sample, wherein the reference sample is a specimen is extracted from a healthy, noncancer-afflicted patient. For example, the number or amount of cancer cells in the test specimen is at least within 60%, 50%, 40%, 30%, 20%, 15%, 10%, 5%, or 2% of the number or amount of cancer cells in the reference sample.

In treating certain human patients having solid tumors, extracting multiple tissue specimens from a suspected tumor site may prove impracticable. In these cases, the dosage of the compounds of the invention in the prophylactic and/or therapeutic regimen for a human patient is extrapolated from doses in animal models that are effective to reduce the cancer population in those animal models. In the animal models, the prophylactic and/or therapeutic regimens are adjusted so as to achieve a reduction in the number or amount of cancer cells found in a test specimen extracted from an animal after undergoing the prophylactic and/or therapeutic regimen, as compared with a reference sample. The reference sample can be a specimen extracted from the same animal, prior to receiving the prophylactic and/or therapeutic regimen. In specific embodiments, the number or amount of cancer cells in the test specimen is at least 2%, 5%, 10%, 15%, 20%, 30%, 40%, 50% or 60% lower than in the reference sample. The doses effective in reducing the number or amount of cancer cells in the animals can be normalized to body surface area (e.g., mg/m$^2$) to provide an equivalent human dose.

The prophylactic and/or therapeutic regimens disclosed herein comprise administration of compounds of the invention or pharmaceutical compositions thereof to the patient in a single dose or in multiple doses (e.g., 1, 2, 3, 4, 5, 6, 7, 8, 10, 15, 20, or more doses).

In one aspect, the prophylactic and/or therapeutic regimens comprise administration of the compounds of the invention or pharmaceutical compositions thereof in multiple doses. When administered in multiple doses, the compounds or pharmaceutical compositions are administered with a frequency and in an amount sufficient to prevent, treat, and/or manage the condition. For example, the frequency of administration ranges from once a day up to about once every eight weeks. In another example, the frequency of administration ranges from about once a week up to about once every six weeks. In another example, the frequency of administration ranges from about once every three weeks up to about once every four weeks.

Generally, the dosage of a compound of the invention administered to a subject to prevent, treat, and/or manage cancer is in the range of 0.01 to 500 mg/kg, e.g., in the range of 0.1 mg/kg to 100 mg/kg, of the subject's body weight. For example, the dosage administered to a subject is in the range of 0.1 mg/kg to 50 mg/kg, or 1 mg/kg to 50 mg/kg, of the subject's body weight, more preferably in the range of 0.1 mg/kg to 25 mg/kg, or 1 mg/kg to 25 mg/kg, of the patient's body weight. In another example, the dosage of a compound of the invention administered to a subject to prevent, treat, and/or manage cancer in a patient is 500 mg/kg or less, preferably 250 mg/kg or less, 100 mg/kg or less, 95 mg/kg or less, 90 mg/kg or less, 85 mg/kg or less, 80 mg/kg or less, 75 mg/kg or less, 70 mg/kg or less, 65 mg/kg or less, 60 mg/kg or less, 55 mg/kg or less, 50 mg/kg or less, 45 mg/kg or less, 40 mg/kg or less, 35 mg/kg or less, 30 mg/kg or less, 25 mg/kg or less, 20 mg/kg or less, 15 mg/kg or less, 10 mg/kg or less, 5 mg/kg or less, 2.5 mg/kg or less, 2 mg/kg or less, 1.5 mg/kg or less, or 1 mg/kg or less of a patient's body weight.

In another example, the dosage of a compound of the invention administered to a subject to prevent, treat, and/or manage cancer in a patient is a unit dose of 0.1 to 50 mg, 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

In another example, the dosage of a compound of the invention administered to a subject to prevent, treat, and/or manage cancer in a patient is in the range of 0.01 to 10 g/m$^2$, and more typically, in the range of 0.1 g/m$^2$ to 7.5 g/m$^2$, of the subject's body weight. For example, the dosage administered to a subject is in the range of 0.5 g/m$^2$ to 5 g/m$^2$, or 1 g/m$^2$ to 5 g/m$^2$ of the subject's body's surface area.

In another example, the prophylactic and/or therapeutic regimen comprises administering to a patient one or more doses of an effective amount of a compound of the invention, wherein the dose of an effective amount achieves a plasma level of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the compound of the invention.

In another example, the prophylactic and/or therapeutic regimen comprises administering to a patient a plurality of doses of an effective amount of a compound of the invention, wherein the plurality of doses maintains a plasma level of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25

µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the compound of the invention for at least 1 day, 1 month, 2 months, 3 months, 4 months, 5 months, 6 months, 7 months, 8 months, 9 months, 10 months, 11 months, 12 months, 15 months, 18 months, 24 months or 36 months.

In other embodiments, the prophylactic and/or therapeutic regimen comprises administering to a patient a plurality of doses of an effective amount of a compound of the invention, wherein the plurality of doses maintains a plasma level of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the compound of the invention for at least 1 day, 1 month, 2 months, 3 months, 4 months, 5 months, 6 months, 7 months, 8 months, 9 months, 10 months, 11 months, 12 months, 15 months, 18 months, 24 months or 36 months.

Combination Therapy

In one example, the active compounds are administered in combination therapy, i.e., combined with other agents, e.g., therapeutic agents, that are useful for treating pathological conditions or disorders, such as various forms of cancer. The term "in combination" in this context means that the agents are given substantially contemporaneously, either simultaneously or sequentially. If given sequentially, at the onset of administration of the second compound, the first of the two compounds is in some cases still detectable at effective concentrations at the site of treatment.

The administration of a compound or a combination of compounds for the treatment of a neoplasia may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Accordingly, in some examples, the prophylactic and/or therapeutic regimen comprises administration of a compound of the invention in combination with one or more additional anticancer therapeutics. In one example, the dosages of the one or more additional anticancer therapeutics used in the combination therapy is lower than those which have been or are currently being used to prevent, treat, and/or manage cancer. The recommended dosages of the one or more additional anticancer therapeutics currently used for the prevention, treatment, and/or management of cancer can be obtained from any reference in the art including, but not limited to, Hardman et al., eds., Goodman & Gilman's The Pharmacological Basis Of Basis Of Therapeutics, 10th ed., McGraw-Hill, New York, 2001; Physician's Desk Reference (60$^{th}$ ed., 2006), which is incorporated herein by reference in its entirety.

The compound of the invention and the one or more additional anticancer therapeutics can be administered separately, simultaneously, or sequentially. In various aspects, the compound of the invention and the additional anticancer therapeutic are administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In another example, two or more anticancer therapeutics are administered within the same patient visit.

In certain aspects, the compound of the invention and the additional anticancer therapeutic are cyclically administered. Cycling therapy involves the administration of one anticancer therapeutic for a period of time, followed by the administration of a second anticancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In another example, the anticancer therapeutics are administered concurrently to a subject in separate compositions. The combination anticancer therapeutics of the invention may be administered to a subject by the same or different routes of administration.

When a compound of the invention and the additional anticancer therapeutic are administered to a subject concurrently, the term "concurrently" is not limited to the administration of the anticancer therapeutics at exactly the same time, but rather, it is meant that they are administered to a subject in a sequence and within a time interval such that they can act together (e.g., synergistically to provide an increased benefit than if they were administered otherwise). For example, the anticancer therapeutics may be administered at the same time or sequentially in any order at different points in time; however, if not administered at the same time, they should be administered sufficiently close in time so as to provide the desired therapeutic effect, preferably in a synergistic fashion. The combination anticancer therapeutics of the invention can be administered separately, in any appropriate form and by any suitable route. When the components of the combination anticancer therapeutics are not administered in the same pharmaceutical composition, it is understood that they can be administered in any order to a subject in need thereof. For example, a compound of the invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional anticancer therapeutic, to a subject in need thereof. In various aspects, the anticancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one example, the anticancer therapeutics are administered within the same office visit. In another example, the combination anticancer therapeutics of the invention are administered at 1 minute to 24 hours apart.

Release of Pharmaceutical Compositions

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Kits or Pharmaceutical Systems

The present compositions may be assembled into kits or pharmaceutical systems for use in ameliorating a neoplasia. Kits or pharmaceutical systems according to this aspect of the invention comprise a carrier means, such as a box, carton, tube or the like, having in close confinement therein one or more container means, such as vials, tubes, ampoules, or bottles. The kits or pharmaceutical systems of the invention may also comprise associated instructions for using the agents of the invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Transcription Factor STAT3 is Constitutively Activated in Many Gliomas As described in detail below, the transcription factor, STAT3, is constitutively activated in many gliomas, e.g., glioblastoma, and drives the expression of genes regulating survival, proliferation, and selfrenewal.

A STAT3 gene expression signature can be defined in a number of ways, as described in Alvarez et al., 2005 Cancer Res, (65) (12) 5054-5062, incorporated herein by reference. One such signature (described in the above paper) is comprised of the following 12 genes: MCL1, JUNB, BCL6, NFIL3, CAPN2, EGR1, VEGF, PTPCAAX1, KLF4, EXT1, NPC1, and PAK2.

Figure 4:
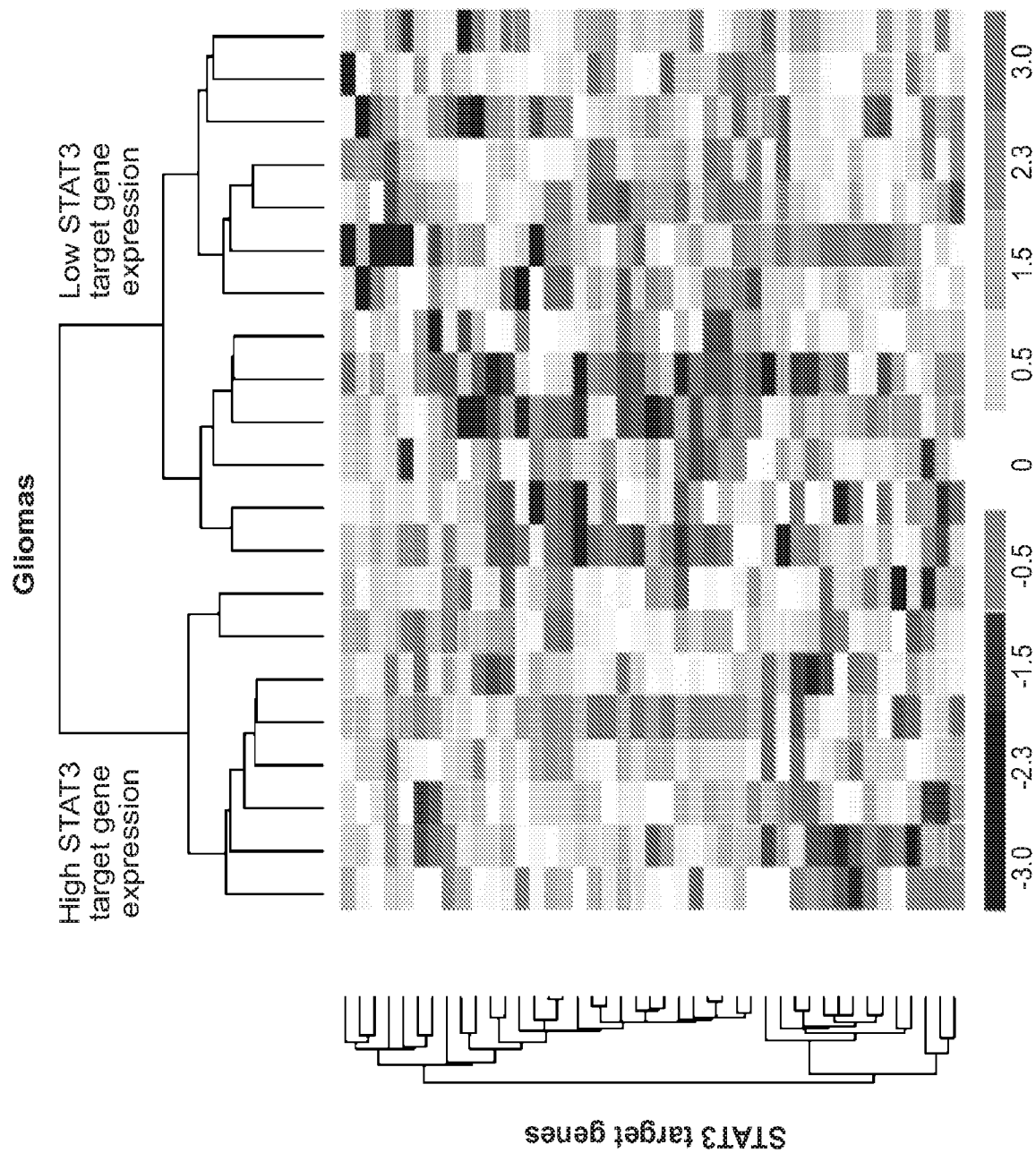
FIG. 4 is a heatmap showing that a STAT3 gene expression signature, reflecting functional STAT3 activation, is found in a subset of glioblastomas.

A STAT3 gene expression signature, reflecting functional STAT3 activation, is found in a subset of glioblastomas (FIG. 4).

Figure 5:
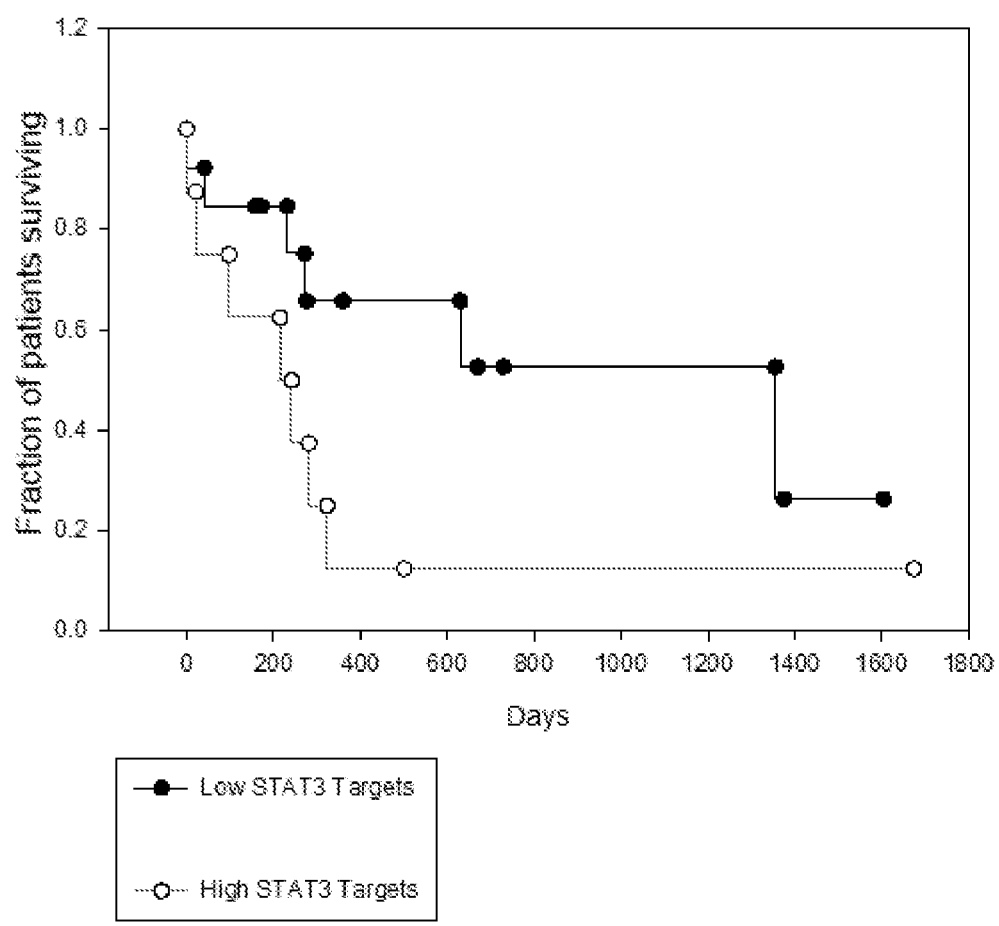
FIG. 5 is a survival graph showing that expression of a STAT3 gene expression signature is associated with worse survival of glioblastoma patients.

And, expression of the STAT3 gene expression signature is associated with worse survival of glioblastoma patients (FIG. 5).

STAT3 also alters gene expression in gliomas to make these tumors less immunogenic. Finally, described herein are two drugs that can effectively inhibit STAT3 transcriptional function at levels that can be safely achieved in patients.

Identification of STAT3 Inhibitors

Using both chemical biology approaches (Nelson et al., 2011 Oncotargets, 2:518-24; Nelson et al., 2008 Blood, 112(13):5095-102; Nelson et al., 2007 Blood, 110:2953; Takakura et al., 2011 Human Molecular Genetics, 20(21): 4143-54) and a computational approach (Lamb et al., 2006 Science, 313(5795):1929-35), two FDA-approved anti-microbial compounds, pyrimethamine (Takakura et al., 2011 Human Molecular Genetics, 20(21):4143-54) and atovaquone (Xiang et al., 2016 Blood, 128(14):1845-53) were identified as specific inhibitors of STAT3 at concentrations that can safely be achieved in humans for months at a time.

Pyrimethamine blocks the association of co-activating proteins with STAT3. Atovaquone, by contrast, blocks STAT3 tyrosine phosphorylation by a kinase independent mechanism. These drugs, which are both clinically accessible but block STAT3 transcriptional function through distinct mechanisms, are used the translational experiments described herein.

Evasion of Immune-Mediated Killing (STAT3 as an Immunosuppressive, Oncogenic Transcription Factor)

Figure 2:
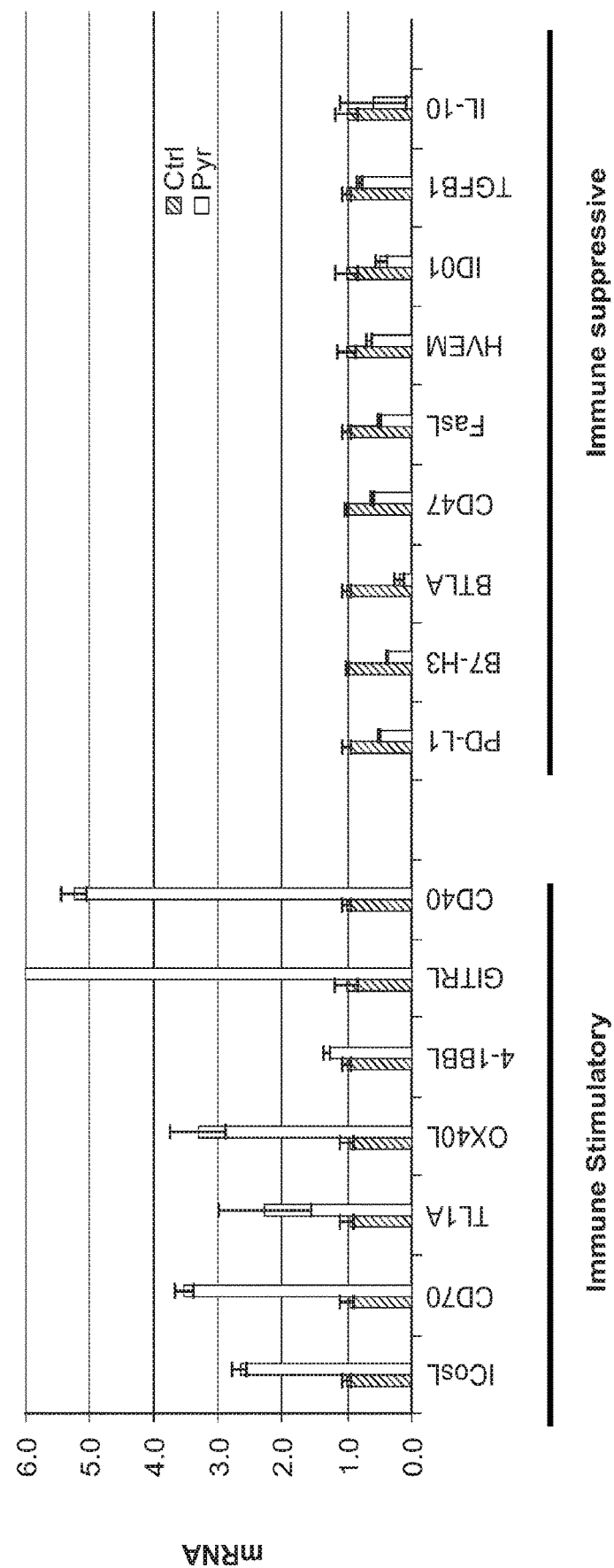
FIG. 2 is a bar graph showing mRNA expression of immune stimulatory and immune suppressive genes. U-87 MG glioblastoma cells were treated with 5 μM of the STAT3 inhibitor pyrimethamine for 6 hours, after which RNA was collected, and the expression of the indicated genes was quantitated by quantitative RT-PCR (normalized to GAPDH).

One of the key mechanisms by which tumor cells evade immune destruction is by downregulating proteins that need to be recognized by immune cells for effective killing or upregulating endogenous proteins whose function is to prevent or dampen an immune response (Kim et al., 2014 Journal for Immunotherapy of Cancer, 2(3):1). Given evidence that STAT3 inhibition might be acting through immune modulation, ChIP-seq data generated in tumors characterized by constitutively active STAT3 was analyzed. ChIP-seq showed STAT3 binding to regulatory regions of immune-modulatory genes, e.g., PD-L1. Specifically, it was identified that STAT3 bound consistently within 15,000 base pairs of 16 genes known to regulate anti-tumor immunity (Table 1 and FIG. 1). When tumor cells were treated with a pharmacological STAT3 inhibitor, or when STAT3 was depleted by RNA interference, all seven of the immunostimulatory genes showed increased expression at the mRNA level, and all nine immunesuppressive genes showed decreased expression. Data are shown for U-87 MG glioblastoma cells treated with pyrimethamine (FIG. 2), though similar findings were seen in LN-18 glioblastoma cells treated with pyrimethamine or atovaquone. Next, the cell surface expression of four of the genes (CD70, CD40, PD-L1, and CD47) were measured by flow cytometry and two of the secreted proteins (IL-10 and TGF-β) were measured by ELISA. All of these showed similar changes in expression as seen for the mRNA.

TABLE 1

STAT3-Regulated Immunomodulatory Genes

| Immune-stimulatory proteins | Immune-inhibitory proteins |
|---|---|
| Icos-L | PD-L1 |
| CD70 | B7-H3 |
| TL1A | BTLA |
| OX40-L | CD47 |
| 4-1BBL | Fas-L |
| GITR-L | HVEM |
| CD40 | IDO1 |
|  | TGF-beta |
|  | IL-10 |

Figure 6:
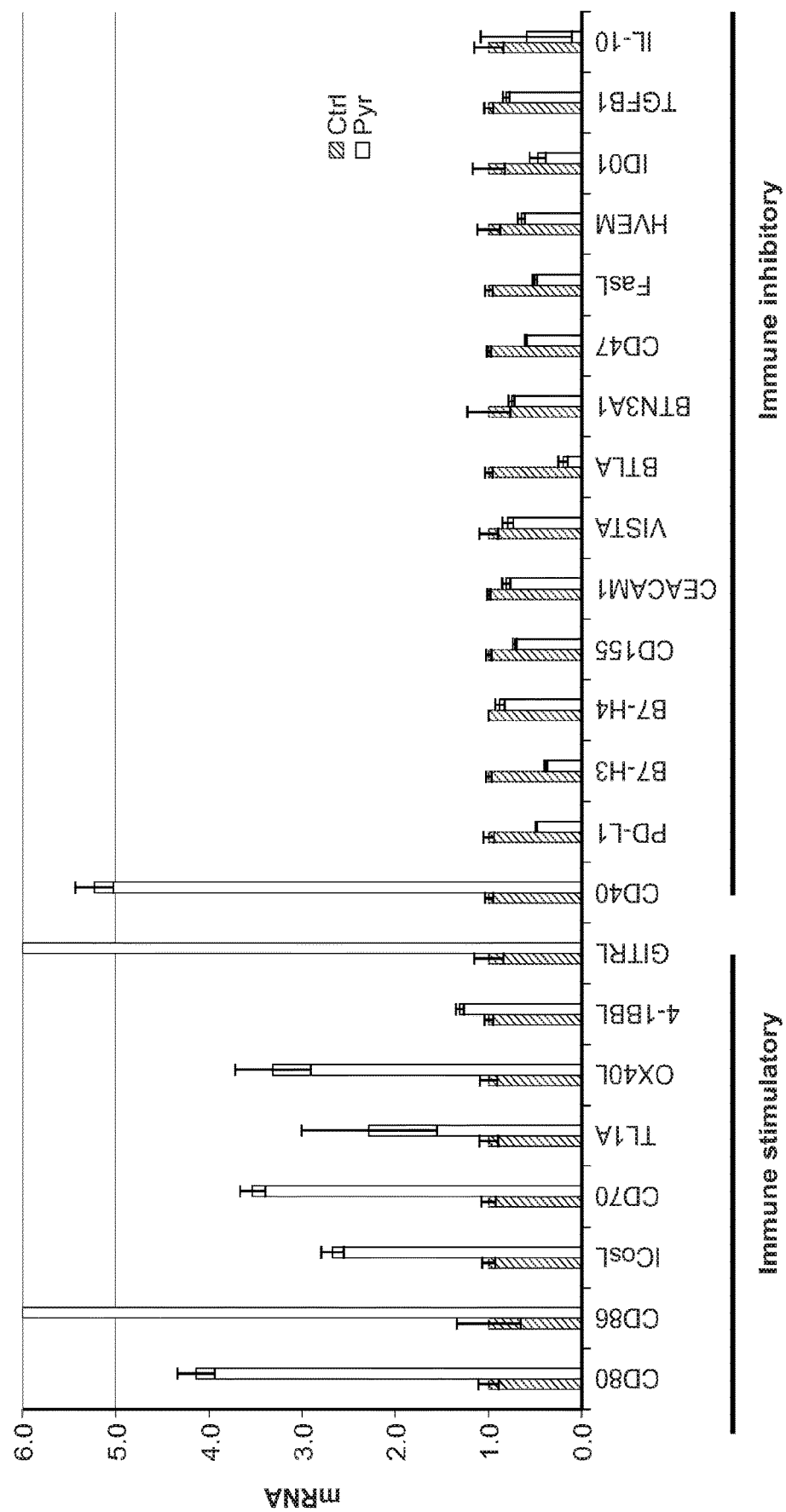
FIG. 6 is a bar graph showing mRNA expression of immune stimulatory and immune inhibitory genes. GL261 glioblastoma cells were treated with 5 μM of the STAT3 inhibitor pyrimethamine, after which RNA was collected, and the expression of the indicated genes was quantitated by quantitative RT-PCR (normalized to GAPDH).

FIG. 6 shows additional results demonstrating that STAT3 inhibition modulates tumor-produced immune regulators in GL261 murine glioblastoma cells.

Enhancing the Effects of Immune Checkpoint Inhibitors with STAT3 Inhibitors

Figure 3:
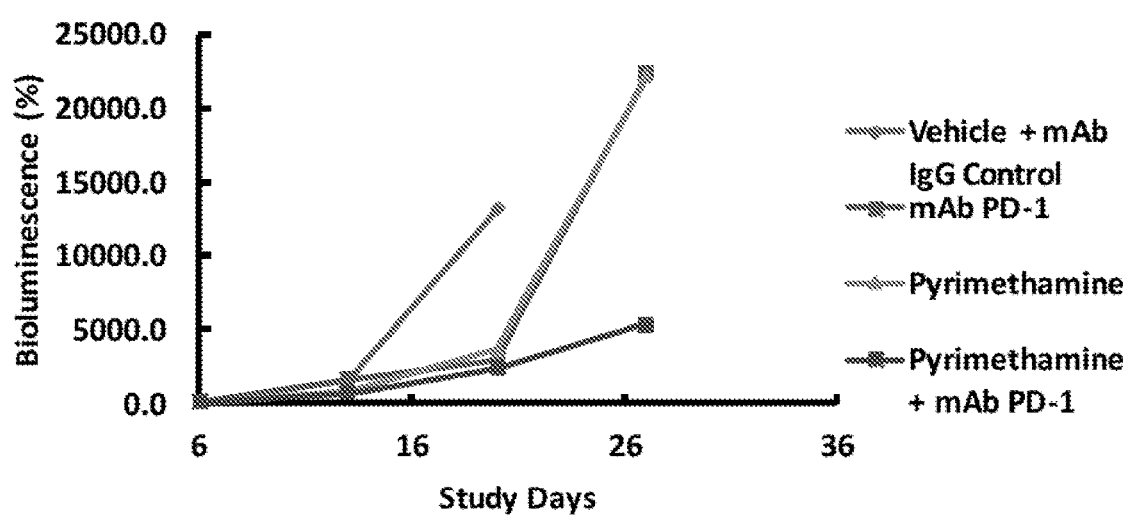
FIG. 3 is a line graph showing bioluminescence in mice. GL261 glioma cells were injected into the striatum of syngeneic mice, and then the mice were treated with controls, anti-PD-1 alone, the STAT3 inhibitor pyrimethamine alone, or the combination. Mean bioluminescence quantitation is shown for all mice in each treatment group. *, $p<0.05$, compared to other groups.
Figure 7:
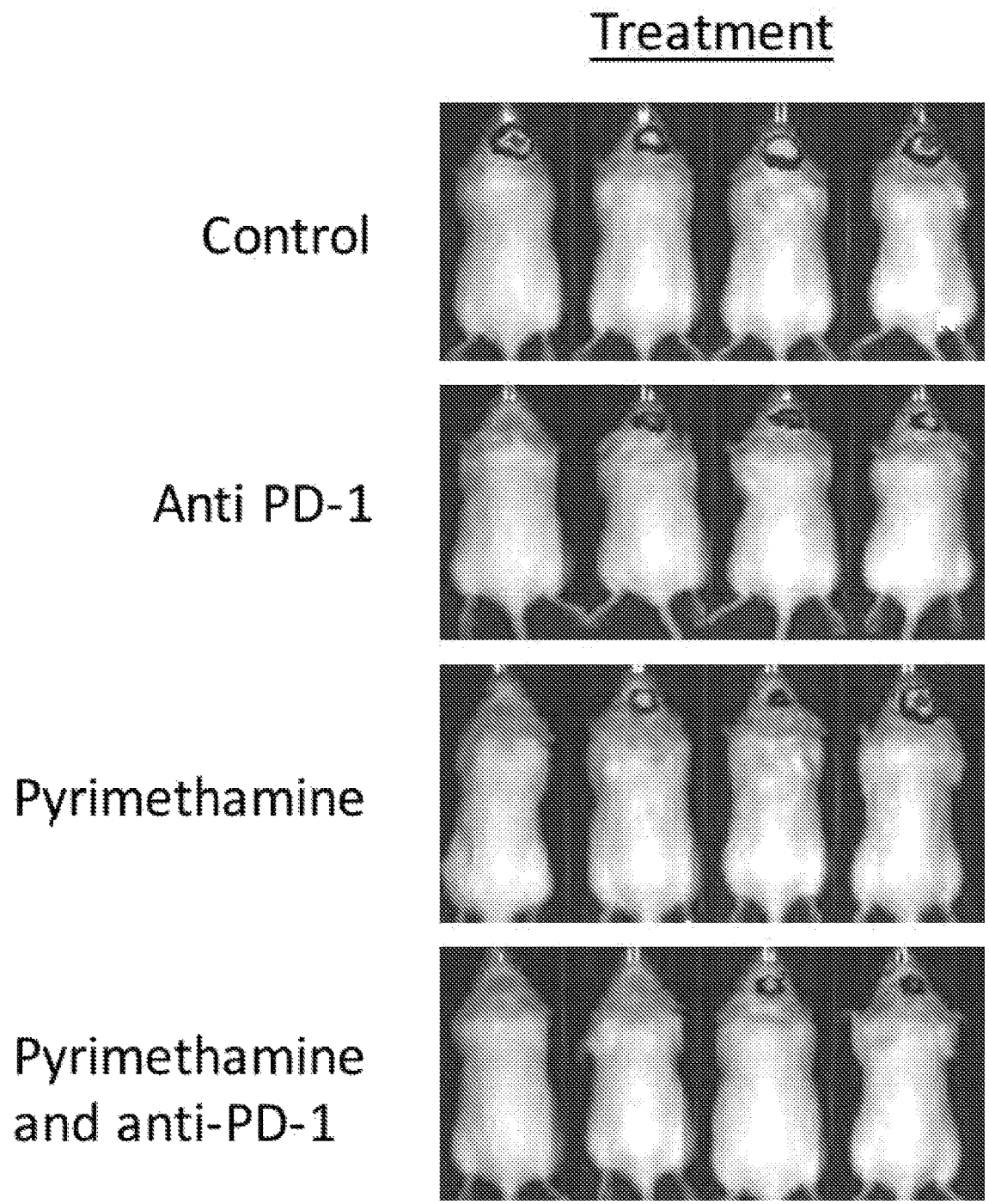
FIG. 7 is a photograph showing bioluminescence in mice bearing orthotopic GL261 glioblastoma cells treated with controls, anti-PD-1 alone, the STAT3 inhibitor, pyrimethamine, alone, or the combination.

Next, this concept was examined in vivo. GL261 glioblastoma cells were orthotopically injected directly into the right striatum of the brain of immunocompetent syngeneic C57BL/6 mice using a stereotactic frame and a Hamilton syringe. This is a highly lethal model, in which 100% of untreated animals die within 24 days of tumor implantation. Animals were treated with either pyrimethamine alone, a PD-1 blocking antibody alone, the combination, or the relevant vehicle and isotype controls. As assessed by bioluminescent imaging, both pyrimethamine and PD-1 blockade had a modest effect on decreasing tumor burden and extending the life of these animals (FIG. 3). However, unexpectedly, the combination of the two led to a dramatic decrease in tumor growth and lengthening of the life of the animals (FIG. 3). Photographs of mice in each treatment group are presented in FIG. 7. These results suggest that a combination of a STAT3 inhibitor (e.g., pyrimethamine) and PD-1 blockade enhances the efficacy of immunotherapy and provides a synergistic benefit in an immune-competent glioma model.

Example 2: Elucidation of the Molecular Mechanism by which STAT3 Bidirectionally Modulates Expression of Immunoregulatory Genes Activated STAT3 can increase expression of genes encoding immunosuppressive proteins while inhibiting expression of immunostimulatory genes. Prior to the invention described herein, a key unanswered question was how STAT3 can mediate these opposite effects in the same cell. As described in detail below, a proteomics approach is utilized to identify mediators of these divergent effects and the mechanism by which STAT3 inhibitors enhance the anti-tumor immune response is determined.

From combined ChIP-seq and gene expression profiling approaches, 16 immunoregulatory genes were identified as direct STAT3 targets. Seven of these genes are repressed by STAT3 and nine are induced by this transcription factor. Using DNA affinity chromatography, data (using sliver stained gels) has been generated and suggests that the transcriptional complexes at immunomodulatory genes upregulated by STAT3 differ from those at genes repressed by STAT3. A combination of DNA affinity chromatography and tandem mass spectrometry is used to identify candidate proteins that mediate these divergent effects of STAT3.

Candidate proteins mediating the STAT3-associated upregulation or downregulation of these immunomodulatory genes are validated both by ChIP at the STAT3 binding site for each immunoregulatory gene, and by functional studies using RNA interference and ectopic expression. The initial experiments are conducted in glioma cell lines (U-87 MG and LN-18). Subsequently, findings are validated in at least five primary glioblastoma neurospheres. These experiments provide unique mechanistic information on the mechanisms by which STAT3 can mediate divergent effects on gene regulation to effect a coordinated biological response resulting in immune evasion.

Example 3: Identification of the Key STAT3 Immunomodulatory Target Genes for Enhanced Efficacy with Checkpoint Inhibitors Described herein is the optimization of the efficacy of combinations of STAT3 inhibitors and immune checkpoint inhibitors. Using both in vitro and in vivo systems, the genes that represent the key STAT3 targets that underlie the enhanced immune response seen with STAT3 inhibitors are identified. First, the role of the two secreted factors, IL-10 and TGF-β, downregulated by STAT3 inhibition on the immune response to glioma cells is determined. This provides basic insight into the mechanism of immune suppression. These results also provide therapeutic insight, as there are a number of complementary ways to inhibit the effects of these cytokines, including blocking antibodies and decoy receptors. First, the effect of knock down (using shRNA) in glioma cells of IL-10, TGF-β, or both on the ability of splenocytes to proliferate in their presence (by CFSE dilution and flow cytometry), produce interferon-g, and cause cytolytic cell death (as measured colorimetrically by the release of LDH and GAPDH) is assessed. To rule out any cell autonomous effects, the effects of these modifications on proliferation, spontaneous apoptosis, and apoptotic threshold (as measured by BH3 profiling) of the glioma cells is also determined. If either of these proteins are playing a major role in limiting immune-mediated killing, then an enhanced effect following knockdown is observed.

The seven non-secreted immune suppressive proteins are also examined in a stepwise manner to see whether any of them alone, when depleted by RNA interference, leads to increased cell killing in the syngeneic mouse systems. Any proteins that are active individually are then examined in combination. For the seven immunostimulatory gene products whose expression is upregulated by STAT3 inhibition, a slightly different approach is used. Recognizing that it is difficult to ectopically express proteins to precise physiologic levels (which would be essential for optimal interpretation of such an experiment), an inverse approach is pursued. shRNA is used to knock down each gene individually, and then it is examined whether this attenuates the effect of the pharmacologic STAT3 inhibitors on sensitizing these cells to killing in the splenocyte assays. Such a finding would suggest that upregulation of that gene product is important to the enhanced immune-based killing of the cells. Positive findings are confirmed in the in vivo systems described in the next example.

Example 4: The Use of STAT3 Inhibitors in Conjunction with Immune Checkpoint Inhibitors The in vitro and in vivo data described herein show a dramatic benefit when STAT3 inhibitors are combined with checkpoint blockade. Next, it is determined how these agents can best be combined to optimize therapy in a clinical trial for glioma patients.

First, a series of functional experiments that are designed to provide pivotal pre-clinical data are performed to inform the design of subsequent clinical trials. A small molecule inhibitor of STAT3 function might have beneficial effects in one of two ways (or both): 1) it might make the tumor cell more immunogenic; or 2) it might make the effector T cell more effective by decreasing immunosuppressive effects of STAT3-activating cytokines in the tumor microenvironment. Understanding these potential differences, as to whether the key target is the T cell, the tumor cell, or both, alters the way a clinical trial is designed. These relationships are first examined in in vitro assays with murine CD8+ T cells purified from splenocytes. In initial experiments, either the effector T cells, the tumor cell targets, or both are pre-incubated with each STAT3 inhibitor for varying time points before the functional assays described (cytotoxicity, interferon-gamma release, CD107a degranulation, and proliferation) are performed. These experiments provide insight as to whether the key functional target of these drugs for enhancing immune-based effects is the tumor cell, the T cell, or both.

Next, the effects of these therapeutic interventions is assessed in in vivo systems with GL261 cells in syngeneic C57BL/6 mice. Efficacy experiments are performed first, combining each STAT3 inhibitor (pyrimethamine or atovaquone, given by oral gavage at a dose of 25 mg/kg) by itself or in combination with an anti-PD-1 antibody (332.8H3, mouse IgG1). Anti-PD-1 or isotype control is administered by intraperitoneal injection beginning six days after tumor implantation with repeat injections every three days. For each condition, a mechanistic examination of T cell subsets in the tumor is also performed. Animals in each treatment group are sacrificed eight days after starting therapy, a time point at which the most active and representative immune response at the tumor site are identified. Sections of brain are examined to assess the histology of the tumors, and the presence of immune infiltrates and necrosis is evaluated. Staining for CD4 and CD8 is also performed. Specific T cell populations are then quantitated by disaggregating a sample of the tissue and performing flow cytometry. In particular, CD8+/granzyme B+ effector T cells, CD4+/FoxP3+ Tregs, and the ratio of the two are measured. Recognizing that immune checkpoint blockade might lead to enhanced NK mediated killing, CD86+ cells are quantitated as a percentage of NK1.1 cells. These experiments provide a comprehensive picture of how these immune based therapies are modulated by the pharmacologic STAT3 inhibitors at both an efficacy and mechanism level.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating or preventing a solid tumor or a hematological cancer in a subject comprising:
   administering to the subject a therapeutically effective amount of a signal transducer and activator of transcription 3 (STAT3) activity inhibitor, wherein the STAT3 activity inhibitor is selected from the group consisting of pyrimethamine and atovaquone; and
   administering to the subject a therapeutically effective amount of an immune checkpoint inhibitor,
   thereby treating or preventing the solid tumor or a hematological cancer in the subject.

2. The method of claim 1, wherein the subject has been diagnosed with a solid tumor or a hematological cancer.

3. The method of claim 1, wherein the subject is identified as having elevated STAT3 activity, or wherein the subject is identified as in need of inhibiting STAT3 activity.

4. The method of claim 1, wherein the STAT3 activity inhibitor and the immune checkpoint inhibitor are administered orally, intramuscularly, subcutaneously or intravenously.

5. The method of claim 1, wherein the STAT3 activity is selected from the group consisting of STAT3 phosphorylation, STAT3 dimerization, STAT3 binding to a polynucleotide comprising a STAT3 binding site, STAT3 binding to genomic DNA, activation of a STAT3 responsive gene and STAT3 nuclear translocation.

6. The method of claim 5, wherein said STAT3 responsive gene comprises an immune-stimulatory protein selected from the group consisting of inducible costimulator-ligand (Icos-L), CD70, tumor necrosis factor-like protein 1A (TL1A), OX40-L, 4-1BB ligand (4-1BBL), glucocorticoid-induced TNFR-related protein ligand (GITR-L), and CD40.

7. The method of claim 5, wherein said STAT3 responsive gene comprises an immune-inhibitory protein selected from the group consisting of programmed death-ligand 1 (PD-L1), B7-H3, B- and T-lymphocyte attenuator (BTLA), CD47, Fas ligand (Fas-L), human herpes virus entry mediator (HVEM), indoleamine-pyrrole 2,3-dioxygenase (IDO1), transforming growth factor beta (TGF-β), and interleukin-10 (IL-10).

8. The method of claim 1, wherein the STAT3 inhibitor is administered prior to administration of the immune checkpoint inhibitor.

9. The method of claim 1, wherein the STAT3 inhibitor is administered simultaneously with the immune checkpoint inhibitor.

10. The method of claim 1, wherein the immune checkpoint inhibitor comprises an inhibitor of programmed death 1 receptor (PD-1), an inhibitor of programmed death 1 ligand (PD-L1), an inhibitor of PD-L2, an inhibitor of cytotoxic T-lymphocyte antigen 4 (CTLA-4), an inhibitor of T-cell immunoglobulin and mucin-domain containing-3 (TIM-3), an inhibitor of lymphocyte-activation gene 3 (LAG-3) (LAG-3), an inhibitor of V-domain Ig suppressor of T cell activation (VISTA), an inhibitor of T cell immunoreceptor with Ig and immunoreceptor tyrosine-based inhibition motif domains (TIGIT), or an inhibitor of B and T Lymphocyte Attenuator (BTLA; CD272).

11. The method of claim 1, wherein the solid tumor is selected from the group consisting of breast cancer, melanoma, colon cancer, ovarian cancer, pancreatic cancer, lung cancer, hepatic cancer, head and neck cancer, prostate cancer and brain cancer.

12. The method of claim 1, wherein the hematological cancer comprises leukemia or multiple myeloma.

13. The method of claim 12, wherein the leukemia is selected from the group consisting of acute lymphoblastic leukemia, acute myelogenous leukemia, chronic myelogenous leukemia, Hodgkin's disease, non-Hodgkin's lymphoma, T-cell lymphoma, B-cell lymphoma and chronic lymphocytic leukemia.

14. The method of claim 1, wherein the solid tumor or a hematological cancer comprises a glioma.

15. The method of claim 14, wherein the glioma comprises a glioblastoma.

16. The method of claim 1, wherein the subject is a human.

17. The method of claim 1, further comprising administering a chemotherapeutic agent.

18. A method of increasing the immunogenicity of a solid tumor or a hematological cancer in a subject by
administering to the subject a therapeutically effective amount of a signal transducer and activator of transcription 3 (STAT3) activity inhibitor, wherein the STAT3 activity inhibitor is selected from the group consisting of pyrimethamine and atovaquone; and
administering to the subject a therapeutically effective amount of an immune checkpoint inhibitor, thereby increasing the immunogenicity of the solid tumor or hematological cancer.

19. A method of increasing the effectiveness of an effector T cell against a solid tumor or hematological cancer by
administering to the subject a therapeutically effective amount of a STAT3 activity inhibitor, wherein the STAT3 activity inhibitor is selected from the group consisting of pyrimethamine and atovaquone; and
administering to the subject a therapeutically effective amount of an immune checkpoint inhibitor, thereby increasing the effectiveness of the effector T cell.

20. The method of claim 19, wherein the effector T cell comprises a $CD4^+$ T cell or a $CD8^+$ T cell.

21. A kit comprising a therapeutically effective amount of a STAT3 activity inhibitor, wherein the STAT3 activity inhibitor is selected from the group consisting of pyrimethamine and atovaquone; and
a therapeutically effective amount of an immune checkpoint inhibitor.

22. The kit of claim 21, wherein the immune checkpoint inhibitor comprises an anti-PD-1 antibody.

23. The method of claim 19, wherein the STAT3 activity is selected from the group consisting of STAT3 phosphorylation, STAT3 dimerization, STAT3 binding to a polynucleotide comprising a STAT3 binding site, STAT3 binding to genomic DNA, activation of a STAT3 responsive gene and STAT3 nuclear translocation.

24. The method of claim 23, wherein the STAT3 responsive gene comprises an immune-stimulatory protein selected from the group consisting of inducible costimulator-ligand (Icos-L), CD70, tumor necrosis factor-like protein 1A (TL1A), OX40-L, 4-1BB ligand (4-1BBL), glucocorticoid-induced TNFR-related protein ligand (GITR-L), and CD40.

* * * * *

```
                        SEQUENCE LISTING

<160> NUMBER OF SEQ ID NOS: 46

<210> SEQ ID NO 1
<211> LENGTH: 217
<212> TYPE: PRT
<213> ORGANISM: Homo sapiens

<400> SEQUENCE: 1

Met Ser Pro Ala Gly Met Leu Arg Gly Asp Phe Ser Leu Arg Leu Phe
1               5                   10                  15

Asn Val Thr Pro Gln Asp Glu Gln Lys Phe His Cys Leu Val Leu Ser
            20                  25                  30

Gln Ser Leu Gly Phe Gln Glu Val Leu Ser Val Glu Val Thr Leu His
        35                  40                  45

Val Ala Ala Asn Phe Ser Val Pro Val Val Ser Ala Pro His Ser Pro
    50                  55                  60

Ser Gln Asp Glu Leu Thr Phe Thr Cys Thr Ser Ile Asn Gly Tyr Pro
65                  70                  75                  80

Arg Pro Asn Val Tyr Trp Ile Asn Lys Thr Asp Asn Ser Leu Leu Asp
                85                  90                  95

Gln Ala Leu Gln Asn Asp Thr Val Phe Leu Asn Met Arg Gly Leu Tyr
            100                 105                 110

Asp Val Val Ser Val Leu Arg Ile Ala Arg Thr Pro Ser Val Asn Ile
        115                 120                 125

Gly Cys Cys Ile Glu Asn Val Leu Leu Gln Gln Asn Leu Thr Val Gly
    130                 135                 140

Ser Gln Thr Gly Asn Asp Ile Gly Glu Arg Asp Lys Ile Thr Glu Asn
145                 150                 155                 160

Pro Val Ser Thr Gly Glu Lys Asn Ala Ala Thr Trp Ser Ile Leu Ala
                165                 170                 175

Val Leu Cys Leu Leu Val Val Val Ala Val Ala Ile Gly Trp Val Cys
            180                 185                 190

Arg Asp Arg Cys Leu Gln His Ser Tyr Ala Gly Ala Trp Ala Val Ser
        195                 200                 205

Pro Glu Thr Glu Leu Thr Gly His Val
```

210          215

<210> SEQ ID NO 2
<211> LENGTH: 3168
<212> TYPE: DNA
<213> ORGANISM: Homo sapiens

<400> SEQUENCE: 2

| | | | | | |
|---|---|---|---|---|---|
| gacacggctg | cctccagcac | accgcgcgct | gggcgctcag | agcctcgggc | gcggcgggag | 60 |
| cgcagttaga | gccgatctcc | cgcgccccga | ggttgctcct | ctccgaggtc | tcccgcggcc | 120 |
| caagttctcc | gcgccccgag | gtctccgcgc | cccgaggtct | ccgcggcccg | aggtctccgc | 180 |
| ccgcaccatg | cggctgggca | gtcctggact | gctcttcctg | ctcttcagca | gccttcgagc | 240 |
| tgaacagctc | cttggaaaac | gtggacagcc | gctaccggaa | ccgagccctg | atgtcaccgg | 300 |
| ccggcatgct | gcggggcgac | ttctccctgc | gcttgttcaa | cgtcaccccc | caggacgagc | 360 |
| agaagtttca | ctgcctggtg | ttgagccaat | ccctgggatt | ccaggaggtt | ttgagcgttg | 420 |
| aggttacact | gcatgtggca | gcaaacttca | gcgtgcccgt | cgtcagcgcc | cccacagcc | 480 |
| cctcccagga | tgagctcacc | ttcacgtgta | catccataaa | cggctacccc | aggcccaacg | 540 |
| tgtactggat | caataagacg | gacaacagcc | tgctggacca | ggctctgcag | aatgacaccg | 600 |
| tcttcttgaa | catgcggggc | ttgtatgacg | tggtcagcgt | gctgaggatc | gcacggaccc | 660 |
| ccagcgtgaa | cattggctgc | tgcatagaga | acgtgcttct | gcagcagaac | ctgactgtcg | 720 |
| gcagccagac | aggaaatgac | atcggagaga | gagacaagat | cacagagaat | ccagtcagta | 780 |
| ccggcgagaa | aaacgcggcc | acgtggaaca | tcctggctgt | cctgtgcctg | cttgtggtcg | 840 |
| tggcggtggc | cataggctgg | gtgtgcaggg | accgatgcct | ccaacacagc | tatgcaggtg | 900 |
| cctgggctgt | gagtccggag | acagagctca | ctggccacgt | tgaccggag | ctcaccgccc | 960 |
| agagcgtgga | cagggcttcc | gtgagacgcc | accgtgagag | gccaggtggc | agcttgagca | 1020 |
| tggactccca | gactgcaggg | gagcacttgg | ggcagccccc | agaaggacca | ctgctggatc | 1080 |
| ccagggagaa | cctgctggcg | ttggctgtga | tcctggaatg | aggcccttc | aaaagcgtca | 1140 |
| tccacaccaa | aggcaaatgt | ccccaagtga | gtgggctccc | cgctgtcact | gccagtcacc | 1200 |
| cacaggaagg | gactggtgat | gggctgtctc | tacccggagc | gtgcgggatt | cagcaccagg | 1260 |
| ctcttcccag | tacccagac | ccactgtggg | tcttcccgtg | ggatgcggga | tcctgagacc | 1320 |
| gaagggtgtt | tggtttaaaa | agaagactgg | gcgtccgctc | ttccaggacg | gcctctgtgc | 1380 |
| tgctggggtc | acgcgaggct | gtttgcaggg | gacacggtca | caggagctct | tctgccctga | 1440 |
| acgctcccaa | cctgcctccc | gcccggaagc | cacaggaccc | actcatgtgt | gtgcccacaa | 1500 |
| gtgtagttag | ccgtccacac | cgaggagccc | ccggaagtcc | ccactgggct | tcagtgtcct | 1560 |
| ctgccacatt | ccctgggagg | aacaatgtcc | ctcggctgtt | ccgtgaaaa | gttgagccac | 1620 |
| ctttggaaga | cgcacgggtg | gagtttgcca | gaagaaaggc | tgtgccaggg | ccgtgtttgg | 1680 |
| ctacaggggc | tgccggggct | cttggctctg | cagcgagaaa | gacacagccc | agcagggctg | 1740 |
| gagacgccca | tgtccagcag | gcgcaggcct | ggcaacacgg | tccccagagt | cctgagcagc | 1800 |
| agttaggtgc | atggagaggg | tatcacctgg | tggccacagt | cccccttctc | acctcagcaa | 1860 |
| tgatccccaa | agtgagaggt | ggctccccg | gccccacca | cctcagcag | ccccacccca | 1920 |
| ctcaaccctg | agggtcccca | gggtcctgat | gaagacctcc | gacccagcg | ccaggctcct | 1980 |
| cggagcccaa | cagtcccaag | ggggcaggag | acggggtggt | ccagtgctga | ggggtacagc | 2040 |
| cctgggccct | gaccagcccc | ggcacctgcc | atgctggttc | ccggaatgaa | tcagctgctg | 2100 |

```
actgtctcca gaagggctgg aaaggatgct gccaggtgac ccgaggtgca ctcgccccag    2160
ggagatggag tagacagcct ggcctggccc tcgggacaca ttgtctgccc cggggctatg    2220
ggcaaatgcc cctccttctt acttcccaga atccctgac  attcccaggg tcagccagga    2280
cctgttacag ccctggtcac ttggaactga cagctgtgtg aggcctgcac ttctcagacc    2340
cagacttaga acaaaaggag gagtgaggac tcaaggctac aatgaggttc cagtacttgt    2400
tacaagaaat tggttttctg caaaaaaagt ccctacctga gcctttaggt gaatgtggga    2460
tccactcccg cttttaacat gaaagcatta gaagatgtgt ggtgtttata aagaacagt    2520 tgtcatcacc gggcattgat tggcaggac  aaggagctgc ttgggtgtgg aaagttgggg    2580
cgttggaaag tgggctgtgg tgcccatttg cagtgactgt gaagtgactc caggacggac    2640
ctgcgggggc acccagaggt cctaagcccc aggactgagg gtcgtgcatc accactcggg    2700
tgtcccggga ggtgccctgg gcccggggac ctcacaggca ggacggcgac actaatgcag    2760
ggagagggag tctggcccca gcttttccta tcagaggcga ttttccttca ccaggggatg    2820
ggcaggaaag aggcaggggc cccagaagct tctgtccctc atgcctgagg gcacggggga    2880
cacttggagg ctgctgtcac cactgtgcgt ccaaggccat gctctctgcg ggtcagtgcc    2940
tgagtctcgc ctccctgctg gtccctgaag cccctcaga  agccctgcct gtcacgtcgg    3000
catttgtgag acctaccctg taacgcctgc ccctctcagc ccaacatcag cttcctcttt    3060
ctcccttgct gtagacaggc tggattccag tgttgggaca gccatctcca gaaacctgac    3120
ttaagagagt aagatgcaaa tcgtgcctgt aaaaaaaaaa aaaaaaaa                 3168

<210> SEQ ID NO 3
<211> LENGTH: 193
<212> TYPE: PRT
<213> ORGANISM: Homo sapiens

<400> SEQUENCE: 3

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
```

Pro

<210> SEQ ID NO 4
<211> LENGTH: 913
<212> TYPE: DNA
<213> ORGANISM: Homo sapiens

<400> SEQUENCE: 4

```
ccagagaggg gcaggctggt cccctgacag gttgaagcaa gtagacgccc aggagccccg      60
ggaggggggct gcagtttcct tccttccttc tcggcagcgc tccgcgcccc catcgccct    120
cctgcgctag cggaggtgat cgccgcggcg atgccggagg agggttcggg ctgctcggtg    180
cggcgcaggc cctatgggtg cgtcctgcgg gctgctttgg tcccattggt cgcgggcttg    240
gtgatctgcc tcgtggtgtg catccagcgc ttcgcacagg ctcagcagca gctgccgctc    300
gagtcacttg ggtgggacgt agctgagctg cagctgaatc acacaggacc tcagcaggac    360
cccaggctat actggcaggg gggcccagca ctgggccgct ccttcctgca tggaccagag    420
ctggacaagg ggcagctacg tatccatcgt gatggcatct acatggtaca catccaggtg    480
acgctggcca tctgctcctc cacgacggcc tccaggcacc accccaccac cctggccgtg    540
ggaatctgct ctcccgcctc ccgtagcatc agcctgctgc gtctcagctt ccaccaaggt    600
tgtaccattg cctcccagcg cctgacgccc tggcccgag gggacacact ctgcaccaac    660
ctcactggga cacttttgcc ttcccgaaac actgatgaga ccttctttgg agtgcagtgg    720
gtgcgcccct gaccactgct gctgattagg gttttttaaa tttattttta ttttatttaa    780
gttcaagaga aaaagtgtac acacaggggc cacccggggt tggggtggga gtgtggtggg    840
gggtagtggt ggcaggacaa gagaaggcat tgagcttttt ctttcatttt cctattaaaa    900
aatacaaaaa tca                                                       913
```

<210> SEQ ID NO 5
<211> LENGTH: 251
<212> TYPE: PRT
<213> ORGANISM: Homo sapiens

<400> SEQUENCE: 5

```
Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
                20                  25                  30

Ala Arg Trp Ala Leu Thr Cys Cys Leu Val Leu Pro Phe Leu Ala
            35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140
```

```
Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 6
<211> LENGTH: 2016
<212> TYPE: DNA
<213> ORGANISM: Homo sapiens

<400> SEQUENCE: 6
gagagggaaa agggaaggag gagactgagt gattaagtca cccactgtga agagctggtc      60
ttctatttaa tgggggctct ctctgcccag gagtcagagg tgcctccagg agcagcagga    120
gcatggccga ggatctggga ctgagctttg gggaaacagc cagtgtggaa atgctgccag    180
agcacggcag ctgcaggccc aaggccagga gcagcagcgc acgctgggct ctcacctgct    240
gcctggtgtt gctccccttc cttgcaggac tcaccacata cctgcttgtc agccagctcc    300
gggcccaggg agaggcctgt gtgcagttcc aggctctaaa aggacaggag tttgcacctt    360
cacatcagca agtttatgca cctcttagag cagacgagaa taagccaagg cacacctga     420 cagttgtgag acaaactccc acacagcact ttaaaaatca gttcccagct ctgcactggg    480
aacatgaact aggcctggcc ttcaccaaga accgaatgaa ctataccaac aaattcctgc    540
tgatcccaga gtcgggagac tacttcattt actcccaggt cacattccgt gggatgacct    600
ctgagtgcag tgaaatcaga caagcaggcc gaccaaacaa gccagactcc atcactgtgg    660
tcatcaccaa ggtaacagac agctaccctg agccaaccca gctcctcatg gggaccaagt    720
ctgtatgcga agtaggtagc aactggttcc agccatcta cctcggagcc atgttctcct    780
tgcaagaagg ggacaagcta atggtgaacg tcagtgacat ctctttggtg gattacacaa    840
aagaagataa aaccttcttt ggagccttct tactatagga ggagagcaaa tatcattata    900
tgaaagtcct ctgccaccga gttcctaatt ttctttgttc aaatgtaatt ataaccaggg    960
gttttcttgg ggccgggagt aggggggcatt ccacagggac aacggtttag ctatgaaatt   1020
tggggcccaa aatttcacac ttcatgtgcc ttactgatga gagtactaac tggaaaaggc   1080
tgaagagagc aaatatatta ttaagatggg ttggaggatt ggcgagtttc taaatattaa   1140
gacactgatc actaaatgaa tggatgatct actcgggtca ggattgaaag agaaatattt   1200
caacacctcc ctgctataca atggtcacca gtggtccagt tattgttcaa tttgatcata   1260
aatttgcttc aattcaggag ctttgaagga agtccaagga aagctctaga aaacagtata   1320
aactttcaga ggcaaaatcc ttcaccaatt tttccacata ctttcatgcc ttgcctaaaa   1380
aaaatgaaaa gagagttggt atgtctcatg aatgttcaca cagaaggagt tggttttcat   1440
gtcatctaca gcatatgaga aaagctacct ttcttttgat tatgtacaca gatatctaaa   1500
```

```
taaggaagta tgagtttcac atgtatatca aaaatacaac agttgcttgt attcagtaga   1560
gttttcttgc ccacctattt tgtgctgggt tctaccttaa cccagaagac actatgaaaa   1620
acaagacaga ctccactcaa aatttatatg aacaccacta gatacttcct gatcaaacat   1680
cagtcaacat actctaaaga ataactccaa gtcttggcca ggcgcagtgg ctcacacctg   1740
taatcccaac actttgggag gccaaggtgg gtggatcatc taaggccggg agttcaagac   1800
cagcctgacc aacgtggaga aaccccatct ctactaaaaa tacaaaatta gccgggcgtg   1860
gtagcgcatg gctgtaatcc tggctactca ggaggccgag gcagaagaat tgcttgaact   1920
ggggaggcag aggttgcggt gagcccagat cgcgccattg cactccagcc tgggtaacaa   1980
gagcaaaact ctgtccaaaa aaaaaaaaaa aaaaaa                             2016
```

<210> SEQ ID NO 7
<211> LENGTH: 67
<212> TYPE: PRT
<213> ORGANISM: Homo sapiens

<400> SEQUENCE: 7

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr
65
```

<210> SEQ ID NO 8
<211> LENGTH: 656
<212> TYPE: PRT
<213> ORGANISM: Homo sapiens

<400> SEQUENCE: 8

```
Ala Thr Cys Gly Cys Ala Cys Gly Thr Thr Cys Cys Cys Thr Thr
1               5                   10                  15

Thr Thr Cys Cys Ala Thr Ala Thr Cys Thr Thr Cys Ala Thr Cys Thr
            20                  25                  30

Thr Cys Cys Cys Thr Cys Thr Ala Cys Cys Cys Ala Gly Ala Thr Thr
        35                  40                  45

Gly Thr Gly Ala Ala Gly Ala Thr Gly Gly Ala Ala Gly Gly Gly
    50                  55                  60

Thr Cys Ala Ala Cys Cys Cys Thr Gly Gly Ala Ala Gly Ala
65                  70                  75                  80

Gly Ala Ala Thr Gly Thr Gly Gly Ala Ala Thr Gly Cys Ala
                85                  90                  95

Gly Cys Cys Ala Gly Gly Cys Cys Ala Ala Gly Ala Thr Cys Gly
            100                 105                 110

Ala Gly Ala Gly Gly Ala Ala Cys Ala Ala Gly Cys Thr Ala Thr
        115                 120                 125

Gly Cys Thr Gly Gly Thr Gly Gly Cys Cys Thr Cys Gly Thr Ala
    130                 135                 140

Ala Thr Thr Cys Ala Gly Gly Gly Ala Cys Thr Gly Gly Gly Cys
145                 150                 155                 160
```

```
Thr Gly Cys Thr Cys Cys Thr Gly Thr Gly Cys Thr Cys Ala Cys
            165                 170                 175

Cys Thr Ala Cys Ala Thr Cys Thr Gly Cys Cys Thr Gly Cys Ala Cys
            180                 185                 190

Thr Thr Cys Thr Cys Thr Gly Cys Thr Cys Thr Thr Cys Ala Gly Gly
            195                 200                 205

Thr Ala Ala Gly Ala Thr Gly Cys Ala Cys Cys Ala Cys Thr Gly Gly
            210                 215                 220

Gly Cys Gly Cys Thr Gly Thr Thr Thr Thr Cys Cys Ala Cys Cys
225             230                 235                 240

Ala Gly Cys Thr Cys Ala Thr Gly Cys Thr Gly Ala Thr Gly Gly Cys
            245                 250                 255

Ala Gly Cys Thr Asn Asn Asn

```
                580             585             590
Ala Thr Cys Thr Cys Thr Thr Cys Thr Thr Thr Thr Cys Cys Thr Ala
            595             600             605

Ala Gly Gly Gly Ala Ala Gly Ala Ala Thr Thr Ala Ala Ala Thr
        610             615             620

Thr Cys Cys Ala Ala Thr Thr Ala Ala Ala Thr Cys Cys Cys Ala Gly
625             630             635             640

Ala Ala Thr Thr Gly Thr Thr Gly Thr Ala Gly Cys Cys Thr Gly Cys
                645             650             655

<210> SEQ ID NO 9
<211> LENGTH: 254
<212> TYPE: PRT
<213> ORGANISM: Homo sapiens

<400> SEQUENCE: 9

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Cys Ala Val Phe
        35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 10
<211> LENGTH: 1680
<212> TYPE: DNA
<213> ORGANISM: Homo sapiens

<400> SEQUENCE: 10
aaaaagcggc gcgctgtgtc ttcccgcagt ctctcgtcat ggaatacgcc tctgacgctt    60
```

-continued

```
cactggaccc cgaagccccg tggcctcccg cgccccgcgc tcgcgcctgc cgcgtactgc      120
cttgggccct ggtcgcgggg ctgctgctgc tgctgctgct cgctgccgcc tgcgccgtct      180
tcctcgcctg ccctggggcc gtgtccgggg ctcgcgcctc gcccggctcc gcggccagcc      240
cgagactccg cgagggtccc gagctttcgc ccgacgatcc cgccgcctc ttggacctgc       300 ggcagggcat gtttgcgcag ctggtggccc aaaatgttct gctgatcgat gggcccctga      360
gctggtacag tgacccaggc ctggcaggcg tgtccctgac gggggggcctg agctacaaag     420 aggacacgaa ggagctggtg gtggccaagg ctggagtcta ctatgtcttc tttcaactag      480
agctgcggcg cgtggtggcc ggcgagggct caggctccgt ttcacttgcg ctgcacctgc      540
agccactgcg ctctgctgct ggggccgccg ccctggcttt gaccgtggac ctgccacccg      600
cctcctccga ggctcggaac tcggccttcg gtttccaggg ccgcttgctg cacctgagtg      660
ccggccagcg cctgggcgtc catcttcaca ctgaggccag ggcacgccat gcctggcagc      720
ttacccaggg cgccacagtc ttgggactct ccgggtgac ccccgaaatc ccagccggac       780
tcccttcacc gaggtcggaa taacgtccag cctgggtgca gcccacctgg acagagtccg      840
aatcctactc catccttcat ggagacccct ggtgctgggt ccctgctgct ttctctacct      900
caagggcctt ggcagggtc cctgctgctg acctccccctt gaggaccctc ctcacccact      960
ccttccccaa gttggacctt gatattttatt ctgagcctga gctcagataa tatattattat    1020 atattatata tatatataa tttctatta aagaggatcc tgagtttgtg aatggacttt        1080
tttagaggag ttgttttggg gggggggggg tcttcgacat tgccgaggct ggtcttgaac      1140
tcctggactt agacgatcct cctgcctcag cctcccaagc aactgggatt catcctttct      1200
attaattcat tgtacttatt tgcttatttg tgtgtattga gcatctgtaa gtgccagca       1260 tgtgcccag gctaggggc tatagaaaca tctagaaata gactgaaaga aaatctgagt        1320
tatggtaata cgtgaggaat ttaaagactc atccccagcc tccacctcct gtgtgatact      1380 tggggggctag ctttttttctt tctttctttt ttttgagatg gtcttgttct gtcaaccagg    1440
ctagaatgca gcggtgcaat catgagtcaa tgcagcctcc agcctcgacc tcccgaggct     1500
caggtgatcc tcccatctca gcctctcgag tagctgggac cacagttgtg tgccaccaca     1560
cttggctaac tttttaattt ttttgcggag acggtattgc tatgttgcca aggttgttta     1620
catgccagta caatttataa taaacactca ttttcctcc ctctgaaaaa aaaaaaaaa       1680
```

<210> SEQ ID NO 11
<211> LENGTH: 173
<212> TYPE: PRT
<213> ORGANISM: Homo sapiens

<400> SEQUENCE: 11

```
Met Glu Glu Met Pro Leu Arg Glu Ser Ser Pro Gln Arg Ala Glu Arg
1               5                   10                  15

Cys Lys Lys Ser Trp Leu Leu Cys Ile Val Ala Leu Leu Leu Met Leu
            20                  25                  30

Leu Cys Ser Leu Gly Thr Leu Ile Tyr Thr Ser Leu Lys Pro Thr Ala
        35                  40                  45

Ile Glu Ser Cys Met Val Lys Phe Glu Leu Ser Ser Ser Lys Trp His
    50                  55                  60

Met Thr Ser Pro Lys Pro His Cys Val Asn Thr Thr Ser Asp Gly Lys
65                  70                  75                  80

Leu Lys Ile Leu Gln Ser Gly Thr Tyr Leu Ile Tyr Gly Gln Val Ile
```

|  |  | 85 |  |  |  | 90 |  |  |  | 95 |  |
|---|---|---|---|---|---|---|---|---|---|---|---|

Pro Val Asp Lys Lys Tyr Ile Lys Asp Asn Ala Pro Phe Val Val Gln
        100                  105                  110

Ile Tyr Lys Lys Asn Asp Val Leu Gln Thr Leu Met Asn Asp Phe Gln
        115                  120                  125

Ile Leu Pro Ile Gly Gly Val Tyr Glu Leu His Ala Gly Asp Asn Ile
    130                  135                  140

Tyr Leu Lys Phe Asn Ser Lys Asp His Ile Gln Lys Thr Asn Thr Tyr
145                150                  155                  160

Trp Gly Ile Ile Leu Met Pro Asp Leu Pro Phe Ile Ser
        165                  170

<210> SEQ ID NO 12
<211> LENGTH: 2064
<212> TYPE: DNA
<213> ORGANISM: Homo sapiens

<400> SEQUENCE: 12

| | |
|---|---|
| ttgtgggtat ctgctttccc cagttctcat tccatcagag aacgagttct agcctcatgg | 60 |
| aggaaatgcc tttgagagaa tcaagtcctc aaagggcaga gaggtgcaag aagtcatggc | 120 |
| tcttgtgcat agtggctctg ttactgatgt tgctctgttc tttgggtaca ctgatctata | 180 |
| cttcactcaa gccaactgcc atcgagtcct gcatggttaa gtttgaacta tcatcctcaa | 240 |
| aatggcacat gacatctccc aaacctcact gtgtgaatac gacatctgat gggaagctga | 300 |
| agatactgca gagtggcaca tatttaatct acggccaagt gattcctgtg ataagaaat | 360 |
| acataaaaga caatgccccc ttcgtagtac agatatataa aagaatgat gtcctacaaa | 420 |
| ctctaatgaa tgattttcaa atcttgccta taggaggggt ttatgaactg catgctggag | 480 |
| ataacatata tctgaagttc aactctaaag accatattca gaaaactaac acatactggg | 540 |
| ggatcatctt aatgcctgat ctaccattca tctcttagag attgggtttg gtctcctcat | 600 |
| cttcttcttt gtatcccgag atgctggtgg gtgggttgga gggggatgat tgatggcaat | 660 |
| gcacacagtt tgtgagggct tacaaattga cacaatcaga gcctcttggc atataaaatt | 720 |
| ttagccctca tatctgtctg aagaggactc agcaaatggg ccaatcccta atgttgggtc | 780 |
| tgcaaatgga cttgtacaat ccatgataaa aaggagtatg gccacagaa gacagaaact | 840 |
| cttccaaaga atgtctttct aaccttgatc cctgggtaga atgagatcct gtttccatgg | 900 |
| gagtcttact tggcttgcaa aaagggtgt agggcagtag cttggccttt tttccatcat | 960 |
| aatttccttg agctgtttta ccttaatccc tccaaactct caccttctga gagcctccta | 1020 |
| atgaaacatt gttagactgg tggggtggcc aagacatgcc aacaacaccc ttctttagag | 1080 |
| gtggtgtttt tagaggacag agaacattat gaagcctaga gcagcagagg tcaagatgcc | 1140 |
| acgaaatgga attgatctgg gaattttttt ttttttcat tctcaggatg caggttcatt | 1200 |
| ctgaactttc ccctaggcct tcattgcttt tgtgtgtatg tgtgcataaa ttctgcaaat | 1260 |
| agaaaaatga gagtttgcac cagtactcac tagatttaac accagaaagt ggtactttc | 1320 |
| tggctgtatt atgccatgat agcacatttt ctgttggtgt tccctaactg acaagtataa | 1380 |
| cagttttcct aaaccacaca acaatgctat gatgttaatg gggtagatat ttttggaaaa | 1440 |
| aaattgcaca gtgagaacat gggtagatga accctaagac tcttacctca attcagaact | 1500 |
| cgcaaggagt taagtgagtg gggtcttcat tagaccattc acatggtctc tgctttgaaa | 1560 |
| ctggcgttgc tactgtctca ttatacatca ctaaaatgga attaactcaa ctttgaaatg | 1620 |

-continued

```
gatgcatcga ctttacccca aggtgtccag aatgaagcta caagactttt accagcagtc    1680
attttccttt tgcctggagc aagaagatcc aggatactgt tggaagagtt catctcactc    1740
aaccatgctg actttccaaa gtaataatga acatttgtgt tcaaattttg gattctgtta    1800
aatttagcca gcttgtgagt tcttgtcgaa aagtatttta aaccaattta cactatttat    1860
gggtatttgt gaaaagctat atagtgatat tttatatata actaatttaa aatatttta     1920 ttttatgtaa caaaaatact ataggctaag ctatttcttc ttattttttt atgaatactt    1980
gctgaattgc catagggcac aaagactctt ctgtttgcat atcttctcag gaaattaaaa    2040
ttgtatcaca tgtatttata agaa                                           2064
```

<210> SEQ ID NO 13
<211> LENGTH: 151
<212> TYPE: PRT
<213> ORGANISM: Homo sapiens

<400> SEQUENCE: 13

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Phe His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Asp Ile Cys Gln Pro His Phe Pro Lys Asp
    130                 135                 140

Arg Gly Leu Asn Leu Leu Met
145                 150
```

<210> SEQ ID NO 14
<211> LENGTH: 1629
<212> TYPE: DNA
<213> ORGANISM: Homo sapiens

<400> SEQUENCE: 14

```
tttcctgggc ggggccaagg ctggggcagg ggagtcagca gaggcctcgc tcgggcgccc      60
agtggtcctg ccgcctggtc tcacctcgct atggttcgtc tgcctctgca gtgcgtcctc     120
tggggctgct tgctgaccgc tgtccatcca gaacccccca ctgcatgcag agaaaaacag     180
tacctaataa acagtcagtg ctgttctttg tgccagccag acagaaaact ggtgagtgac     240
tgcacagagt tcactgaaac ggaatgcctt ccttgcggtg aaagcgaatt cctagacacc     300
tggaacagag agacacactg ccaccagcac aaatactgcg accccaacct agggcttcgg     360
gtccagcaga agggcacctc agaaacagac accatctgca cctgtgaaga aggctggcac     420
tgtacgagtg aggcctgtga gctgtgtgtc ctgaccgct catgctcgcc cggctttggg     480
gtcaagcaga ttgctacagg ggtttctgat accatctgcg agccctgccc agtcggcttc     540
```

-continued

```
ttctccaatg tgtcatctgc tttcgaaaaa tgtcacccct ggacaagctg tgagaccaaa       600
gacctggttg tgcaacaggc aggcacaaac aagactgatg ttgtctgtgg tccccaggat       660
cggctgagag ccctggtggt gatccccatc atcttcggga tcctgtttgc catcctcttg       720
gtgctggtct ttatcaaaaa ggtggccaag aagccaacca ataaggcccc caccccaag       780 caggaacccc aggagatcaa ttttcccgac gatcttcctg ctccaacac tgctgctcca       840 gtgcaggaga ctttacatgg atgccaaccg gtcacccagg aggatggcaa agagagtcgc       900
atctcagtgc aggagagaca gtgaggctgc acccacccag gagtgtggcc acgtgggcaa       960
acaggcagtt ggccagagag cctggtgctg ctgctgctgt ggcgtgaggg tgaggggctg      1020
gcactgactg ggcatagctc cccgcttctg cctgcacccc tgcagtttga cacaggagac      1080
ctggcactgg atgcagaaac agttcacctt gaagaacctc tcacttcacc ctggagccca      1140
tccagtctcc caacttgtat taaagacaga ggcagaagtt tggtggtggt ggtgttgggg      1200
tatggtttag taatatccac cagaccttcc gatccagcag tttggtgccc agagaggcat      1260
catggtggct tccctgcgcc caggaagcca tatacacaga tgcccattgc agcattgttt      1320
gtgatagtga acaactggaa gctgcttaac tgtccatcag caggagactg gctaaataaa      1380
attagaatat atttatacaa cagaatctca aaaacactgt tgagtaagga aaaaaaggca      1440
tgctgctgaa tgatgggtat ggaactttt aaaaaagtac atgctttat gtatgtatat      1500 tgcctatgga tatatgtata aatacaatat gcatcatata ttgatataac aagggttctg      1560
gaagggtaca cagaaaaccc acagctcgaa gagtggtgac gtctggggtg gggaagaagg      1620
gtctggggg                                                              1629
```

<210> SEQ ID NO 15
<211> LENGTH: 290
<212> TYPE: PRT
<213> ORGANISM: Homo sapiens

<400> SEQUENCE: 15

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

```
Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 16
<211> LENGTH: 873
<212> TYPE: DNA
<213> ORGANISM: Homo sapiens

<400> SEQUENCE: 16
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca gcgaattac tgtgaaagtc aatgccccat acaacaaaat caaccaaaga     420
attttggttg tggatccagt cacctctgaa catgaactga catgtcaggc tgagggctac     480
cccaaggccg aagtcatctg gacaagcagt gaccatcaag tcctgagtgg taagaccacc     540
accaccaatt ccaagagaga ggagaagctt tcaatgtga ccagcacact gagaatcaac     600
acaacaacta tgagattttt ctactgcact tttaggagat tagatcctga ggaaaaccat     660
acagctgaat tggtcatccc agaactacct ctggcacatc ctccaaatga aggactcac     720 ttggtaattc tgggagccat cttattatgc cttggtgtag cactgacatt catcttccgt     780
ttaagaaaag ggagaatgat ggatgtgaaa aatgtggca tccaagatac aaactcaaag     840
aagcaaagtg atacacattt ggaggagacg taa                                    873

<210> SEQ ID NO 17
<211> LENGTH: 534
<212> TYPE: PRT
<213> ORGANISM: Homo sapiens

<400> SEQUENCE: 17

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45
```

```
Cys Cys Ser Phe Ser Pro Glu Pro Gly Phe Ser Leu Ala Gln Leu Asn
    50              55                  60

Leu Ile Trp Gln Leu Thr Asp Thr Lys Gln Leu Val His Ser Phe Ala
65              70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
            115                 120                 125

Phe Gly Ser Ala Ala Val Ser Leu Gln Val Ala Ala Pro Tyr Ser Lys
        130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
450                 455                 460
```

```
Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
                500                 505                 510

Ser Lys Thr Ala Leu Gln Pro Leu Lys His Ser Asp Ser Lys Glu Asp
                515                 520                 525

Asp Gly Gln Glu Ile Ala
    530

<210> SEQ ID NO 18
<211> LENGTH: 3222
<212> TYPE: DNA
<213> ORGANISM: Homo sapiens

<400> SEQUENCE: 18
cttccaccac ggggagccca gctgtcagcc gcctcacagg aagatgctgc gtcggcgggg     60
cagccctggc atgggtgtgc atgtgggtgc agccctggga gcactgtggt tctgcctcac    120
aggagccctg gaggtccagg tccctgaaga cccagtggtg gcactggtgg caccgatgc     180 caccctgtgc tgctccttct cccccgagcc tggcttcagc ctggcacagc tcaacctcat    240
ctggcagctg acagatacca aacagctggt gcacagcttt gctgagggcc aggaccaggg    300
cagcgcctat gccaaccgca cggccctctt cccggacctg ctggcacagg caacgcatc    360 cctgaggctg cagcgcgtgc gtgtggcgga cgagggcagc ttcacctgct tcgtgagcat    420
ccgggatttc ggcagcgctg ccgtcagcct gcaggtggcc gctccctact cgaagcccag    480 catgacccctg gagcccaaca aggacctgcg gccaggggac acggtgacca tcacgtgctc    540
cagctaccag ggctaccctg aggctgaggt gttctggcag gatgggcagg gtgtgcccct    600
gactggcaac gtgaccacgt cgcagatggc caacgagcag ggcttgtttg atgtgcacag    660
catcctgcgg gtggtgctgg gtgcaaatgg cacctacagc tgcctggtgc gcaacccgt    720 gctgcagcag gatgcgcaca gctctgtcac catcacaccc agagaagcc ccacaggagc    780 cgtggaggtc caggtccctg aggacccggt ggtggcccta gtgggcaccg atgccaccct    840
gcgctgctcc ttctcccccg agcctggctt cagcctggca cagctcaacc tcatctggca    900
gctgacagac accaaacagc tggtgcacag tttcaccgaa ggcgggacc agggcagcgc    960 ctatgccaac cgcacggccc tcttcccgga cctgctggca caaggcaatg catccctgag   1020
gctgcagcgc gtgcgtgtgg cggacgaggg cagcttcacc tgcttcgtga gcatccggga   1080
tttcggcagc gctgccgtca gcctgcaggt ggccgctccc tactcgaagc ccagcatgac   1140
cctggagccc aacaaggacc tgcggccagg ggacacggtg accatcacgt gctccagcta   1200
ccggggctac cctgaggctg aggtgttctg gcaggatggg cagggtgtgc ccctgactgg   1260
caacgtgacc acgtcgcaga tggccaacga gcagggcttg tttgatgtgc acagcgtcct   1320
gcgggtggtg ctgggtgcga atggcaccta cagctgcctg gtgcgcaacc ccgtgctgca   1380
gcaggatgcg cacggctctg tcaccatcac agggcagcct atgacattcc ccccagaggc   1440
cctgtgggtg accgtggggc tgtctgtctg tctcattgca ctgctggtgg ccctggcttt   1500
cgtgtgctgg agaaagatca aacagagctg tgaggaggag aatgcaggag ctgaggacca   1560
ggatggggag ggagaaggct ccaagacagc cctgcagcct ctgaaacact ctgacagcaa   1620
agaagatgat ggacaagaaa tagcctgacc atgaggacca gggagctgct accctccct   1680
```

```
acagctccta cccctctggct gcaatggggc tgcactgtga gccctgcccc caacagatgc    1740
atcctgctct gacaggtggg ctccttctcc aaaggatgcg gtacacagac cactgtgcag    1800
ccttatttct ccaatggaca tgattcccaa gtcatcctgc tgccttttt cttatagaca     1860
caatgaacag accacccaca acctagttc tctaagtcat cctgcctgct gccttatttc     1920
acagtacata catttcttag ggacacagta cactgaccac atcaccaccc tcttcttcca    1980
gtgctgcgtg gaccatctgg ctgccttttt tctccaaaag atgcaatatt cagactgact    2040
gaccccctgc cttatttcac caaagacacg atgcatagtc accccggcct tgtttctcca    2100
atggccgtga tacactagtg atcatgttca gccctgcttc cacctgcata gaatcttttc    2160
ttctcagaca gggacagtgc ggcctcaaca tctcctggag tctagaagct gtttcctttc    2220
ccctccttcc tcctcttgct ctagccttaa tactggcctt ttccctccct gccccaagtg    2280
aagacagggc actctgcgcc caccacatgc acagctgtgc atggagacct gcaggtgcac    2340
gtgctggaac acgtgtggtt ccccctggc ccagcctcct ctgcagtgcc cctctcccct     2400
gcccatcctc cccacggaag catgtgctgg tcacactggt tctccagggg tctgtgatgg    2460
ggccctggg ggtcagcttc tgtccctctg ccttctcacc tctttgttcc tttcttttca    2520
tgtatccatt cagttgatgt ttattgagca actacagatg tcagcactgt gttaggtgct    2580
ggggccctg cgtgggaaga taaagttcct ccctcaagga ctccccatcc agctgggaga    2640
cagacaacta actacactgc accctgcggt ttgcaggggg ctcctgcctg gctccctgct    2700
ccacacctcc tctgtggctc aaggcttcct ggatacctca ccccatccc acccataatt     2760
cttacccaga gcatggggtt ggggcggaaa cctggagaga gggacatagc ccctcgccac    2820
ggctagagaa tctggtggtg tccaaaatgt ctgtccaggt gtgggcaggt gggcaggcac    2880
caaggccctc tggaccttc atagcagcag aaaaggcaga gcctggggca gggcagggcc    2940
aggaatgctt tggggacacc gaggggactg ccccccacc cccaccatgg tgctattytg     3000
gggctggggc agtcttttcc tggcttgcct ctggccagct cctggcctct ggtagagtga    3060
gacttcagac gttytgatgc cttccggatg tcatctctcc ctgccccagg aatggaagat    3120
gtgaggactt ytaatttaaa tgtgggactc ggagggattt tgtaaactgg gggtatattt    3180
tggggaaaat aaatgtcttt gtaaaaaaaa aaaaaaaaa aa                        3222
```

<210> SEQ ID NO 19
<211> LENGTH: 241
<212> TYPE: PRT
<213> ORGANISM: Homo sapiens

<400> SEQUENCE: 19

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
                20                  25                  30

Ser Cys Asp Val Gln Leu Tyr Ile Lys Arg Gln Ser Glu His Ser Ile
            35                  40                  45

Leu Ala Gly Asp Pro Phe Glu Leu Glu Cys Pro Val Lys Tyr Cys Ala
        50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser

```
            100                 105                 110
Tyr Arg Cys Ser Ala Asn Phe Gln Ser Asn Leu Ile Glu Ser His Ser
        115                 120                 125

Thr Thr Leu Tyr Val Thr Gly Lys Gln Asn Glu Leu Ser Asp Thr Ala
    130                 135                 140

Gly Arg Glu Ile Asn Leu Val Asp Ala His Leu Lys Ser Glu Gln Thr
145                 150                 155                 160

Glu Ala Ser Thr Arg Gln Asn Ser Gln Val Leu Leu Ser Glu Thr Gly
                165                 170                 175

Ile Tyr Asp Asn Asp Pro Asp Leu Cys Phe Arg Met Gln Glu Gly Ser
            180                 185                 190

Glu Val Tyr Ser Asn Pro Cys Leu Glu Glu Asn Lys Pro Gly Ile Val
        195                 200                 205

Tyr Ala Ser Leu Asn His Ser Val Ile Gly Leu Asn Ser Arg Leu Ala
    210                 215                 220

Arg Asn Val Lys Glu Ala Pro Thr Glu Tyr Ala Ser Ile Cys Val Arg
225                 230                 235                 240

Ser

<210> SEQ ID NO 20
<211> LENGTH: 870
<212> TYPE: DNA
<213> ORGANISM: Homo sapiens

<400> SEQUENCE: 20
atgaagacat tgcctgccat gcttggaact gggaaattat tttgggtctt cttcttaatc      60
ccatatctgg acatctggaa catccatggg aagaatcat gtgatgtaca gctttatata     120
aagagacaat ctgaacactc catcttagca ggagatccct ttgaactaga atgccctgtg     180
aaatactgtg ctaacaggcc tcatgtgact tggtgcaagc tcaatggaac aacatgtgta     240
aaacttgaag atagacaaac aagttggaag gaagagaaga acatttcatt tttcattcta     300 catttttgaac cagtgcttcc taatgacaat gggtcatacc gctgttctgc aaattttcag     360
tctaatctca ttgaaagcca ctcaacaact ctttatgtga cagatgtaaa aagtgcctca     420
gaacgaccct ccaaggacga aatggcaagc agaccctggc tcctgtatag tttacttcct     480 ttgggggat tgcctctact catcactacc tgtttctgcc tgttctgctg cctgagaagg     540
caccaaggaa agcaaaatga actctctgac acagcaggaa gggaaattaa cctggttgat     600
gctcacctta agagtgagca aacagaagca agcaccaggc aaaattccca agtactgcta     660
tcagaaactg gaatttatga taatgaccct gacctttgtt tcaggatgca ggaagggtct     720
gaagtttatt ctaatccatg cctggaagaa acaaaccag gcattgttta tgcttccctg     780
aaccattctg tcattggact gaactcaaga ctggcaagaa atgtaaaaga agcaccaaca     840
gaatatgcat ccatatgtgt gaggagttaa                                       870

<210> SEQ ID NO 21
<211> LENGTH: 293
<212> TYPE: PRT
<213> ORGANISM: Homo sapiens

<400> SEQUENCE: 21

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30
```

```
Cys Asn Asp Thr Val Val Ile Pro Cys Phe Val Thr Asn Met Glu Ala
         35                  40                  45
Gln Asn Thr Thr Glu Val Tyr Val Lys Trp Lys Phe Lys Gly Arg Asp
     50                  55                  60
Ile Tyr Thr Phe Asp Gly Ala Leu Asn Lys Ser Thr Val Pro Thr Asp
 65                  70                  75                  80
Phe Ser Ser Ala Lys Ile Glu Val Ser Gln Leu Leu Lys Gly Asp Ala
             85                  90                  95
Ser Leu Lys Met Asp Lys Ser Asp Ala Val Ser His Thr Gly Asn Tyr
            100                 105                 110
Thr Cys Glu Val Thr Glu Leu Thr Arg Glu Gly Glu Thr Ile Ile Glu
        115                 120                 125
Leu Lys Tyr Arg Val Val Ser Trp Phe Ser Pro Asn Glu Asn Ile Leu
    130                 135                 140
Ile Val Ile Phe Pro Ile Phe Ala Ile Leu Leu Phe Trp Gly Gln Phe
145                 150                 155                 160
Gly Ile Lys Thr Leu Lys Tyr Arg Ser Gly Gly Met Asp Glu Lys Thr
                165                 170                 175
Ile Ala Leu Leu Val Ala Gly Leu Val Ile Thr Val Ile Val Ile Val
            180                 185                 190
Gly Ala Ile Leu Phe Val Pro Gly Glu Tyr Ser Leu Lys Asn Ala Thr
        195                 200                 205
Gly Leu Gly Leu Ile Val Thr Ser Thr Gly Ile Leu Ile Leu Leu His
    210                 215                 220
Tyr Tyr Val Phe Ser Thr Ala Ile Gly Leu Thr Ser Phe Val Ile Ala
225                 230                 235                 240
Ile Leu Val Ile Gln Val Ile Ala Tyr Ile Leu Ala Val Val Gly Leu
                245                 250                 255
Ser Leu Cys Ile Ala Ala Cys Ile Pro Met His Gly Pro Leu Leu Ile
            260                 265                 270
Ser Gly Leu Ser Ile Leu Ala Leu Ala Gln Leu Leu Gly Leu Val Tyr
        275                 280                 285
Met Lys Phe Val Glu
    290
```

<210> SEQ ID NO 22
<211> LENGTH: 996
<212> TYPE: DNA
<213> ORGANISM: Homo sapiens

<400> SEQUENCE: 22

```
atgtggcccc tggtagcggc gctgttgctg ggctcggcgt gctgcggatc agctcagcta    60
ctatttaata aaacaaaatc tgtagaattc acgttttgta atgacactgt cgtcattcca   120
tgctttgtta ctaatatgga ggcacaaaac actactgaag tatacgtaaa gtggaaattt   180
aaaggaagag atatttacac ctttgatgga gctctaaaca gtccactgt ccccactgac    240
tttagtagtg caaaaattga agtctcacaa ttactaaaag gagatgcctc tttgaagatg   300
gataagagtg atgctgtctc acacacagga aactacactt gtgaagtaac agaattaacc   360
agagaaggtg aaacgatcat cgagctaaaa tatcgtgttg tttcatggtt ttctccaaat   420
gaaaatattc ttattgttat tttcccaatt tttgctatac tcctgttctg gggacagttt   480
ggtattaaaa cacttaaata tagatccggt ggtatggatg agaaaacaat tgctttactt   540
gttgctggac tagtgatcac tgtcattgtc attgttggag ccattctttt cgtcccaggt   600
```

```
gaatattcat taaagaatgc tactggcctt ggtttaattg tgacttctac agggatatta    660
atattacttc actactatgt gtttagtaca gcgattggat taacctcctt cgtcattgcc    720
atattggtta ttcaggtgat agcctatatc ctcgctgtgg ttggactgag tctctgtatt    780
gcggcgtgta taccaatgca tggccctctt ctgatttcag gtttgagtat cttagctcta    840
gcacaattac ttggactagt ttatatgaaa tttgtggaat aactgaagtg aagtgatgga    900
ctccgatttg gagagtagta agacgtgaaa ggaatacact tgtgtttaag caccatggcc    960
ttgatgattc actgttgggg agaagaaaca agaaaa                              996
```

<210> SEQ ID NO 23
<211> LENGTH: 281
<212> TYPE: PRT
<213> ORGANISM: Homo sapiens

<400> SEQUENCE: 23

```
Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Pro Pro Pro
        35                  40                  45

Pro Pro Pro Pro Pro Leu Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280
```

<210> SEQ ID NO 24

<211> LENGTH: 972
<212> TYPE: DNA
<213> ORGANISM: Homo sapiens

<400> SEQUENCE: 24

```
tctagactca ggactgagaa gaagtaaaac cgtttgctgg ggctggcctg actcaccagc      60
tgccatgcag cagcccttca attacccata tccccagatc tactgggtgg acagcagtgc     120
cagctctccc tgggcccctc caggcacagt tcttccctgt ccaacctctg tgcccagaag     180
gcctggtcaa aggaggccac caccaccacc gccaccgcca ccactaccac ctccgccgcc     240
gccgccacca ctgcctccac taccgctgcc acccctgaag aagagaggga accacagcac     300
aggcctgtgt ctccttgtga tgttttttcat ggttctggtt gccttggtag gattgggcct     360
ggggatgttt cagctcttcc acctacagaa ggagctggca gaactccgag agtcctaccag     420
ccagatgcac acagcatcat ctttggagaa gcaaataggc caccccagtc cacccccctga     480
aaaaaaggag ctgaggaaag tggcccattt aacaggcaag tccaactcaa ggtccatgcc     540
tctggaatgg gaagacacct atggaattgt cctgctttct ggagtgaagt ataagaaggg     600
tggccttgtg atcaatgaaa ctgggctgta ctttgtatat tccaaagtat acttccgggg     660
tcaatcttgc aacaacctgc ccctgagcca caaggtctac atgaggaact ctaagtatcc     720
ccaggatctg gtgatgatgg aggggaagat gatgagctac tgcactactg ggcagatgtg     780
ggcccgcagc agctacctgg gggcagtgtt caatcttacc agtgctgatc atttatatgt     840
caacgtatct gagctctctc tggtcaattt tgaggaatct cagacgtttt tcggcttata     900
taagctctaa gagaagcact ttgggattct ttccattatg attctttgtt acaggcaccg     960
agatgttcta ga                                                         972
```

<210> SEQ ID NO 25
<211> LENGTH: 283
<212> TYPE: PRT
<213> ORGANISM: Homo sapiens

<400> SEQUENCE: 25

```
Met Glu Pro Pro Gly Asp Trp Gly Pro Pro Trp Arg Ser Thr Pro
1               5                   10                  15

Arg Thr Asp Val Leu Arg Leu Val Leu Tyr Leu Thr Phe Leu Gly Ala
                20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
        50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
```

```
              165                 170                 175
Glu Glu Cys Gln His Gln Thr Lys Cys Ser Trp Leu Val Thr Lys Ala
            180                 185                 190

Gly Ala Gly Thr Ser Ser His Trp Val Trp Phe Leu Ser Gly
            195                 200             205

Ser Leu Val Ile Val Ile Val Cys Ser Thr Val Gly Leu Ile Ile Cys
            210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
            275                 280
```

<210> SEQ ID NO 26
<211> LENGTH: 1724
<212> TYPE: DNA
<213> ORGANISM: Homo sapiens

<400> SEQUENCE: 26

```
ccttcatacc ggcccttccc ctcggctttg cctggacagc tcctgcctcc cgcagggccc    60
acctgtgtcc cccagcgccg ctccacccag caggcctgag cccctctctg ctgccagaca   120
cccccctgctg cccactctcc tgctgctcgg gttctgaggc acagcttgtc acaccgaggc  180
ggattctctt tctctttctc ttctggccca cagccgcagc aatggcgctg agttcctctg   240
ctggagttca tcctgctagc tgggttcccg agctgccggt ctgagcctga ggcatggagc   300
ctcctggaga ctgggggcct cctccctgga gatccacccc cagaaccgac gtcttgaggc   360
tggtgctgta tctcaccttc ctgggagccc cctgctacgc cccagctctg ccgtcctgca   420
aggaggacga gtacccagtg ggctccgagt gctgccccaa gtgcagtcca ggttatcgtg   480
tgaaggaggc ctgcggggag ctgacgggca cagtgtgtga accctgccct ccaggcacct   540
acattgccca cctcaatggc ctaagcaagt gtctgcagtg ccaaatgtgt gacccagcca   600
tgggcctgcg cgcgagccgg aactgctcca ggacagagaa cgccgtgtgt ggctgcagcc   660
caggccactt ctgcatcgtc caggacgggg accactgcgc cgcgtgccgc gcttacgcca   720
cctccagccc gggccagagg gtgcagaagg aggcaccga gagtcaggac accctgtgtc   780
agaactgccc cccgggggacc ttctctccca atgggaccct ggaggaatgt cagcaccaga   840
ccaagtgcag ctggctggtg acgaaggccg agctgggac cagcagctcc cactgggtat   900
ggtggtttct ctcagggagc ctcgtcatcg tcattgtttg ctccacagtt ggcctaatca   960
tatgtgtgaa aagaagaaag ccaagggtg atgtagtcaa ggtgatcgtc tccgtccagc  1020
ggaaaagaca ggaggcagaa ggtgaggcca cagtcattga ggccctgcag gcccctccgg  1080
acgtcaccac ggtggccgtg gaggagacaa taccctcatt cacggggagg agcccaaacc  1140
actgacccac agactctgca ccccgacgcc agagatacct ggagcgacgg ctgctgaaag  1200
aggctgtcca cctggcgaaa ccaccggagc ccggaggctt gggggctccg ccctgggctg  1260
gcttccgtct cctccagtgg agggagaggt ggggcccctg ctggggtaga gctggggacg  1320
ccacgtgcca ttcccatggg ccagtgaggg cctgggggcct ctgttctgct gtggcctgag  1380
ctccccagag tcctgaggag gagcgccagt tgcccctcgc tcacagacca cacccagc    1440
```

-continued

```
cctcctgggc cagcccagag ggcccttcag accccagctg tctgcgcgtc tgactcttgt    1500
ggcctcagca ggacaggccc cgggcactgc ctcacagcca aggctggact gggttggctg    1560
cagtgtggtg tttagtggat accacatcgg aagtgatttt ctaaattgga tttgaattcc    1620
ggtcctgtct tctatttgtc atgaaacagt gtatttgggg agatgctgtg ggaggatgta    1680
aatatcttgt ttctcctcaa aaaaaaaaaa aaaaaaaaa aaaa                      1724
```

<210> SEQ ID NO 27
<211> LENGTH: 403
<212> TYPE: PRT
<213> ORGANISM: Homo sapiens

<400> SEQUENCE: 27

```
Met Ala His Ala Met Glu Asn Ser Trp Thr Ile Ser Lys Glu Tyr His
1               5                   10                  15

Ile Asp Glu Glu Val Gly Phe Ala Leu Pro Asn Pro Gln Glu Asn Leu
            20                  25                  30

Pro Asp Phe Tyr Asn Asp Trp Met Phe Ile Ala Lys His Leu Pro Asp
        35                  40                  45

Leu Ile Glu Ser Gly Gln Leu Arg Glu Arg Val Glu Lys Leu Asn Met
    50                  55                  60

Leu Ser Ile Asp His Leu Thr Asp His Lys Ser Gln Arg Leu Ala Arg
65                  70                  75                  80

Leu Val Leu Gly Cys Ile Thr Met Ala Tyr Val Trp Gly Lys Gly His
                85                  90                  95

Gly Asp Val Arg Lys Val Leu Pro Arg Asn Ile Ala Val Pro Tyr Cys
            100                 105                 110

Gln Leu Ser Lys Lys Leu Glu Leu Pro Pro Ile Leu Val Tyr Ala Asp
        115                 120                 125

Cys Val Leu Ala Asn Trp Lys Lys Lys Asp Pro Asn Lys Pro Leu Thr
    130                 135                 140

Tyr Glu Asn Met Asp Val Leu Phe Ser Phe Arg Asp Gly Asp Cys Ser
145                 150                 155                 160

Lys Gly Phe Phe Leu Val Ser Leu Leu Val Glu Ile Ala Ala Ala Ser
                165                 170                 175

Ala Ile Lys Val Ile Pro Thr Val Phe Lys Ala Met Gln Met Gln Glu
            180                 185                 190

Arg Asp Thr Leu Leu Lys Ala Leu Leu Glu Ile Ala Ser Cys Leu Glu
        195                 200                 205

Lys Ala Leu Gln Val Phe His Gln Ile His Asp His Val Asn Pro Lys
    210                 215                 220

Ala Phe Phe Ser Val Leu Arg Ile Tyr Leu Ser Gly Trp Lys Gly Asn
225                 230                 235                 240

Pro Gln Leu Ser Asp Gly Leu Val Tyr Glu Gly Phe Trp Glu Asp Pro
                245                 250                 255

Lys Glu Phe Ala Gly Gly Ser Ala Gly Gln Ser Ser Val Phe Gln Cys
            260                 265                 270

Phe Asp Val Leu Leu Gly Ile Gln Gln Thr Ala Gly Gly Gly His Ala
        275                 280                 285

Ala Gln Phe Leu Gln Asp Met Arg Arg Tyr Met Pro Pro Ala His Arg
    290                 295                 300

Asn Phe Leu Cys Ser Leu Glu Ser Asn Pro Ser Val Arg Glu Phe Val
305                 310                 315                 320

Leu Ser Lys Gly Asp Ala Gly Leu Arg Glu Ala Tyr Asp Ala Cys Val
```

```
            325                 330                 335
Lys Ala Leu Val Ser Leu Arg Ser Tyr His Leu Gln Ile Val Thr Lys
        340                 345                 350

Tyr Ile Leu Ile Pro Ala Ser Gln Gln Pro Lys Glu Asn Lys Thr Ser
        355                 360                 365

Glu Asp Pro Ser Lys Leu Glu Ala Lys Gly Thr Gly Thr Asp Leu
    370                 375                 380

Met Asn Phe Leu Lys Thr Val Arg Ser Thr Thr Glu Lys Ser Leu Leu
385                 390                 395                 400

Lys Glu Gly

<210> SEQ ID NO 28
<211> LENGTH: 1944
<212> TYPE: DNA
<213> ORGANISM: Homo sapiens

<400> SEQUENCE: 28
aatttctcac tgcccctgtg ataaactgtg gtcactggct gtggcagcaa ctattataag     60
atgctctgaa aactcttcag acactgaggg gcaccagagg agcagactac aagaatggca    120
cacgctatgg aaaactcctg acaatcagt aaagagtacc atattgatga agaagtgggc     180
tttgctctgc caaatccaca ggaaaatcta cctgattttt ataatgactg gatgttcatt    240
gctaaacatc tgcctgatct catagagtct ggccagcttc gagaaagagt tgagaagtta    300
aacatgctca gcattgatca tctcacagac cacaagtcac agcgccttgc acgtctagtt    360
ctgggatgca tcaccatggc atatgtgtgg ggcaaaggtc atgagatgt ccgtaaggtc     420 ttgccaagaa atattgctgt tccttactgc caactctcca gaaaactgga actgcctcct    480
attttggttt atgcagactg tgtcttggca aactggaaga aaaaggatcc taataagccc    540
ctgacttatg agaacatgga cgttttgttc tcatttcgtg atggagactg cagtaaagga    600
ttcttcctgg tctctctatt ggtggaaata gcagctgctt ctgcaatcaa agtaattcct    660
actgtattca aggcaatgca aatgcaagaa cgggacactt tgctaaaggc gctgttggaa    720
atagcttctt gcttggagaa agcccttcaa gtgtttcacc aaatccacga tcatgtgaac    780
ccaaaagcat ttttcagtgt tcttcgcata tatttgtctg gctggaaagg caaccccag    840 ctatcagacg tctggtgta tgaagggttc tgggaagacc caaggagtt tgcaggggc     900 agtgcaggcc aaagcagcgt ctttcagtgc tttgacgtcc tgctgggcat ccagcagact    960
gctggtggag acatgctgc tcagttcctc caggacatga agatatat gccaccagct     1020 cacaggaact tcctgtgctc attagagtca atccctcag tccgtgagtt tgtcctttca     1080
aaaggtgatg ctggcctgcg ggaagcttat gacgcctgtg tgaaagctct ggtctccctg    1140
aggagctacc atctgcaaat cgtgactaag tacatcctga ttcctgcaag ccagcagcca    1200
aaggagaata gacctctga agaccctca aactggaag ccaaaggaac tggaggcact       1260
gatttaatga atttcctgaa gactgtaaga agtacaactg agaaatccct tttgaaggaa    1320
ggttaatgta acccaacaag agcacatttt atcatagcag agacatctgt atgcattcct    1380
gtcattaccc attgtaacag agccacaaac taatactatg caatgtttta ccaataatgc    1440
aatacaaaag acctcaaaat acctgtgcat ttcttgtagg aaaacaacaa aggtaatta    1500 tgtgtaatta tactagaagt tttgtaatct gtatcttatc attggaataa aatgacattc    1560
aataaataaa aatgcataag atatattctg tcggctgggc gcggtggctc acgcctgtaa    1620
tcccagcact ttgggaggcc gaggcgggcg gatcacaagg tcaggagatc gagaccatct    1680
```

```
tggctaacac ggtgaaaccc cgtctctact aaaaatacaa aaaattagcc gggcgcggtg    1740
gcgggcacct gtagtcccag ctactcggga ggctgaggca ggagaatggc gtgaacctgg    1800
gaggcggagc ttgcagtgag ccaagattgt gccactgcaa tccggcctgg gctaagagc    1860 gggactccgt ctcaaaaaaa aaaaaaaaaa gatatattct gtcataataa ataaaaatgc    1920
ataagatata aaaaaaaaaa aaaa                                           1944
```

<210> SEQ ID NO 29
<211> LENGTH: 431
<212> TYPE: PRT
<213> ORGANISM: Homo sapiens

<400> SEQUENCE: 29

```
Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
    65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
               100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
        130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320
```

```
Asn Ser Ser Ser Asp Gln Arg Gln Ala Cys Lys Lys His Glu Leu Tyr
            325                 330                 335

Val Ser Phe Arg Asp Leu Gly Trp Gln Asp Trp Ile Ile Ala Pro Glu
        340                 345                 350

Gly Tyr Ala Ala Tyr Tyr Cys Glu Gly Glu Cys Ala Phe Pro Leu Asn
    355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
            405                 410                 415

Leu Lys Lys Tyr Arg Asn Met Val Val Arg Ala Cys Gly Cys His
        420                 425                 430

<210> SEQ ID NO 30
<211> LENGTH: 1448
<212> TYPE: DNA
<213> ORGANISM: Homo sapiens

<400> SEQUENCE: 30
gtgaccgagc ggcgcggacg gccgcctgcc ccctctgcca cctggggcgg tgcgggcccg      60
gagcccggag cccgggtagc gcgtagagcc ggcgcgatgc acgtgcgctc actgcgagct     120
gcggcgccgc acagcttcgt ggcgctctgg gcacccctgt tcctgctgcg ctccgccctg     180
gccgacttca gcctggacaa cgaggtgcac tcgagcttca tccaccggcg cctccgcagc     240
caggagcggc gggagatgca cgcgcgagatc ctctccattt tgggcttgcc ccaccgcccg     300
cgcccgcacc tccagggcaa gcacaactcg gcacccatgt tcatgctgga cctgtacaac     360
gccatggcgg tggaggaggg cggcgggccc ggcggccagg gcttctccta cccctacaag     420
gccgtcttca gtacccaggg ccccccctct gccagcctgc aagatagcca tttcctcacc     480
gacgccgaca tggtcatgag cttcgtcaac ctcgtggaac atgacaagga attcttccac     540
ccacgctacc accatcgaga gttccggttt gatctttcca agatcccaga agggaagct     600 gtcacggcag ccgaattccg gatctacaag gactacatcc gggaacgctt cgacaatgag     660
acgttccgga tcagcgttta tcaggtgctc caggagcact gggcaggga atcggatctc     720 ttcctgctcg acagccgtac cctctgggcc tcggaggagg ctggctggt gtttgacatc     780 acagccacca gcaaccactg ggtggtcaat ccgcggcaca acctgggcct gcagctctcg     840
gtggagacgc tggatgggca gagcatcaac cccaagttgg cggccctgat tgggcggcac     900 gggcccaga caagcagcc cttcatggtg gcttttcttca aggccacgga ggtccacttc     960
cgcagcatcc ggtccacggg gagcaaacag cgcagccaga accgctccaa gacgccaag    1020 aaccaggaag ccctgcggat ggccaacgtg cagagaaca gcagcagcga ccagaggcag    1080
gcctgtaaga agcacgagct gtatgtcagc ttccgagacc tggctggca ggactggatc    1140 atcgcgcctg aaggctacgc cgcctactac tgtgaggggg agtgtgcctt ccctctgaac    1200
tcctacatga acgccaccaa ccacgccatc gtgcagacgc tggtccactt catcaacccg    1260
gaaacggtgc ccaagccctg ctgtgcgccc acgcagctca atgccatctc cgtcctctac    1320
ttcgatgaca gtccaacgt catcctgaag aaatacagaa acatggtggt ccgggcctgt    1380
ggctgccact agctcctccg agaattcaga ccctttgggg ccaagttttt ctggatcctc    1440
cattgctc                                                             1448
```

<210> SEQ ID NO 31
<211> LENGTH: 178
<212> TYPE: PRT
<213> ORGANISM: Homo sapiens

<400> SEQUENCE: 31

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 32
<211> LENGTH: 1629
<212> TYPE: DNA
<213> ORGANISM: Homo sapiens

<400> SEQUENCE: 32
acacatcagg ggcttgctct tgcaaaacca aaccacaaga cagacttgca aaagaaggca     60
tgcacagctc agcactgctc tgttgcctgg tcctcctgac tggggtgagg gccagcccag    120
gccagggcac ccagtctgag aacagctgca cccacttccc aggcaacctg cctaacatgc    180
ttcgagatct ccgagatgcc ttcagcagag tgaagacttt cttctaaatg aaggatcagc    240
tggacaactt gttgttaaag gagtccttgc tggaggactt aagggttac ctgggttgcc     300 aagccttgtc tgagatgatc cagttttacc tggaggaggt gatgcccaa gctgagaacc      360 aagacccaga catcaaggcg catgtgaact ccctggggga gaacctgaag accctcaggc    420
tgaggctacg gcgctgtcat cgatttcttc cctgtgaaaa caagagcaag gccgtggagc    480
aggtgaagaa tgcctttaat aagctccaag agaaaggcat ctacaaagcc atgagtgagt    540
ttgacatctt catcaactac atagaagcct acatgacaat gaagatacga aactgagaca    600
tcagggtggc gactctatag actctaggac ataaattaga ggtctccaaa atcggatctg    660
gggctctggg atagctgacc cagccccttg agaaacctta ttgtacctct cttatagaat    720
atttattacc tctgatacct caaccccat ttcatttat ttactgagct ctctctgtgaa     780 cgatttagaa agaagcccaa tattataatt tttttcaata tttattattt tcacctgttt    840

```
ttaagctgtt tccatagggt gacacactat ggtatttgag tgttttaaga taaattataa      900
gttacataag ggaggaaaaa aaatgttctt tggggagcca acagaagctt ccattccaag      960
cctgaccacg ctttctagct gttgagctgt tttccctgac ctccctctaa tttatcttgt     1020
ctctgggctt ggggcttcct aactgctaca aatactctta ggaagagaaa ccagggagcc     1080
cctttgatga ttaattcacc ttccagtgtc tcggagggat tcccctaacc tcattcccca     1140
accacttcat tcttgaaagc tgtggccagc ttgttattta taacaaccta aatttggttc     1200
taggccgggc gcggtggctc acgcctgtaa tcccagcact ttgggaggct gaggcgggtg     1260
gatcacttga ggtcaggagt tcctaaccag cctggtcaac atggtgaaac cccgtctcta     1320
ctaaaaatac aaaaattagc cgggcatggt ggcgcgcacc tgtaatccca gctacttggg     1380
aggctgaggc aagagaattg cttgaaccca ggagatggaa gttgcagtga gctgatatca     1440
tgcccctgta ctccagcctg ggtgacagag caagactctg tctcaaaaaa taaaaataaa     1500
aataaatttg ttctaatag aactcagttt taactagaat ttattcaatt cctctgggaa      1560
tgttacattg tttgtctgtc ttcatagcag attttaatttt tgaataaata aatgtatctt    1620
attcacatc                                                             1629
```

<210> SEQ ID NO 33
<211> LENGTH: 770
<212> TYPE: PRT
<213> ORGANISM: Homo sapiens

<400> SEQUENCE: 33

```
Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
```

```
            225                 230                 235                 240
Ala Asp Trp Lys Arg Arg Gln Gln Ile Ala Cys Ile Gly Gly Pro Pro
                    245                 250                 255

Asn Ile Cys Leu Asp Arg Leu Glu Asn Trp Ile Thr Ser Leu Ala Glu
                260                 265                 270

Ser Gln Leu Gln Thr Arg Gln Ile Lys Lys Leu Glu Glu Leu Gln
            275                 280                 285

Gln Lys Val Ser Tyr Lys Gly Asp Pro Ile Val Gln His Arg Pro Met
        290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                    325                 330                 335

Leu Val Ile Lys Thr Gly Val Gln Phe Thr Thr Lys Val Arg Leu Leu
                340                 345                 350

Val Lys Phe Pro Glu Leu Asn Tyr Gln Leu Lys Ile Lys Val Cys Ile
            355                 360                 365

Asp Lys Asp Ser Gly Asp Val Ala Ala Leu Arg Gly Ser Arg Lys Phe
370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                    405                 410                 415

Arg Cys Gly Asn Gly Gly Arg Ala Asn Cys Asp Ala Ser Leu Ile Val
                420                 425                 430

Thr Glu Glu Leu His Leu Ile Thr Phe Glu Thr Glu Val Tyr His Gln
            435                 440                 445

Gly Leu Lys Ile Asp Leu Glu Thr His Ser Leu Pro Val Val Val Ile
        450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                    485                 490                 495

Pro Ile Gly Thr Trp Asp Gln Val Ala Glu Val Leu Ser Trp Gln Phe
                500                 505                 510

Ser Ser Thr Thr Lys Arg Gly Leu Ser Ile Glu Gln Leu Thr Thr Leu
            515                 520                 525

Ala Glu Lys Leu Leu Gly Pro Gly Val Asn Tyr Ser Gly Cys Gln Ile
        530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                    565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
            595                 600                 605

Arg Phe Ser Glu Ser Ser Lys Glu Gly Gly Val Thr Phe Thr Trp Val
        610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                    645                 650                 655
```

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
    675                 680                 685

Pro Glu Ser Gln Glu His Pro Glu Ala Asp Pro Gly Ser Ala Ala Pro
690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met
    770

<210> SEQ ID NO 34
<211> LENGTH: 4978
<212> TYPE: DNA
<213> ORGANISM: Homo sapiens

<400> SEQUENCE: 34

```
ggtttccgga gctgcggcgg cgcagactgg gaggggagc cggggttcc gacgtcgcag      60
ccgagggaac aagccccaac cggatcctgg acaggcaccc cggcttggcg ctgtctctcc    120
ccctcggctc ggagaggccc ttcggcctga gggagcctcg ccgcccgtcc ccggcacacg    180
cgcagccccg gcctctcggc ctctgccgga gaaacagttg ggaccctga ttttagcagg     240
atgcccaat ggaatcagct acagcagctt gacacacggt acctggagca gctccatcag    300
ctctacagtg acagcttccc aatggagctg cggcagtttc tggcccttg gattgagagt    360
caagattggg catatgcggc cagcaaagaa tcacatgcca ctttggtgtt tcataatctc    420
ctgggagaga ttgaccagca gtatagccgc ttcctgcaag agtcgaatgt tctctatcag    480
cacaatctac gaagaatcaa gcagtttctt cagagcaggt atcttgagaa gccaatggag    540
attgcccgga ttgtggcccg gtgcctgtgg gaagaatcac gccttctaca gactgcagcc    600
actgcggccc agcaaggggg ccaggccaac caccccacag cagccgtggt gacggagaag    660
cagcagatgc tggagcagca ccttcaggat gtccggaaga gagtgcagga tctagaacag    720
aaaatgaaag tggtagagaa tctccaggat gactttgatt tcaactataa accctcaag    780
agtcaaggag acatgcaaga tctgaatgga acaaccagt cagtgaccag gcagaagatg    840
cagcagctgg aacagatgct cactgcgctg accagatgc ggagaagcat cgtgagtgag    900
ctggcgggc ttttgtcagc gatggagtac gtgcagaaaa ctctcacgga cgaggagctg    960
gctgactgga gaggcggca acagattgcc tgcattggag ccgcccaa catctgccta    1020
gatcggctag aaaactggat aacgtcatta gcagaatctc aacttcagac ccgtcaacaa    1080
attaagaaac tggaggagtt gcagcaaaaa gtttcctaca aggggaccc cattgtacag    1140
caccggccga tgctggagga gagaatcgtg gagctgttta gaaacttaat gaaaagtgcc    1200
tttgtggtgg agcggcagcc ctgcatgccc atgcatcctg accggcccct cgtcatcaag    1260
accggcgtcc agttcactac taaagtcagg ttgctggtca aattccctga gttgaattat    1320
cagcttaaaa ttaaagtgtg cattgacaaa gactctgggg acgttgcagc tctcagagga    1380
```

```
tcccggaaat ttaacattct gggcacaaac acaaaagtga tgaacatgga agaatccaac    1440
aacggcagcc tctctgcaga attcaaacac ttgaccctga gggagcagag atgtgggaat    1500
gggggccgag ccaattgtga tgcttccctg attgtgactg aggagctgca cctgatcacc    1560
tttgagaccg aggtgtatca ccaaggcctc aagattgacc tagagaccca ctccttgcca    1620
gttgtggtga tctccaacat ctgtcagatg ccaaatgcct gggcgtccat cctgtggtac    1680
aacatgctga ccaacaatcc caagaatgta aactttttta ccaagcccce aattggaacc    1740 tgggatcaag tggccgaggt cctgagctgg cagttctcct ccaccaccaa gcgaggactg    1800
agcatcgagc agctgactac actggcgaga aaactcttgg gacctggtgt gaattattca    1860
gggtgtcaga tcacatgggc taaattttgc aaagaaaaca tggctggcaa gggcttctcc    1920
ttctgggtct ggctggacaa tatcattgac cttgtgaaaa agtacatcct ggcccttggg    1980
aacgaagggt acatcatggg ctttatcagt aaggagcggg agcgggccat cttgagcact    2040
aagcctccag gcaccttcct gctaagatcc agtgaaagca gcaaagaagg aggcgtcact    2100
ttcacttggg tggagaagga catcagcggt aagacccaga tccagtccgt ggaaccatac    2160
acaaagcagc agctgaacaa catgtcattt gctgaaatca tcatgggcta taagatcatg    2220
gatgctacca atatcctggt gtctccactg gtctatctct atcctgacat tcccaaggag    2280
gaggcattcg gaaagtattg tcggccagag agccaggagc atcctgaagc tgacccaggt    2340
agcgctgccc catacctgaa gaccaagttt atctgtgtga caccaacgac ctgcagcaat    2400
accattgacc tgccgatgtc cccccgcact ttagattcat tgatgcagtt tggaaataat    2460
ggtgaaggtg ctgaaccctc agcaggaggg cagtttgagt ccctcacctt tgacatggag    2520
ttgacctcgg agtgcgctac ctcccccatg tgaggagctg agaacggaag ctgcagaaag    2580
atacgactga ggcgcctacc tgcattctgc caccccteac acagccaaac cccagatcat    2640
ctgaaactac taactttgtg gttccagatt ttttttaatc tcctacttct gctatctttg    2700
agcaatctgg gcacttttaa aaatagagaa atgagtgaat gtgggtgatc tgcttttatc    2760
taaatgcaaa taaggatgtg ttctctgaga cccatgatca ggggatgtgg cgggggtgg    2820 ctagagggag aaaaaggaaa tgtcttgtgt tgttttgttc ccctgccctc ctttctcagc    2880 agcttttttgt tattgttgtt gttgttctta gacaagtgcc tcctggtgcc tgcggcatcc    2940
ttctgcctgt ttctgtaagc aaatgccaca ggccacctat agctacatac tcctggcatt    3000 gcactttttta accttgctga catccaaata gaagatagga ctatctaagc cctaggtttc    3060 ttttttaaatt aagaaataat aacaattaaa gggcaaaaaa cactgtatca gcatagcctt    3120
tctgtattta agaaacttaa gcagccgggc atggtggctc acgcctgtaa tcccagcact    3180
ttgggaggcc gaggcggatc ataaggtcag gagatcaaga ccatcctggc taacacggtg    3240
aaaccccgtc tctactaaaa gtacaaaaaa ttagctgggt gtggtggtgg gcgcctgtag    3300
tcccagctac tcgggaggct gaggcaggag aatcgcttga acctgagagg cggaggttgc    3360
agtgagccaa aattgcacca ctgcacactg cactccatcc tgggcgacag tctgagactc    3420
tgtctcaaaa aaaaaaaaaa aaaaagaaa cttcagttaa cagcctcctt ggtgctttaa    3480
gcattcagct tccttcaggc tggtaattta tataatccct gaaacgggct tcaggtcaaa    3540
cccttaagac atctgaagct gcaacctggc ctttggtgtt gaaataggaa ggtttaagga    3600
gaatctaagc atttttagact ttttttttata aatagactta ttttcctttg taatgtattg    3660
gccttttagt gagtaaggct gggcagaggg tgcttacaac cttgactccc tttctccctg    3720
gacttgatct gctgtttcag aggctaggtt gtttctgtgg gtgccttatc agggctggga    3780
```

```
tacttctgat tctggcttcc ttcctgcccc accctcccga ccccagtccc cctgatcctg    3840
ctagaggcat gtctccttgc gtgtctaaag gtccctcatc ctgtttgttt taggaatcct    3900
ggtctcagga cctcatggaa gagaggggg agagagttac aggttggaca tgatgcacac    3960 tatgggccc cagcgacgtg tctggttgag ctcaggaat atggttctta gccagtttct    4020
tggtgatatc cagtggcact tgtaatgcg tcttcattca gttcatgcag ggcaaaggct    4080
tactgataaa cttgagtctg ccctcgtatg agggtgtata cctggcctcc ctctgaggct    4140
ggtgactcct ccctgctggg gccccacagg tgaggcagaa cagctagagg gcctccccgc    4200
ctgcccgcct tggctggcta gctcgcctct cctgtgcgta tgggaacacc tagcacgtgc    4260
tggatgggct gcctctgact cagaggcatg gccggatttg gcaactcaaa accaccttgc    4320
ctcagctgat cagagtttct gtggaattct gtttgttaaa tcaaattagc tggtctctga    4380 attaagggg agacgaccTT ctctaagatg aacagggttc gccccagtcc tcctgcctgg    4440
agacagttga tgtgtcatgc agagctctta cttctccagc aacactcttc agtacataat    4500
aagcttaact gataaacaga atatttagaa aggtgagact tgggcttacc attgggttta    4560
aatcataggg acctagggcg agggttcagg gcttctctgg agcagatatt gtcaagttca    4620
tggccttagg tagcatgtat ctggtcttaa ctctgattgt agcaaaagtt ctgagaggag    4680
ctgagccctg ttgtggccca ttaaagaaca gggtcctcag gccctgcccg cttcctgtcc    4740 actgcccct cccatcccc agcccagccg agggaatccc gtgggttgct tacctaccta    4800
taaggtggtt tataagctgc tgtcctggcc actgcattca aattccaatg tgtacttcat    4860
agtgtaaaaa tttatattat tgtgaggttt tttgtctttt tttttttttt tttttttgg    4920 tatattgctg tatctacttt aacttccaga aataaacgtt atataggaac cgtaaaaa     4978
```

<210> SEQ ID NO 35
<211> LENGTH: 273
<212> TYPE: PRT
<213> ORGANISM: Homo sapiens

<400> SEQUENCE: 35

```
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
                100                 105                 110

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
        130                 135                 140

Ala Thr Gly Tyr Pro Leu Ala Glu Val Ser Trp Pro Asn Val Ser Val
145                 150                 155                 160
```

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
                260                 265                 270

Ile

<210> SEQ ID NO 36
<211> LENGTH: 2418
<212> TYPE: DNA
<213> ORGANISM: Homo sapiens

<400> SEQUENCE: 36 gcaaaccttta agctgaatga acaactttc ttctcttgaa tatatcttaa cgccaaattt       60 tgagtgctt tttgttaccc atcctcatat gtcccagcta gaaagaatcc tgggttggag      120
ctactgcatg ttgattgttt tgttttcct tttggctgtt cattttggtg gctactataa      180
ggaaatctaa cacaaacagc aactgttttt tgttgtttac ttttgcatct ttacttgtgg     240
agctgtggca agtcctcata tcaaatacag aacatgatct tcctcctgct aatgttgagc     300
ctggaattgc agcttcacca gatagcagct ttattcacag tgacagtccc taaggaactg     360
tacataatag agcatggcag caatgtgacc ctggaatgca actttgacac tggaagtcat     420
gtgaaccttg agcaataac agccagtttg caaaaggtgg aaaatgatac atccccacac      480
cgtgaaagag ccactttgct ggaggagcag ctgcccctag gaaggcctc gttccacata      540 cctcaagtcc aagtgaggga cgaaggacag taccaatgca taatcatcta tgggtcgcc      600 tgggactaca gtacctgac tctgaaagtc aaagcttcct acaggaaaat aaacactcac      660
atcctaaagg ttccagaaac agatgaggta gagctcacct gccaggctac aggttatcct     720
ctggcagaag tatcctggcc aaacgtcagc gttcctgcca acaccagcca ctccaggacc     780
cctgaaggcc tctaccaggt caccagtgtt ctgcgcctaa agccaccccc tggcagaaac     840
ttcagctgtg tgttctggaa tactcacgtg agggaactta ctttggccag cattgacctt     900
caaagtcaga tggaacccag gacccatcca acttggctgc ttcacatttt catccccttc     960
tgcatcattg ctttcatttt catagccaca gtgatagccc taagaaaaca actctgtcaa    1020
aagctgtatt cttcaaaaga cacaacaaaa agacctgtca ccacaacaaa agggaagtg     1080 aacagtgcta tctgaacctg tggtcttggg agccagggtg acctgatatg acatctaaag    1140
aagcttctgg actctgaaca agaattcggt ggcctgcaga gcttgccatt tgcactttc    1200 aaatgccttt ggatgaccca gcactttaat ctgaaacctg caacaagact agccaacacc    1260
tggccatgaa acttgcccct tcactgatct ggactcacct ctggagccta tggctttaag    1320
caagcactac tgcactttac agaattaccc cactggatcc tggacccaca gaattccttc    1380
aggatccttc ttgctgccag actgaaagca aaggaatta tttcccctca agttttctaa     1440

-continued

```
gtgatttcca aaagcagagg tgtgtggaaa tttccagtaa cagaaacaga tgggttgcca    1500
atagagttat tttttatcta tagcttcctc tgggtactag aagaggctat tgagactatg    1560
agctcacaga cagggcttcg cacaaactca aatcataatt gacatgtttt atggattact    1620
ggaatcttga tagcataatg aagttgttct aattaacaga gagcatttaa atatacacta    1680
agtgcacaaa ttgtggagta aagtcatcaa gctctgtttt tgaggtctaa gtcacaaagc    1740
atttgtttta acctgtaatg gcaccatgtt taatggtggt ttttttttg aactacatct      1800 ttcctttaaa aattattggt ttcttttat ttgttttac cttagaaatc aattatatac       1860
agtcaaaaat atttgatatg ctcatacgtt gtatctgcag caatttcaga taagtagcta    1920
aaatggccaa agccccaaac taagcctcct tttctggccc tcaatatgac tttaaatttg    1980
acttttcagt gcctcagttt gcacatctgt aatacagcaa tgctaagtag tcaaggcctt    2040
tgataattgg cactatggaa atcctgcaag atcccactac atatgtgtgg agcagaaggg    2100
taactcggct acagtaacag cttaattttg ttaaatttgt tctttatact ggagccatga    2160
agctcagagc attagctgac ccttgaacta ttcaaatggg cacattagct agtataacag    2220
acttacatag gtgggcctaa agcaagctcc ttaactgagc aaaatttggg gcttatgaga    2280
atgaaagggt gtgaaattga ctaacagaca aatcatacat ctcagtttct caattctcat    2340
gtaaatcaga gaatgccttt aaagaataaa actcaattgt tattcttcaa cgttctttat    2400
atattctact tttgggta                                                   2418
```

<210> SEQ ID NO 37
<211> LENGTH: 223
<212> TYPE: PRT
<213> ORGANISM: Homo sapiens

<400> SEQUENCE: 37

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
```

```
              195                 200                 205
Pro Glu Cys Glu Lys Gln Phe Gln Pro Tyr Phe Ile Pro Ile Asn
        210                 215                 220
```

<210> SEQ ID NO 38
<211> LENGTH: 2025
<212> TYPE: DNA
<213> ORGANISM: Homo sapiens

<400> SEQUENCE: 38

```
cttctgtgtg tgcacatgtg taatacatat ctgggatcaa agctatctat ataaagtcct      60
tgattctgtg tgggttcaaa cacatttcaa agcttcagga tcctgaaagg ttttgctcta     120
cttcctgaag acctgaacac cgctcccata aagccatggc ttgccttgga tttcagcggc     180
acaaggctca gctgaacctg ctaccagga cctggccctg cactctcctg ttttttcttc     240
tcttcatccc tgtcttctgc aaagcaatgc acgtggccca gcctgctgtg gtactggcca     300
gcagccgagg catcgccagc tttgtgtgtg agtatgcatc tccaggcaaa gccactgagg     360
tccgggtgac agtgcttcgg caggctgaca gccaggtgac tgaagtctgt gcggcaacct     420
acatgatggg gaatgagttg accttcctag atgattccat ctgcacgggc acctccagtg     480
gaaatcaagt gaacctcact atccaaggac tgagggccat ggacacggga ctctacatct     540
gcaaggtgga gctcatgtac ccaccgccat actacctggg cataggcaac ggaacccaga     600
tttatgtaat tgatccagaa ccgtgcccag attctgactt cctcctctgg atccttgcag     660
cagttagttc ggggttgttt ttttatagct ttctcctcac agctgtttct ttgagcaaaa     720
tgctaaagaa aagaagccct cttacaacag gggtctatgt gaaaatgccc ccaacagagc     780
cagaatgtga aaagcaattt cagccttatt ttattcccat caattgagaa accattatga     840
agaagagagt ccatatttca atttccaaga gctgaggcaa ttctaacttt tttgctatcc     900
agctattttt atttgtttgt gcatttgggg ggaattcatc tctctttaat ataaagttgg     960
atgcggaacc caaattacgt gtactacaat ttaaagcaaa ggagtagaaa gacagagctg    1020
ggatgttttct gtcacatcag ctccactttc agtgaaagca tcacttggga ttaatatggg    1080
gatgcagcat tatgatgtgg gtcaaggaat taagttaggg aatggcacag cccaaagaag    1140
gaaaaggcag ggagcgaggg agaagactat attgtacaca ccttatattt acgtatgaga    1200
cgtttatagc cgaaatgatc ttttcaagtt aaattttatg ccttttatt cttaaacaaa    1260
tgtatgatta catcaaggct tcaaaaatac tcacatggct atgttttagc cagtgatgct    1320
aaaggttgta ttgcatatat acatatatat atatatatat atatatatat atatatatat    1380
atatatatat tttaatttga tagtattgtg catagagcca cgtatgtttt tgtgtatttg    1440
ttaatggttt gaatataaac actatatggc agtgtctttc caccttgggt cccagggaag    1500
ttttgtggag gagctcagga cactaataca ccaggtagaa cacaaggtca tttgctaact    1560
agcttggaaa ctggatgagg tcatagcagt gcttgattgc gtggaattgt gctgagttgg    1620
tgttgacatg tgctttgggg cttttacacc agttcctttc aatggtttgc aaggaagcca    1680
cagctggtgg tatctgagtt gacttgacag aacactgtct tgaagacaat ggcttactcc    1740
aggagaccca caggtatgac cttctaggaa gctccagttc gatgggccca attcttacaa    1800
acatgtggtt aatgccatgg acagaagaag gcagcaggtg cagaatggg gtgcatgaag     1860
gtttctgaaa attaacactg cttgtgtttt taactcaata ttttccatga aaatgcaaca    1920
acatgtataa tattttttaat taaataaaaa tctgtggtgg tcgttttaaa aaaaaaaaa    1980
```
aaaaaaaaaa aaaaaaaaaa aaaaaaaaaa aaaaaaaaaa aaaaa                2025

<210> SEQ ID NO 39
<211> LENGTH: 301
<212> TYPE: PRT
<213> ORGANISM: Homo sapiens

<400> SEQUENCE: 39

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Leu Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300
```

<210> SEQ ID NO 40
<211> LENGTH: 906
<212> TYPE: DNA
<213> ORGANISM: Homo sapiens

<400> SEQUENCE: 40
atgttttcac atcttcccctt tgactgtgtc ctgctgctgc tgctgctact acttacaagg    60
tcctcagaag tggaatacag agcggaggtc ggtcagaatg cctatctgcc ctgcttctac   120

```
acccccagccg ccccagggaa cctcgtgccc gtctgctggg gcaaaggagc ctgtcctgtg    180
tttgaatgtg gcaacgtggt gctcaggact gatgaaaggg atgtgaatta ttggacatcc    240
agatactggc taaatgggga tttccgcaaa ggagatgtgt ccctgaccat agagaatgtg    300
actctagcag acagtgggat ctactgctgc cggatccaaa tcccaggcat aatgaatgat    360
gaaaaattta acctgaagtt ggtcatcaaa ccagccaagg tcaccccctgc accgactctg    420 cagagagact tcactgcagc ctttccaagg atgcttacca ccaggggaca tggcccagca    480
gagacacaga cactggggag cctccctgat ataaatctaa cacaaatatc cacattggcc    540
aatgagttac gggactctag attggccaat gacttacggg actctggagc aaccatcaga    600
ataggcatct acatcggagc agggatctgt gctgggctgg ctctggctct tatcttcggc    660
gctttaattt tcaaatggta ttctcatagc aaagagaaga tacagaattt aagcctcatc    720
tctttggcca acctccctcc ctcaggattg gcaaatgcag tagcagaggg aattcgctca    780
gaagaaaaca tctataccat tgaagagaac gtatatgaag tggaggagcc caatgagtat    840
tattgctatg tcagcagcag gcagcaaccc tcacaacctt tgggttgtcg ctttgcaatg    900
ccatag                                                                906
```

<210> SEQ ID NO 41
<211> LENGTH: 525
<212> TYPE: PRT
<213> ORGANISM: Homo sapiens

<400> SEQUENCE: 41

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
```

```
                225                 230                 235                 240
Cys Ile Leu Thr Tyr Arg Asp Gly Phe Asn Val Ser Ile Met Tyr Asn
            245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Phe Leu Thr Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Gln Leu
        515                 520                 525

<210> SEQ ID NO 42
<211> LENGTH: 1995
<212> TYPE: DNA
<213> ORGANISM: Homo sapiens

<400> SEQUENCE: 42 acagggtga aggcccagag accagcagaa cggcatccca gccacgacgg ccactttgct      60
ctgtctgctc tccgccacgg ccctgctctg ttccctggga caccccgcc cccacctcct    120 caggctgcct gatctgccca gctttccagc tttcctctgg attccggcct ctggtcatcc    180
ctccccaccc tctctccaag gccctctcct ggtctcccctt cttctagaac ccttcctcc    240 acctccctct ctgcagaact tctcctttac cccccacccc ccaccactgc cccctttcct   300
tttctgacct cctttgggag ggctcagcgc tgcccagacc ataggagaga tgtgggaggc    360
tcagttcctg ggcttgctgt ttctgcagcc gctttgggtg gctccagtga agcctctcca    420
gccaggggct gaggtcccgg tggtgtgggc ccaggagggg gctcctgccc agctcccctg    480
```

```
cagccccaca atccccctcc aggatctcag ccttctgcga agagcagggg tcacttggca    540
gcatcagcca gacagtggcc cgcccgctgc cgccccggc  catccctgg  ccccggccc     600
tcacccggcg gcgccctcct cctggggcc  caggccccgc cgctacacgg tgctgagcgt    660
gggtcccgga ggcctgcgca gcgggaggct gcccctgcag cccgcgtcc  agctggatga    720
gcgcggccgg cagcgcgggg acttctcgct atggctgcgc ccagcccggc gcgcggacgc    780
cggcgagtac cgcgccgcgg tgcacctcag ggaccgcgcc ctctcctgcc gcctccgtct    840
gcgcctgggc caggcctcga tgactgccag ccccccagga tctctcagag cctccgactg    900
ggtcattttg aactgctcct tcagccgccc tgaccgccca gcctctgtgc attggttccg    960
gaaccggggc cagggccgag tccctgtccg ggagtccccc catcaccact tagcggaaag   1020
cttcctcttc ctgccccaag tcagcccat  ggactctggg ccctggggct gcatcctcac   1080
ctacagagat ggcttcaacg tctccatcat gtataacctc actgttctgg gtctggagcc   1140
cccaactccc ttgacagtgt acgctggagc aggttccagg gtggggctgc cctgccgcct   1200
gcctgctggt gtggggaccc ggtctttcct cactgccaag tggactcctc ctggggagg    1260
ccctgacctc ctggtgactg gagacaatgg cgactttacc cttcgactag aggatgtgag   1320
ccaggcccag gctgggacct acacctgcca tatccatctg caggaacagc agctcaatgc   1380
cactgtcaca ttggcaatca tcacagtgac tcccaaatcc tttgggtcac ctggatccct   1440
ggggaagctg ctttgtgagg tgactccagt atctggacaa gaacgctttg tgtggagctc   1500
tctggacacc ccatcccaga ggagtttctc aggaccttgg ctggaggcac aggaggccca   1560
gctcctttcc cagccttggc aatgccagct gtaccagggg gagaggcttc ttggagcagc   1620
agtgtacttc acagagctgt ctagcccagg tgcccaacgc tctgggagag ccccaggtgc   1680
cctcccagca ggccacctcc tgctgtttct catccttggt gtccttctc  tgctcctttt   1740
ggtgactgga gcctttggct ttcaccttttg gagaagacag tggcgaccaa gacgattttc   1800
tgccttagag caagggattc accctccgca ggctcagagc aagatagagg agctggagca   1860
agaaccggag ccggagccgg agccggaacc ggagcccgag cccgagcccg agccggagca   1920
gctctgacct ggagctgagg cagccagcag atctcagcag cccagtccaa ataaactccc   1980
tgtcagcagc aaaaa                                                    1995
```

<210> SEQ ID NO 43
<211> LENGTH: 311
<212> TYPE: PRT
<213> ORGANISM: Homo sapiens

<400> SEQUENCE: 43

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
                20                  25                  30

Phe Lys Val Ala Thr Pro Tyr Ser Leu Tyr Val Cys Pro Glu Gly Gln
            35                  40                  45

Asn Val Thr Leu Thr Cys Arg Leu Leu Gly Pro Val Asp Lys Gly His
        50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

```
Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Leu Val Tyr Lys Gln Arg Gln Ala Ala Ser Asn
    210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
        275                 280                 285

Pro Gly Pro Gly Asp Val Phe Phe Pro Ser Leu Asp Pro Val Pro Asp
    290                 295                 300

Ser Pro Asn Phe Glu Val Ile
305                 310

<210> SEQ ID NO 44
<211> LENGTH: 4774
<212> TYPE: DNA
<213> ORGANISM: Homo sapiens

<400> SEQUENCE: 44
ggggcggggt gcctggagca cggcgctggg gccgcccgca gcgctcactc gctcgcactc      60
agtcgcggga ggcttccccg cgccggccgc gtcccgcccg ctccccggca ccagaagttc     120
ctctgcgcgt ccgacggcga catgggcgtc cccacggccc tggaggccgg cagctggcgc     180
tgggatccc tgctcttcgc tctcttcctg gctgcgtccc taggtccggt ggcagccttc     240
aaggtcgcca cgccgtattc cctgtatgtc tgtcccgagg ggcagaacgt caccctcacc     300
tgcaggctct gggccctgt ggacaaaggg cacgatgtga ccttctacaa gacgtggtac     360
cgcagctcga ggggcgaggt gcagacctgc tcagagcgcc ggcccatccg caacctcacg     420
ttccaggacc ttcacctgca ccatggaggc caccaggctg ccaacaccag ccacgacctg     480
gctcagcgcc acgggctgga gtcggcctcc gaccaccatg gcaacttctc catcaccatg     540
cgcaacctga ccctgctgga tagcggcctc tactgctgcc tggtggtgga gatcaggcac     600
caccactcgg agcacagggt ccatggtgcc atggagctgc aggtgcagac aggcaaagat     660
gcaccatcca actgtgtggt gtacccatcc tcctcccagg atagtgaaaa catcacggct     720
gcagccctgg ctacgggtgc ctgcatcgta ggaatcctct gcctcccct catcctgctc     780
ctggtctaca gcaaaggca ggcagcctcc aaccgccgtg cccaggagct ggtgcgcatg     840
gacagcaaca ttcaagggat tgaaaacccc ggctttgaag cctcaccacc tgcccagggg     900
```

```
atacccgagg ccaaagtcag gcacccctg tcctatgtgg cccagcggca gccttctgag       960
tctgggcggc atctgctttc ggagcccagc accccctgt ctcctccagg ccccggagac      1020
gtcttcttcc catccctgga ccctgtccct gactctccaa actttgaggt catctagccc     1080
agctggggga cagtgggctg ttgtggctgg gtctggggca ggtgcatttg agccagggct     1140
ggctctgtga gtggcctcct tggcctcggc cctggttccc tccctcctgc tctgggctca    1200
gatactgtga catcccagaa gcccagcccc tcaaccctc tggatgctac atggggatgc     1260
tggacggctc agcccctgtt ccaaggattt tggggtgctg agattctccc ctagagacct    1320
gaaattcacc agctacagat gccaaatgac ttacatctta agaagtctca gaacgtccag    1380
cccttcagca gctctcgttc tgagacatga gccttgggat gtggcagcat cagtgggaca   1440
agatggacac tgggccaccc tcccaggcac cagacacagg gcacggtgga gagacttctc    1500
ccccgtggcc gccttggctc ccccgttttg cccgaggctg ctcttctgtc agacttcctc   1560
tttgtaccac agtggctctg gggccaggcc tgcctgccca ctggccatcg ccaccttccc   1620
cagctgcctc ctaccagcag tttctctgaa gatctgtcaa caggttaagt caatctgggg   1680
cttccactgc ctgcattcca gtccccagag cttggtggtc ccgaaacggg aagtacatat   1740
tggggcatgg tggcctccgt gagcaaatgg tgtcttgggc aatctgaggc caggacagat   1800
gttgccccac ccactggaga tggtgctgag ggaggtgggg ggggccttct ggggaaggtga   1860
gtggagaggg gcacctgccc cccgccctcc ccatccccta ctcccactgc tcagcgcggg   1920
ccattgcaag ggtgccacac aatgtcttgt ccaccctggg acacttctga gtatgaagcg   1980
ggatgctatt aaaaactaca tgggggaaaca ggtgcaaacc ctggagatgg attgtaagag  2040
ccagtttaaa tctgcactct gctgctcctc ccccacccc accttccact ccatacaatc    2100
tgggcctggt ggagtcttcg cttcagagcc attcggccag gtgcgggtga tgttcccatc   2160
tcctgcttgt gggcatgccc tggctttgtt tttatacaca taggcaaggt gagtcctctg    2220
tggaattgtg attgaaggat tttaaagcag gggaggagag tagggggcat ctctgtacac    2280
tctgggggta aaacagggaa ggcagtgcct gagcatgggg acaggtgagg tggggctggg   2340
cagaccccct gtagcgttta gcaggatggg ggccccaggt actgtggaga gcatagtcca   2400
gcctgggcat ttgtctccta gcagcctaca ctggctctgc tgagctgggc ctgggtgctg   2460
aaagccagga tttggggcta ggcgggaaga tgttcgccca attgcttggg gggttggggg  2520
gatggaaaag gggagcacct ctaggctgcc tggcagcagt gagccctggg cctgtggcta  2580
cagccaggga accccacctg gacacatggc cctgcttcta agccccccag ttaggcccaa   2640
aggaatggtc cactgagggc ctcctgctct gcctgggctg ggccagggc tttgaggaga    2700
gggtaaacat aggcccggag atggggctga cacctcgagt ggccagaata tgcccaaacc   2760
ccggcttctc ccttgtccct aggcagaggg gggtcccttc ttttgttccc tctggtcacc    2820
acaatgcttg atgccagctg ccataggaag agggtgctgg ctggccatgg tggcacacac    2880
ctgtcctccc agcactttgc agggctgagg tggaaggacc gcttaagccc aggtgttcaa    2940
ggctgctgtg agctgtgttc gagccactac actccagcct ggggacggag caaaactttg    3000
cctcaaaaca aattttaaaa agaaagaaag aaggaaagag ggtatgtttt tcacaattca    3060
tgggggcctg catggcagga gtggggacag gacacctgct gttcctggag tcgaaggaca    3120
agcccacagc ccagattccg gttctcccaa ctcaggaaga gcatgccctg ccctctgggg    3180
aggctggcct ggccccagcc ctcagctgct gaccttgagg cagagacaac ttctaagaat    3240
```

-continued

```
ttggctgcca gaccccaggc ctggctgctg ctgtgtggag agggaggcgg cccgcagcag    3300
aacagccacc gcacttcctc ctcagcttcc tctggtgcgg ccctgccctc tcttctctgg    3360
acccttttac aactgaacgc atctgggctt cgtggtttcc tgttttcagc gaaatttact    3420
ctgagctccc agttccatct tcatccatgg ccacaggccc tgcctacaac gcactaggga    3480
cgtccctccc tgctgctgct ggggaggggc aggctgctgg agccgccctc tgagttgccc    3540
gggatggtag tgcctctgat gccagccctg gtgctgtgtg gctggggtgc atggagagc    3600 tgggtgcgag aacatggcgc ctccagggg cgggaggagc actagggct ggggcaggag    3660 gctcctggag cgctggattc gtggcacagt ctgaggccct gagagggaaa tccatgcttt    3720
taagaactaa ttcattgtta ggagatcaat caggaattag gggccatctt acctatctcc    3780
tgacattcac agtttaatag agacttcctg cctttattcc ctcccaggga gaggctgaag    3840
gaatggaatt gaaagcacca tttggagggt tttgctgaca cagcggggac tgctcagcac    3900
tccctaaaaa cacaccatgg aggccactgg tgactgctgg tgggcaggct ggccctgcct    3960
gggggagtcc gtggcgatgg gcgctggggt ggaggtgcag gagccccagg acctgctttt    4020
caaaagactt ctgcctgacc agagctccca ctacatgcag tggcccaggg cagaggggct    4080
gatacatggc cttttttcagg gggtgctcct cgcggggtgg acttgggagt gtgcagtggg    4140
acagggggct gcaggggtcc tgccaccacc gagcaccaac ttggcccctg gggtcctgcc    4200
tcatgaatga ggccttcccc agggctggcc tgactgtgct gggggctggg ttaacgtttt    4260
ctcagggaac cacaatgcac gaaagaggaa ctggggttgc taaccaggat gctgggaaca    4320
aaggcctctt gaagcccagc cacagcccag ctgagcatga ggcccagccc atagacggca    4380
caggccacct ggcccattcc ctgggcattc cctgctttgc attgctgctt ctcttcaccc    4440
catggaggct atgtcaccct aactatcctg gaatgtgttg agagggattc tgaatgatca    4500
atatagcttg gtgagacagt gccgagatag atagccatgt ctgccttggg cacgggagag    4560
ggaagtggca gcatgcatgc tgtttcttgg ccttttctgt tagaatactt ggtgctttcc    4620
aacacacttt cacatgtgtt gtaacttgtt tgatccaccc ccttccctga aaatcctggg    4680
aggttttatt gctgccattt aacacagagg gcaatagagg ttctgaaagg tctgtgtctt    4740
gtcaaaacaa gtaaacggtg gaactacgac taaa                                4774
```

<210> SEQ ID NO 45
<211> LENGTH: 244
<212> TYPE: PRT
<213> ORGANISM: Homo sapiens

<400> SEQUENCE: 45

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
```

|  |  | 100 |  |  | 105 |  |  | 110 |  |  |
|---|---|---|---|---|---|---|---|---|---|---|

Tyr Pro Asp Gly Thr Tyr Thr Gly Arg Ile Phe Leu Glu Val Leu Glu
        115                    120                    125

Ser Ser Val Ala Glu His Gly Ala Arg Phe Gln Ile Pro Leu Leu Gly
        130                    135                    140

Ala Met Ala Ala Thr Leu Val Val Ile Cys Thr Ala Val Ile Val Val
145                    150                    155                    160

Val Ala Leu Thr Arg Lys Lys Lys Ala Leu Arg Ile His Ser Val Glu
        165                    170                    175

Gly Asp Leu Arg Arg Lys Ser Ala Gly Gln Glu Glu Trp Ser Pro Ser
            180                    185                    190

Ala Pro Ser Pro Pro Gly Ser Cys Val Gln Ala Glu Ala Ala Pro Ala
        195                  200                    205

Gly Leu Cys Gly Glu Gln Arg Gly Glu Asp Cys Ala Glu Leu His Asp
        210                  215                220

Tyr Phe Asn Val Leu Ser Tyr Arg Ser Leu Gly Asn Cys Ser Phe Phe
225                    230                    235                    240

Thr Glu Thr Gly

<210> SEQ ID NO 46
<211> LENGTH: 2978
<212> TYPE: DNA
<213> ORGANISM: Homo sapiens

<400> SEQUENCE: 46

| cgtcctatct | gcagtcggct | actttcagtg | gcagaagagg | ccacatctgc | ttcctgtagg | 60 |
|---|---|---|---|---|---|---|
| ccctctgggc | agaagcatgc | gctggtgtct | cctcctgatc | tgggcccagg | ggctgaggca | 120 |
| ggctcccctc | gcctcaggaa | tgatgacagg | cacaatagaa | acaacgggga | acatttctgc | 180 |
| agagaaaggt | ggctctatca | tcttacaatg | tcacctctcc | tccaccacgg | cacaagtgac | 240 |
| ccaggtcaac | tgggagcagc | aggaccagct | tctggccatt | tgtaatgctg | acttggggtg | 300 |
| gcacatctcc | ccatccttca | aggatcgagt | ggccccaggt | cccggcctgg | gcctcaccct | 360 |
| ccagtcgctg | accgtgaacg | atacagggga | gtacttctgc | atctatcaca | cctaccctga | 420 |
| tgggacgtac | actgggagaa | tcttcctgga | ggtcctagaa | agctcagtgg | ctgagcacgg | 480 |
| tgccaggttc | cagattccat | gcttggagc | catggccgcg | acgctggtgg | tcatctgcac | 540 |
| agcagtcatc | gtggtggtcg | cgttgactag | aaagaagaaa | gccctcagaa | tccattctgt | 600 |
| ggaaggtgac | ctcaggagaa | atcagctgg | acaggaggaa | tggagcccca | gtgctccctc | 660 |
| accccccagga | agctgtgtcc | aggcagaagc | tgcacctgct | gggctctgtg | gagagcagcg | 720 |
| gggagaggac | tgtgccgagc | tgcatgacta | cttcaatgtc | ctgagttaca | gaagcctggg | 780 |
| taactgcagc | ttcttcacag | agactggtta | gcaaccagag | gcatcttctg | gaagatacac | 840 |
| ttttgtcttt | gctattatag | atgaatatat | aagcagctgt | actctccatc | agtgctgcgt | 900 |
| gtgtgtgtgt | gtgtgtatgt | gtgtgtgtgt | tcagttgagt | gaataaatgt | catcctcttc | 960 |
| tccatcttca | tttccttggc | cttttcgttc | tattccattt | tgcattatgg | caggcctagg | 1020 |
| gtgagtaacg | tggatcttga | tcataaatgc | aaaattaaaa | aatatcttga | cctggtttta | 1080 |
| aatctggcag | tttgagcaga | tcctatgtct | ctgagagaca | cattcctcat | aatggccagc | 1140 |
| attttgggct | acaaggtttt | gtggttgatg | atgaggatgg | catgactgca | gagccatcct | 1200 |
| catctcattt | tttcacgtca | ttttcagtaa | ctttcactca | ttcaaaggca | ggttataagt | 1260 |
| aagtcctggt | agcagcctct | atggggagat | ttgagagtga | ctaaatcttg | gtatctgccc | 1320 |

```
tcaagaactt acagttaaat ggggagacaa tgttgtcatg aaaaggtatt atagtaagga    1380
gagaaggaga catacacagg ccttcaggaa gagacgacag tttggggtga ggtagttggc    1440
ataggcttat ctgtgatgaa gtggcctggg agcaccaagg ggatgttgag gctagtctgg    1500
gaggagcagg agttttgtct agggaacttg taggaaattc ttggagctga aagtcccaca    1560
aagaaggccc tggcaccaag ggagtcagca aacttcagat tttattctct gggcaggcat    1620
ttcaagtttc cttttgctgt gacatactca tccattagac agcctgatac aggcctgtag    1680
cctcttccgg ccgtgtgtgc tggggaagcc ccaggaaacg cacatgccca cacagggagc    1740
caagtcgtag catttgggcc ttgatctacc ttttctgcat caatacactc ttgagcctt     1800
gaaaaagaa cgtttcccac taaaaagaaa atgtggattt ttaaaatagg gactcttcct    1860
aggggaaaaa gggggctgg gagtgataga gggtttaaaa aataaacacc ttcaaactaa     1920
cttcttcgaa ccctttatt cactccctga cgactttgtg ctggggttgg ggtaactgaa    1980
ccgcttattt ctgtttaatt gcattcaggc tggatcttag aagacttta tccttccacc    2040
atctctctca gaggaatgag cggggaggtt ggatttactg gtgactgatt ttctttcatg    2100
ggccaaggaa ctgaaagaga atgtgaagca aggttgtgtc ttgcgcatgg ttaaaaataa    2160
agcattgtcc tgcttcctaa gacttagact ggggttgaca attgttttag caacaagaca    2220
attcaactat ttctcctagg attttatta ttattatttt ttcacttttc taccaaatgg     2280
gttacatagg aagaatgaac tgaaatctgt ccagagctcc aagtcctttg gaagaaagat    2340
tagatgaacg taaaatgtt gttgtttgct gtggcagttt acagcatttt tcttgcaaaa     2400
ttagtgcaaa tctgttggaa atagaacaca attcacaaat tggaagtgaa ctaaaatgta    2460
atgacgaaaa gggagtagtg ttttgatttg gaggaggtgt atattcggca gaggttggac    2520
tgagagttgg gtgttattta acataattat ggtaattggg aaacatttat aaacactatt    2580
gggatggtga taaaatacaa aagggcctat agatgttaga aatgggtcag gttactgaaa    2640
tgggattcaa tttgaaaaaa attttttaa atagaactca ctgaactaga ttctcctctg     2700
agaaccagag aagaccattt catagttgga ttcctggaga catgcgctat ccaccacgta    2760
gccactttcc acatgtggcc atcaaccact taagatgggg ttagtttaaa tcaagatgtg    2820
ctgttataat tggtataagc ataaaatcac actagattct ggagatttaa tatgaataat    2880
aagaatacta tttcagtagt tttggtatat tgtgtgtcaa aaatgataat attttggatg    2940
tattgggtga aataaaatat taacattaaa aaaaaaa                             2978
```